(12) United States Patent
Kortylewski et al.

(10) Patent No.: US 10,801,026 B2
(45) Date of Patent: Oct. 13, 2020

(54) COMPOUNDS AND COMPOSITIONS INCLUDING PHOSPHOROTHIOATED OLIGODEOXYNUCLEOTIDE, AND METHODS OF USE THEREOF

(71) Applicant: City of Hope, Duarte, CA (US)

(72) Inventors: Marcin Tomasz Kortylewski, Monrovia, CA (US); Piotr Marek Swiderski, San Dimas, CA (US); Guido Marcucci, Azusa, CA (US); Bin Zhang, Duarte, CA (US); Ya-Huei Kuo, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/768,405

(22) PCT Filed: Oct. 14, 2016

(86) PCT No.: PCT/US2016/057143
§ 371 (c)(1),
(2) Date: Apr. 13, 2018

(87) PCT Pub. No.: WO2017/066639
PCT Pub. Date: Apr. 20, 2017

(65) Prior Publication Data
US 2018/0312837 A1    Nov. 1, 2018

Related U.S. Application Data

(60) Provisional application No. 62/242,189, filed on Oct. 15, 2015.

(51) Int. Cl.
| | | |
|---|---|---|
| *C07H 21/02* | (2006.01) | |
| *C07H 21/04* | (2006.01) | |
| *C12N 15/113* | (2010.01) | |
| *A61K 31/7004* | (2006.01) | |
| *A61K 47/54* | (2017.01) | |
| *A61K 31/704* | (2006.01) | |
| *A61K 45/06* | (2006.01) | |
| *C12N 15/11* | (2006.01) | |
| *A61K 31/7125* | (2006.01) | |
| *A61P 35/02* | (2006.01) | |
| *A61K 31/506* | (2006.01) | |

(52) U.S. Cl.
CPC .......... *C12N 15/113* (2013.01); *A61K 31/506* (2013.01); *A61K 31/7004* (2013.01); *A61K 31/704* (2013.01); *A61K 31/7125* (2013.01); *A61K 45/06* (2013.01); *A61K 47/549* (2017.08); *A61P 35/02* (2018.01); *C12N 15/111* (2013.01); *C12N 2310/113* (2013.01); *C12N 2310/141* (2013.01); *C12N 2310/17* (2013.01); *C12N 2310/315* (2013.01); *C12N 2310/3519* (2013.01)

(58) Field of Classification Search
CPC .......................... C12N 15/113; C12N 15/111
See application file for complete search history.

(56) References Cited

U.S. PATENT DOCUMENTS

| | | | | |
|---|---|---|---|---|
| 10,112,900 | B2 * | 10/2018 | Stafford | C07D 213/55 |
| 10,202,606 | B2 * | 2/2019 | Ishii | A61K 39/145 |
| 2012/0065245 | A1 * | 3/2012 | Baltimore | A61K 31/7105 |
| | | | | 514/44 A |
| 2012/0295963 | A1 | 11/2012 | Soreq et al. | |
| 2014/0004154 | A1 * | 1/2014 | Pascolo | A61K 9/0019 |
| | | | | 424/278.1 |
| 2014/0066610 | A1 * | 3/2014 | Schaus | C12Q 1/6816 |
| | | | | 536/23.1 |
| 2014/0377322 | A1 * | 12/2014 | Park | A61L 31/10 |
| | | | | 424/423 |
| 2015/0197744 | A1 | 7/2015 | de Boer et al. | |
| 2017/0182177 | A1 * | 6/2017 | Rana | A61K 9/0019 |

FOREIGN PATENT DOCUMENTS

| | | |
|---|---|---|
| WO | WO-2008/116267 A1 | 10/2008 |
| WO | WO-2013/040429 A1 | 3/2013 |

OTHER PUBLICATIONS

Deleavey, G.F. et al. (Aug. 24, 2012). "Designing chemically modified oligonucleotides for targeted gene silencing," *Chem Biol* 19(8):937-954.

Doster, A. et al. (Jun. 2013). "Phosphorothioate-modified CpG oligodeoxynucleotides mimic autoantigens and reveal a potential role for Toll-like receptor 9 in receptor revision," *Immunology* 139(2):166-178.

European Search Report dated May 21, 2019, for EP Patent Application No. 16856317.9, 21 pages.

International Search Report dated Dec. 22, 2016 for PCT Application No. PCT/US2016/057143, filed Oct. 14, 2016, 4 pages.

Krieg, A.M. et al. (Apr. 2012, e-published Feb. 21, 2012). "CpG still rocks! Update on an accidental drug," *Nucleic Acid Ther* 22(2):77-89.

(Continued)

*Primary Examiner* — Amy H Bowman
(74) *Attorney, Agent, or Firm* — Mintz, Levin, Cohn, Ferris, Glovsky and Popeo, P.C.

(57) ABSTRACT

The present disclosure relates to a compound including a nucleic acid sequence conjugated to an anti-microRNA or a microRNA-mimic or a compound including a modified anti-microRNA sequence, compositions of such a compound, and method of treatment of a disease, and method of suppressing microRNA activity by the disclosed compound or composition.

15 Claims, 61 Drawing Sheets

Specification includes a Sequence Listing.

(56) References Cited

OTHER PUBLICATIONS

Lennox, K.A. et al. (Dec. 2011, e-published Jul. 14, 2011). "Chemical modification and design of anti-miRNA oligonucleotides," *Gene Ther* 18(12):1111-1120.

Monteys, A.M. et al. (Mar. 2010, e-published Jan. 14, 2010). "Structure and activity of putative intronic miRNA promoters," *RNA* 16(3):495-505.

Nechaev, S. et al. (Sep. 28, 2013, e-published Jun. 15, 2013). "Intracellular processing of immunostimulatory CpG-siRNA: Toll-like receptor 9 facilitates siRNA dicing and endosomal escape," *J Control Release* 170(3):307-315.

Written Opinion dated Dec. 22, 2016 for PCT Application No. PCT/US2016/057143, filed Oct. 14, 2016, 4 pages.

Zhang, B. et al. (Dec. 3, 2015). "Knockdown (KD) of Mir-126 Expression Enhances Tyrosine Kinase Inhibitor (TKI)-Mediated Targeting of Chronic Myelogenous Leukemia (CML) Stem Cells," *Blood* 126(23), 7 pages.

Ziegler et al. (Nov. 16, 2013). "Bifunctional oligodeoxynucleotide/ antagomiR constructs: evaluation of a new tool for microRNA silencing," *Nucleic Acid Therapeutics*, 23(6): 427-434.

Cammarata, G. et al. (May 2010). "Differential expression of specific microRNA and their targets in acute myeloid leukemia," *Am J Hematol* 85(5):331-339.

Deleeuw, D.C. et al. (Apr. 1, 2014, e-published Jan. 29, 2014). "Attenuation of microRNA-126 expression that drives CD34+38- stem/progenitor cells in acute myeloid leukemia leads to tumor eradication," *Cancer Res* 74(7):2094-2105.

Wang, S. et al. (Aug. 2008). "The endothelial-specific microRNA miR-126 governs vascular integrity and angiogenesis," *Dev Cell* 15(2):261-271.

\* cited by examiner

FIG. 1

| CpG(D19)-anti-miR126 | 2'OMe | 5' G*G*T GCA TCG ATG CAGG G*G*G* G*G* G*G (SEQ ID NO: 1) xxxxx mCmGmCmAmUmUmAUmUmAmCmUmAmCmGmGmUmAmCm GmA (SEQ ID NO: 17) 3' |
|---|---|---|
| CpG(D19)-scrambled RNA | 2'OMe | 5' G*G*T GCA TCG ATG CAGG G*G*G* G*G* G*G (SEQ ID NO: 1) xxxxx mGmUmAmAmGmAmAmCmCmGmUmAmAmCmGmUmCmAmCmU mUmA (SEQ ID NO: 32) 3' |

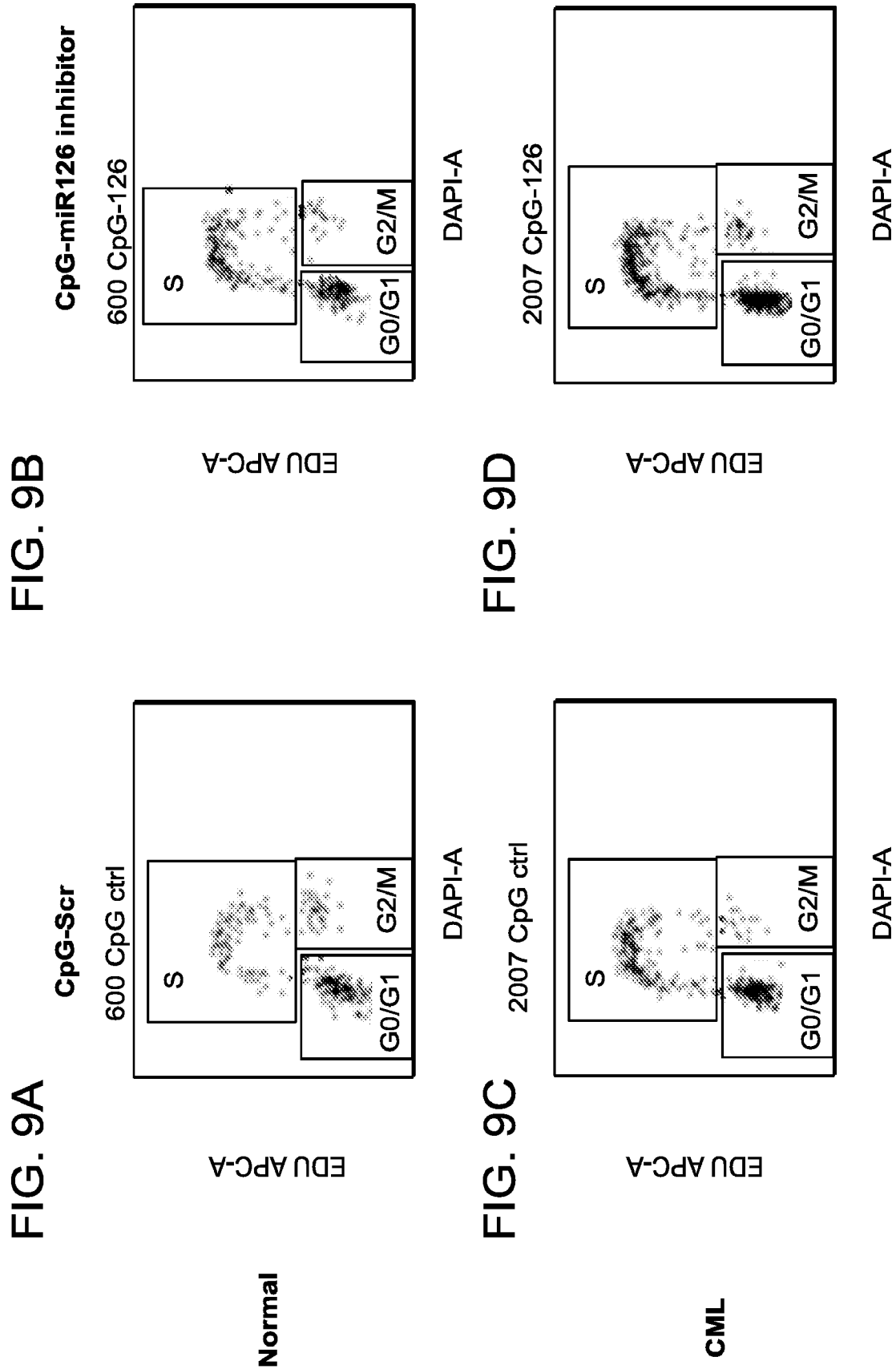

RAW264.7

| Cell dose/mouse | Leukemia developed/tested | | | |
|---|---|---|---|---|
| | scrRNA | Inhibitor | scrRNA+NIL | Inhibitor +NIL |
| 4 million | 6/6 | 2/6 | 3/6 | 0/6 |
| 2 million | 2/6 | 1/6 | 3/6 | 0/6 |
| 1 million | 2/6 | 0/6 | 2/6 | 0/6 |
| 0.5 million | 1/6 | 0/6 | 0/6 | 0/6 |
| Frequency of LIC | 4.20E-07 | 7.54E-08 | 2.36E-07 | 0 |

FIG. 26E

| CpG | CpG(D19)-anti-mir126 | 2'OMe | 5' G*G*T GCA TCG ATG CAG G*G*G*G*G xxxxx mCmGmC mAmUmU mAmUmU mAmCmU mCmAmC mGmGmU mAmCmG mA 3' (SEQ ID NOS.:1, 17) |
|---|---|---|---|
| GM1440 | GpC(D19)-anti-mir126 | PS + 2'OMe | 5' G*G*T GCA TGC ATG CAG G*G*G*G*G xxxxx mCmGmC mAmUmU mAmUmU mAmCmU mCmAmC mGmGmU mAmCmG mA 3' (SEQ ID NOS.: 2, 17) |
| GM1441 | PS(D19)-anti-mir126 | All PS 2'OMe | 5' G*G*T*G*C*A*T*C*G*A*T*G*C*A*G*G*G*G*G*G xxxxx mCmGmC mAmUmU mAmUmU mAmCmU mCmAmC mGmGmU mAmCmG mA 3' (SEQ ID NOS.:3, 17) |
| GM1441B | PS(D19)-anti-mir126 | All PS 2'OMe+ all PS | 5' G*G*T*G*C*A*T*C*G*A*T*G*C*A*G*G*G*G*G*G xxxxx mC*mG*mC* mA*mU*mU* mA*mU*mU* mA*mC*mU* mC*mA*mC* mG*mG*mU* mA*mC*mG*mA 3' (SEQ ID NOS.:3, 48) |
| GM 1141: | miRNA part phoshorothioated (=GM1441B) | | |
| GM615 | CpG D19-Sense mir126 unmodified | | 5'- G*G*TGCATCGATGCAGG*G*G*G*G xxxxx rUrCrG rUrArC rCrGrU rGrArG rUrArA rUrArA rUrGrC rGrUrU-3' (SEQ ID NOS.:1, 18) |
| GM616 | CpG D19-Sense mir126 Fluoro modified 2U at 3' end | | 5'- G*G*TGCATCGATGCAGG*G*G*G*G xxxxx rUrCrG rUrArC rCrGrU rGrArG rUrArA rUrArA rUrGrC rGfUfU-3' (SEQ ID NOS.:1, 19) |
| GM617 | CpG D19-Sense mir126 All pyrimidines Fluoro modified | | 5'- G*G*TGCATCGATGCAGG*G*G*G*G xxxxx fUrAfC fCrGfU rGrArG fUrArA fUrArA fUrGfC rGfUfU-3' (SEQ ID NOS.:1, 20) |
| | Complementary mir | | 5'- rCrGrC rArUrU rArUrU rArCrU rCrArC rGrGrU rArCrG rA -3' (SEQ ID NO.: 21) |

US 10,801,026 B2

SEQUENCE LISTING

```
<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate

<400> SEQUENCE: 1
ggtgcatcga tgcagggggg                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate

<400> SEQUENCE: 2
ggtgcatgca tgcagggggg                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
```

```
<400> SEQUENCE: 3
ggtgcatcga tgcagggggg                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate

<400> SEQUENCE: 4
tccatgacgt tcctgatgct                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue modified with phosphorothioate
<220> FEATURE:
<221> NAME/KEY: misc_feature
<222> LOCATION: (2)..(2)
<223> OTHER INFORMATION: Residue optionally modified with
      phosphorothioate
<220> FEATURE:
<221> NAME/KEY: misc_feature
<222> LOCATION: (15)..(19)
<223> OTHER INFORMATION: Residue modified with phosphorothioate

<400> SEQUENCE: 5
ggggtcaacg ttgagggggg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue modified with phosphorothioate
<220> FEATURE:
<221> NAME/KEY: misc_feature
<222> LOCATION: (2)..(2)
<223> OTHER INFORMATION: Residue optionally modified with
      phosphorothioate
<220> FEATURE:
<221> NAME/KEY: misc_feature
<222> LOCATION: (15)..(19)
<223> OTHER INFORMATION: Residue modified with phosphorothioate

<400> SEQUENCE: 6
gggggacgat cgtcgggggg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (1)..(1)
<223> OTHER INFORMATION: Residue modified with phosphorothioate
<220> FEATURE:
<221> NAME/KEY: misc_feature
<222> LOCATION: (2)..(2)
<223> OTHER INFORMATION: Residue optionally modified with
      phosphorothioate
<220> FEATURE:
<221> NAME/KEY: misc_feature
<222> LOCATION: (16)..(19)
<223> OTHER INFORMATION: Residue modified with phosphorothioate

<400> SEQUENCE: 7
ggtgcatcga tgcagggggg                                              20

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (3)..(3)
<223> OTHER INFORMATION: Residue optionally modified with
      phosphorothioate
<220> FEATURE:
<221> NAME/KEY: misc_feature
<222> LOCATION: (16)..(20)
<223> OTHER INFORMATION: Residue modified with phosphorothioate

<400> SEQUENCE: 8
ggggacgacg tcgtgggggg g                                            21

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate

<400> SEQUENCE: 9
tccatgacgt tcctgatgct                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate

<400> SEQUENCE: 10
tccatgacgt tcctgacgtt                                              20

<210> SEQ ID NO 11
<211> LENGTH: 24
<212> TYPE: DNA
<213> ORGANISM: Artificial Sequence
```

```
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate

<400> SEQUENCE: 11
tcgtcgtttt gtcgttttgt cgtt                                              24

<210> SEQ ID NO 12
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: Residue modified with phosphorothioate

<400> SEQUENCE: 12
tcgtcgttgt cgttttgtcg tt                                                22

<210> SEQ ID NO 13
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: Residue modified with phosphorothioate

<400> SEQUENCE: 13
tcgtcgtttt cggcgcgcgc cg                                                22

<210> SEQ ID NO 14
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(24)
<223> OTHER INFORMATION: Residue modified with phosphorothioate

<400> SEQUENCE: 14
tcgtcgtcgt tcgaacgacg ttgat                                             25

<210> SEQ ID NO 15
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 15 rycgyr                                                                   6

<210> SEQ ID NO 16
<211> LENGTH: 22
<212> TYPE: RNA
<213> ORGANISM: Artificial Sequence
<220> FEATURE:
<223> OTHER INFORMATION: Synthetic polynucleotide
```

```
<400> SEQUENCE: 16
cgcauuauua cucacgguac ga                                                22

<210> SEQ ID NO 17
<211> LENGTH: 22
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(22)
<223> OTHER INFORMATION: Residue modified with 2'-O-methyl

<400> SEQUENCE: 17
cgcauuauua cucacgguac ga                                                22

<210> SEQ ID NO 18
<211> LENGTH: 24
<212> TYPE: RNA
<213> ORGANISM: Artificial Sequence
<220> FEATURE:
<223> OTHER INFORMATION: Synthetic polynucleotide

<400> SEQUENCE: 18
ucguaccgug aguaauaaug cguu                                              24

<210> SEQ ID NO 19
<211> LENGTH: 24
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (23)..(24)
<223> OTHER INFORMATION: Residue modified with fluoro

<400> SEQUENCE: 19
ucguaccgug aguaauaaug cguu                                              24

<210> SEQ ID NO 20
<211> LENGTH: 21
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue modified with fluoro
<220> FEATURE:
<221> NAME/KEY: misc_feature
<222> LOCATION: (3)..(4)
<223> OTHER INFORMATION: Residue modified with fluoro
<220> FEATURE:
<221> NAME/KEY: misc_feature
<222> LOCATION: (6)..(6)
<223> OTHER INFORMATION: Residue modified with fluoro
<220> FEATURE:
<221> NAME/KEY: misc_feature
<222> LOCATION: (10)..(10)
<223> OTHER INFORMATION: Residue modified with fluoro
<220> FEATURE:
<221> NAME/KEY: misc_feature
<222> LOCATION: (13)..(13)
<223> OTHER INFORMATION: Residue modified with fluoro
<220> FEATURE:
<221> NAME/KEY: misc_feature
<222> LOCATION: (16)..(16)
<223> OTHER INFORMATION: Residue modified with fluoro
```

```
<220> FEATURE:
<221> NAME/KEY: misc_feature
<222> LOCATION: (18)..(18)
<223> OTHER INFORMATION: Residue modified with fluoro
<220> FEATURE:
<221> NAME/KEY: misc_feature
<222> LOCATION: (20)..(21)
<223> OTHER INFORMATION: Residue modified with fluoro

<400> SEQUENCE: 20
uaccgugagu aauaaugcgu u                                              21

<210> SEQ ID NO 21
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 21
cgcauuauua cucacgguac ga                                             22

<210> SEQ ID NO 22
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 22
uccauaaagu aggaaacacu aca                                            23

<210> SEQ ID NO 23
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 23
uguaguguuu ccuacuuuau ggauu                                          25

<210> SEQ ID NO 24
<211> LENGTH: 25
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(25)
<223> OTHER INFORMATION: Residue modified with fluoro

<400> SEQUENCE: 24
uguaguguuu ccuacuuuau ggauu                                          25

<210> SEQ ID NO 25
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 25
uccauaaagu aggaaacacu aca                                            23

<210> SEQ ID NO 26
```

```
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 26
uguuaaugcu aauauguagg ag                                              22

<210> SEQ ID NO 27
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(6)
<223> OTHER INFORMATION: Residue is t or u
<220> FEATURE:
<221> NAME/KEY: misc_feature
<222> LOCATION: (8)..(8)
<223> OTHER INFORMATION: Residue is t or u
<220> FEATURE:
<221> NAME/KEY: misc_feature
<222> LOCATION: (14)..(15)
<223> OTHER INFORMATION: Residue is t or u
<220> FEATURE:
<221> NAME/KEY: misc_feature
<222> LOCATION: (20)..(21)
<223> OTHER INFORMATION: Residue is t or u

<400> SEQUENCE: 27
acccctatca caattagcat taa                                             23

<210> SEQ ID NO 28
<211> LENGTH: 23
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(22)
<223> OTHER INFORMATION: Residue modified with phosphorothioate
<220> FEATURE:
<221> NAME/KEY: misc_feature
<222> LOCATION: (1)..(23)
<223> OTHER INFORMATION: Residue modified with 2'-O-methyl

<400> SEQUENCE: 28
accccuauca caauuagcau uaa                                             23

<210> SEQ ID NO 29
<211> LENGTH: 24
<212> TYPE: RNA
<213> ORGANISM: Artificial Sequence
<220> FEATURE:
<223> OTHER INFORMATION: Synthetic polynucleotide

<400> SEQUENCE: 29
cuccuacaua uuagcauuaa cauu                                            24

<210> SEQ ID NO 30
<211> LENGTH: 24
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
```

```
<222> LOCATION: (23)..(24)
<223> OTHER INFORMATION: Residue modified with fluoro

<400> SEQUENCE: 30
cuccuacaua uuagcauuaa cauu                                              24

<210> SEQ ID NO 31
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 31
uguuaaugcu aauauguagg ag                                                22

<210> SEQ ID NO 32
<211> LENGTH: 22
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(22)
<223> OTHER INFORMATION: Residue modified with 2'-O-methyl

<400> SEQUENCE: 32
guagaaccgu acucgucacu ua                                                22

<210> SEQ ID NO 33
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue can be t or u
<220> FEATURE:
<221> NAME/KEY: misc_feature
<222> LOCATION: (8)..(9)
<223> OTHER INFORMATION: Residue can be t or u
<220> FEATURE:
<221> NAME/KEY: misc_feature
<222> LOCATION: (14)..(14)
<223> OTHER INFORMATION: Residue can be t or u
<220> FEATURE:
<221> NAME/KEY: misc_feature
<222> LOCATION: (16)..(16)
<223> OTHER INFORMATION: Residue can be t or u

<400> SEQUENCE: 33
tcacaagtta gggtctcagg ga                                                22

<210> SEQ ID NO 34
<211> LENGTH: 22
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: Residue modified with phosphorothioate
<220> FEATURE:
<221> NAME/KEY: misc_feature
<222> LOCATION: (1)..(22)
<223> OTHER INFORMATION: Residue modified 2'-O-methyl
```

```
<400> SEQUENCE: 34
ucacaaguua gggucucagg ga                                              22

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (5)..(5)
<223> OTHER INFORMATION: Residue can be t or u
<220> FEATURE:
<221> NAME/KEY: misc_feature
<222> LOCATION: (10)..(11)
<223> OTHER INFORMATION: Residue can be t or u
<220> FEATURE:
<221> NAME/KEY: misc_feature
<222> LOCATION: (15)..(16)
<223> OTHER INFORMATION: Residue can be t or u
<220> FEATURE:
<221> NAME/KEY: misc_feature
<222> LOCATION: (18)..(18)
<223> OTHER INFORMATION: Residue can be t or u

<400> SEQUENCE: 35
cccatggaat tcagttctca                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (1)..(20)
<223> OTHER INFORMATION: Residue modified 2'-O-methyl

<400> SEQUENCE: 36
cccatggaat tcagttctca                                                 20

<210> SEQ ID NO 37
<211> LENGTH: 85
<212> TYPE: DNA
<213> ORGANISM: Artificial Sequence
<220> FEATURE:
<223> OTHER INFORMATION: Synthetic polynucleotide

<400> SEQUENCE: 37
cgctggcgac gggacattat tactttggt acgcgctgtg acacttcaaa ctcgtaccgt      60
gagtaataat gcgccgtcca cggca                                           85

<210> SEQ ID NO 38
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 38
gacagtgcag tcacccataa agtagaaagc actactaaca gcactggagg gtgtagtgtt     60
tcctacttta tggatgagtg tactgtg                                         87
```

<210> SEQ ID NO 39
<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 39
ctgttaatgc taatcgtgat aggggttttt gcctccaact gactcctaca tattagcatt    60
aacag                                                                65

<210> SEQ ID NO 40
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 40
cggggttggt tgttatcttt ggttatctag ctgtatgagt ggtgtggagt cttcataaag    60
ctagataacc gaaagtaaaa ataacccca                                      89

<210> SEQ ID NO 41
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 41
ggaggcccgt ttctctcttt ggttatctag ctgtatgagt gccacagagc cgtcataaag    60
ctagataacc gaaagtagaa atgattctca                                     90

<210> SEQ ID NO 42
<211> LENGTH: 110
<212> TYPE: DNA
<213> ORGANISM: Artificial Sequence
<220> FEATURE:
<223> OTHER INFORMATION: Synthetic polynucleotide

<400> SEQUENCE: 42
ccagaggttg taacgttgtc tatatatacc ctgtagaacc gaatttgtgt ggtatccgta    60
tagtcacaga ttcgattcta ggggaatata tggtcgatgc aaaaacttca              110

<210> SEQ ID NO 43
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 43
tgtcgggtag cttatcagac tgatgttgac tgttgaatct catggcaaca ccagtcgatg    60
ggctgtctga ca                                                        72

<210> SEQ ID NO 44
<211> LENGTH: 84
<212> TYPE: DNA
<213> ORGANISM: Artificial Sequence
<220> FEATURE:
<223> OTHER INFORMATION: Synthetic polynucleotide

```
<400> SEQUENCE: 44
gtcagaataa tgtcaaagtg cttacagtgc aggtagtgat atgtgcatct actgcagtga    60
aggcacttgt agcattatgg tgac                                          84

<210> SEQ ID NO 45
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 45
ctttctacac aggttgggat cggttgcaat gctgtgtttc tgtatggtat tgcacttgtc    60
ccggcctgtt gagtttgg                                                 78

<210> SEQ ID NO 46
<211> LENGTH: 88
<212> TYPE: DNA
<213> ORGANISM: Artificial Sequence
<220> FEATURE:
<223> OTHER INFORMATION: Synthetic polynucleotide

<400> SEQUENCE: 46
tgcgctcctc tcagtccctg agaccctaac ttgtgatgtt taccgtttaa atccacgggt    60
taggctcttg ggagctgcga gtcgtgct                                      88

<210> SEQ ID NO 47
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 47
ccgatgtgta tcctcagctt tgagaactga attccatggg ttgtgtcagt gtcagacctc    60
tgaaattcag ttcttcagct gggatatctc tgtcatcgt                          99

<210> SEQ ID NO 48
<211> LENGTH: 22
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: Residue modified with phosphorothioate
<220> FEATURE:
<221> NAME/KEY: misc_feature
<222> LOCATION: (1)..(22)
<223> OTHER INFORMATION: Residue modified with 2'-O-methyl

<400> SEQUENCE: 48
cgcauuauua cucacgguac ga                                            22
```

COMPOUNDS AND COMPOSITIONS INCLUDING PHOSPHOROTHIOATED OLIGODEOXYNUCLEOTIDE, AND METHODS OF USE THEREOF

CROSS-REFERENCES TO RELATED APPLICATIONS

This application is a national stage application filed under 35 U.S.C. § 371, of International Patent Application No. PCT/US2016/057143, filed Oct. 14, 2016, which claims the benefit of and priority under 35 U.S.C. § 119(e) to U.S. Provisional Application Ser. No. 62/242,189, filed Oct. 15, 2015, the entire contents of each of which are hereby expressly incorporated by reference herein.

INCORPORATION BY REFERENCE OF SEQUENCE LISTING

The contents of the txt file named 048440-588N01US_ST25.TXT, created on Apr. 10, 2018, and is 15,873 bytes in size, are hereby incorporated by reference in their entireties.

BACKGROUND OF THE DISCLOSURE

Acute myeloid leukemia is characterized by accumulation of immature myeloid progenitor cells. Leukemogenesis results from deregulation of oncogenes, tumor suppressors or transcription factors which control myeloid lineage differentiation, self-renewal and/or proliferation. The present disclosure relates to compounds, compositions, and methods of treating cancer, e.g., AML, CML and myelodysplastic syndrome, with anti-miRs and miRNA mimics that are stable and are suitable for systemic administration against disseminated cancers.

BRIEF SUMMARY OF THE DISCLOSURE

In one aspect, provided herein is a compound including a phosphorothioated CpG oligodeoxynucleotide (CpG-ODN), conjugated to an anti-microRNA (anti-miR) or to a microRNA (miRNA)-mimic nucleic acid sequence (miRNA-mimic).

In another aspect, provided herein is a compound including an anti-microRNA (anti-miR) sequence, where the anti-miR sequence contains one or more phosphorothioate linkages and one or more chemically modified nucleotides.

In another aspect, provided herein is a pharmaceutical composition including a pharmaceutically acceptable excipient and a compound described herein.

In another aspect, provided herein is a method of treating a disease in a subject in need thereof. The method includes administering to the subject an effective amount of a compound described herein or a pharmaceutical composition described herein.

In another aspect, provided herein is a method of reducing the activity of microRNA in a cell. The method includes contacting the cell with an effective amount of a compound described herein.

Other features and advantages of the disclosure will be apparent from the following detailed description and claims.

Unless noted to the contrary, all publications, references, patents and/or patent applications reference herein are hereby incorporated by reference in their entirety for all purposes.

BRIEF DESCRIPTION OF THE DRAWINGS

FIG. 1 is a schematic that shows the design of the chemically stabilized CpG-anti-miR-126 RNA oligonucleotides. Asterix (*) indicate phosphorothioate linkages; and mN indicates a 2' OMe modified nucleotide.

FIG. 2A is a histogram showing uptake in NL/CB cells with 600 CpG siRNA. FIG. 2B is a histogram showing NL/CB cells with 500 CpG-siRNA. FIG. 2C is a histogram showing uptake in AML cells. FIG. 2D is a histogram showing uptake in CML cells. Uptake was measured by Cy3 expression in these cells by flow cytometry.

FIG. 3A is a histogram showing uptake in K562 cells. FIG. 3B is a histogram showing uptake in KG1A AML cells. FIG. 3C is a histogram showing uptake in MV4-11 AML cells. FIG. 3D is a histogram showing uptake in Molm13 AML cells. FIG. 3E is a histogram showing uptake in NB4 AML cells. FIG. 3F is a histogram showing uptake in OCI AML cells. FIG. 3G is a histogram showing uptake in HL60 AML cells.

FIG. 4A is a bar graph showing miRNA 126 expression in the K562 CML cell line. FIG. 4B is a bar graph showing miRNA 126 expression in the KG1A AML cell line. FIG. 4C is a bar graph showing miRNA 126 expression in the MV4-11 AML cell line. FIG. 4D is a bar graph showing the miRNA 126 expression in the Molm13 AML cell line. FIG. 4E is a bar graph showing the miRNA 126 expression in the NB4 AML cell line. FIG. 4F is a bar graph showing the miRNA 126 expression in the OCI AML cell line. FIG. 4G is a bar graph showing the miRNA 126 expression in the HL60 AML cell line.

FIGS. 9A-9D are a series of cell sorting plots showing increased cell cycle in CD34+CD38− cells after knockdown of miR-12. Normal (NL; FIGS. 9A-9B) and CML human CD34+CD38− cells (FIGS. 9C-9D) were sorted and then cultured with 500 nm CpG-miR126 inh-Cy3 or CpG-SCR control for 72 hours, and then cell cycling was analyzed by EDU/DAPi staining. Increased cell cycling was seen in human CD34+CD38− cells after knockdown of miR-126 (FIG. 9D).

FIGS. 16A-16B. Cell-selective uptake of CpG-anti-miR146a. FIGS. 16A-16B) Dose and time dependent internalization of CpG-antimiR146a by target immune and leukemic cells without any transfection reagents. CpG-anti-miR146a was Cy3-labeled to detect the intracellular uptake by target cells using flow cytometry. FIG. 16A) Human immune cells were incubated with indicated concentrations of CpG-anti-miR146acY3 for 1 hr. The uptake by CD14+ monocytes, CD1c+ mDCs, CD3+ T cells and CD19+ B cells was measured using flow cytometry. FIG. 16B) Cultured human AML cells KG1a, MOLM13, and MOLM14 cells rapidly internalize CpG-anti-miR146aco even a low concentrations.

FIGS. 17A-17F) CpG-anti-miR155 treatment reduces miR-155 expression in human and mouse myeloid cells. Mouse RAW264.7 (macrophages) (FIG. 17A) and DC2.4 (dendritic cells) (FIG. 17B) as well as human MV4-11 AML cells (FIG. 17C) were incubated with 100 nM CpG-anti-miR155 or CpG-scrambled RNA (negative control) for 18 h and then treated with 1 vg/ml LPS for 4 h. KG1a (FIG. 17D), MOLM13 (FIG. 17E), and MOLM14 (FIG. 17F) cells were incubated with 100 nM CpG-anti-miR155 or CpG-scrambled RNA for 18 h. Mature miR-155 expression was measured using TAQMAN® qPCR assay and normalized to snoRNA234 levels. miR-155 expression level in untreated samples was set as 1.0. Data are shown as means±SEM (n=3). *P<0.05.

FIGS. 18A-18F) CpG-anti-miR125b treatment reduces miR-125b expression in various cell models. RAW264.7 (FIG. 18A), DC2.4 (FIG. 18B), and MV4-11 (FIG. 18C) cells were incubated with 100 nM CpG-anti-miR125b or CpG-scrambled RNA (negative control) for 18 h and then treated with 1 vg/mILPS for 4 h. Human AML cells—KG1a (FIG. 18D), MOLM13 (FIG. 18E), and MOLM14 (FIG. 18F)—were incubated with 100 nM CpG-anti-miR125b or control CpG-scrambled RNA for 18 h. Mature miR-125b expression was measured using TAQMAN® qPCR assay and normalized to snoRNA234 levels. miR-125b expression level in untreated samples was set as 1.0. Data are shown as means±SEM (n=3). *P<0.05.

FIGS. 19A-19H. Inhibitory effects of CpG-anti-miR146a. FIGS. 19A-19F) CpG-anti-miR146a treatment reduces miR-146a expression in human and mouse myeloid cells. Mouse RAW264.7 (macrophages) (FIG. 19A) and DC2.4 (dendritic cells) (FIG. 19B) as well as human MV4-11 (FIG. 19C) and KG1a AML (FIG. 19D) cells were incubated with 100 nM CpG-anti-miR146a or CpG-scrambled RNA (negative control) for 18 h and then treated with 1 vg/ml LPS for 4 h. KG1a, MOLM13 (FIG. 19E), and MOLM14 (FIG. 19F) cells were incubated with 100 nM CpG-anti-miR146a or CpG-scrambled RNA for 18 h. FIGS. 19G-19H) Mouse CMM AML cells (FIG. 19G) and A20 lymphoma cells (FIG. 19H) were incubated with 100 nM CpG-miR146a mimic for 18 h. Mature miR-146a expression was measured using TAQMAN® qPCR assay and normalized to snoRNA234 levels. miR-146a expression level in untreated samples was set as 1.0. Data are shown as means±SEM (n=3). *P<0.05.

FIGS. 20A-20C) CpG-anti-miRs regulate downstream targets of miR155, miR125b, and miR146a. Mouse RAW264.7 or human MV4-11 cells were incubated with 250 nM or 500 nM of CpG-anti-miR155, CpG-anti-miR125b, or CpG-anti-miR146a, or 500 nM of CpG-scramble for 48 h, then the cell lysates were collected and electrophoresed and immunoblotted by antibodies against SHIP1 (miR155 target) (FIG. 20A), IRF4 (miR125b target) (FIG. 20B), or IRAK1 (miR146a target) (FIG. 20C). The band intensities were normalized against β-actin and quantified. Fold induction over the control protein levels are indicated below the blot. FIG. 20D) MV4-11 cells were incubated with 500 nM of CpG-anti-miR155, CpG-antimiR125b, CpG-anti-miR146a, or CpG-scramble for 24 h, then cell lysates were collected and electrophoresed and immunoblotted to detect activated caspase 3 indicating induction of apoptosis.

FIGS. 21A-21D) CpG-anti-miR155, GpC-anti-miR155, CpG-anti-miR146a, and GpC-anti-miR146a treatment reduces miR155 or miR-146a expression in RAW264.7 (FIGS. 21A,21C) and A20 cells (FIGS. 21B,21D). The cells were incubated with 100 nM CpG-anti-miRs or GpC-anti-miRs for 18 hrs. FIGS. 21E-21H) CpG-anti-miRs and GpC-anti-miRs treatment regulates downstream targets of miR155 and miR146a. RAW264.7 (FIGS. 21E,21G) or A20 cells (FIGS. 21F,21H) were incubated with 500 nM of CpG-anti-miR155, GpC-anti-miR155, or CpG-anti-miR146a, GpC-anti-miR146a for 48 hrs, then the cell lysates were collected and immunoblotted using antibodies against SHIP1 (miR155 target) or IRAK1 (miR146a target)

FIGS. 22A-22B) CpG-miR146a mimic increases miR-146a expression in cultured CMM leukemia (FIG. 22A) and A20 lymphoma cells (FIG. 22B). Cells were incubated with 100 nM CpG-miR146a mimic for 18 h. FIG. 22C) CpG-miR146a mimic inhibits IRAK1 expression, a downstream target of miR146a. A20 cells were incubated with 500 nM of CpG-miR146a mimic or LPS (used as a positive control) for 48 h, then the cell lysates were collected and immunoblotted using IRAK1-specific antibodies. FIGS. 22D-22E) RAW-Blue cells, expressing NF-KB-responsive reporter gene, were treated with 500 nM of CpG-miR146a mimic for 24 h and then with 1 pg/ml LPS for another 24 h. Culture medium was collected and analyzed for NF-KB activity using the Quanti-Blue assay kit (FIG. 22D) for IL-6 levels in media using ELISA (FIG. 22E).

FIGS. 24A-24I. Knockdown of miR-126 by CpG-miR-126 inhibitor enhances elimination of mouse CML LSC in combination with NIL in vivo. BM cells from SCL-tTA/BCR-ABL mice (CD45.2) were transplanted into congenic B6 mice (CD45.1, n=40) to generate a cohort of mice with CML-like disease. Following confirmation of CML development at 4 weeks after transplantation, mice were randomly divided into 4 groups (n=10 each) and treated with CpG-miR-126 inhibitor (5 mg/kg i.v.4 times a week), CpG-scrRNA (5 mg/kg, i.v. 4 times a week), CpG-miR-126 inhibitor plus NIL (50 mg/kg, daily by gavage), and CpG-scrRNA plus NIL for 3 weeks. Percentage of donor CML cells in peripheral blood (PB) (FIG. 24A), spleen (FIG. 24B) and bone marrow (BM) (FIG. 24C), numbers of donor CML LSK in spleen (FIG. 24D) and BM (FIG. 24E), and numbers of donor CML long term hematopoietic stem cells (LTHSC) in spleen (FIG. 24F) and BM (FIG. 24G) after 3 weeks' treatment were measured. Another cohort of mice was treated for 3 weeks and then followed for survival studies after 3 weeks of treatment (n=10 in each group) (FIG. 24H). BM cells (CD45.2) from treated leukemic mice (3 weeks) were pooled, and $4\times10^6$, $2\times10^6$, $1\times10^6$, and $5\times10^5$ cells/mouse were transplanted into secondary congenic CD45.1 recipient mice irradiated at 900cGy (n=6 mice/dose/condition×4 doses×4 conditions=96 mice). The recipient mice were monitored for 16 weeks for CML cell engraftment in blood and leukemia development by WBC count. Frequency of LIC was quantified using L-Calc software (FIG. 24I). Abbreviations: NIL (Nilotinib); PB (peripheral blood); BM (bone marrow); LTHSC (long term hematopoietic stem cells); LIC (leukemia-initiating cells); LSK (lineage: Sca-1+c-kit+ cells).

FIGS. 26A-26E. Effective knockdown of miR-126 with miR-126 inhibitors conjugated with CpG, GpC and PS, and effective over-expression with miR-126 mimics in K562 and MV4-11 cells. K562 and MV4-11 cells were treated with miR-126 inhibitors conjugated with CpG, GpC, PS (FIGS. 26A-26B) or miR-126 mimics (615, 616 and 617) (FIGS. 26C-26D) (500 nM) for 24 hours, and miR-126 expression was measured in these cells. We showed here that CpG motif can be omitted in the targeting ODN sequence. GpC and completely PS-modified oligo also succeeds in blocking miR126. Incubation with miR-126 mimics, especially GM617, significantly increased miR-126 expression in K562 and MV4-11 cells. Just like CpG-miR-126 inhibitor which is very effective in reducing miR-126 in cells, we also designed miR-126 mimics, which are very effective in increasing miR-126 levels in cells without using any transduction reagents. FIG. 26E) Tabulation of sequence set forth herein.

DETAILED DESCRIPTION OF THE DISCLOSURE

Figure 2A:
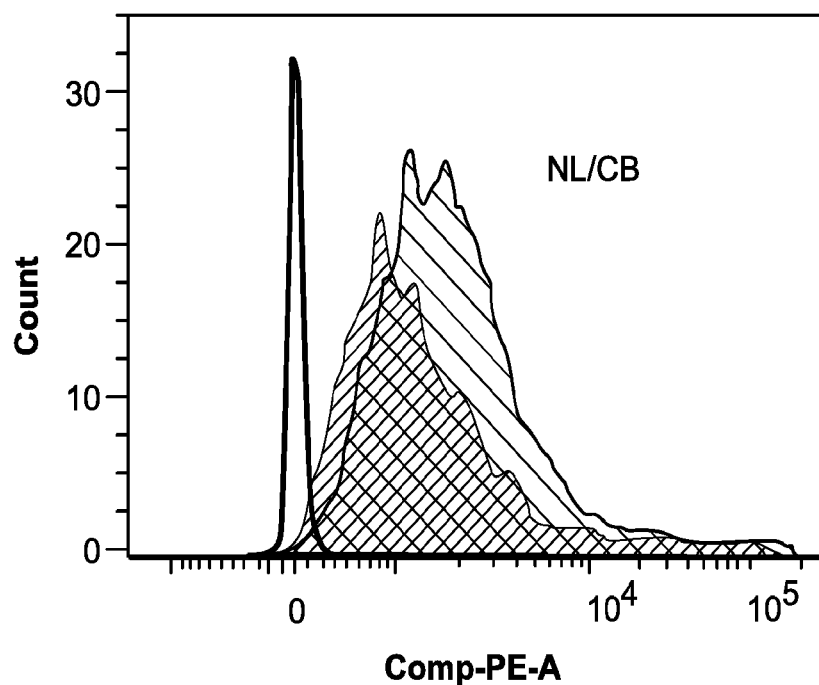
FIGS. 2A-2D are flow cytometry histograms showing results of uptake tests in normal, cord blood, acute myeloid leukemia (AML), and chronic myeloid leukemia (CML) CD34+ cells. Normal (NL), cord blood (CB), AML and CML34+ cells were cultured with CpG-scramble RNA (500 nM) and CpG-miR126 inhibitor-Cy3 (500 nm) for 16 hours.
Figure 2B:
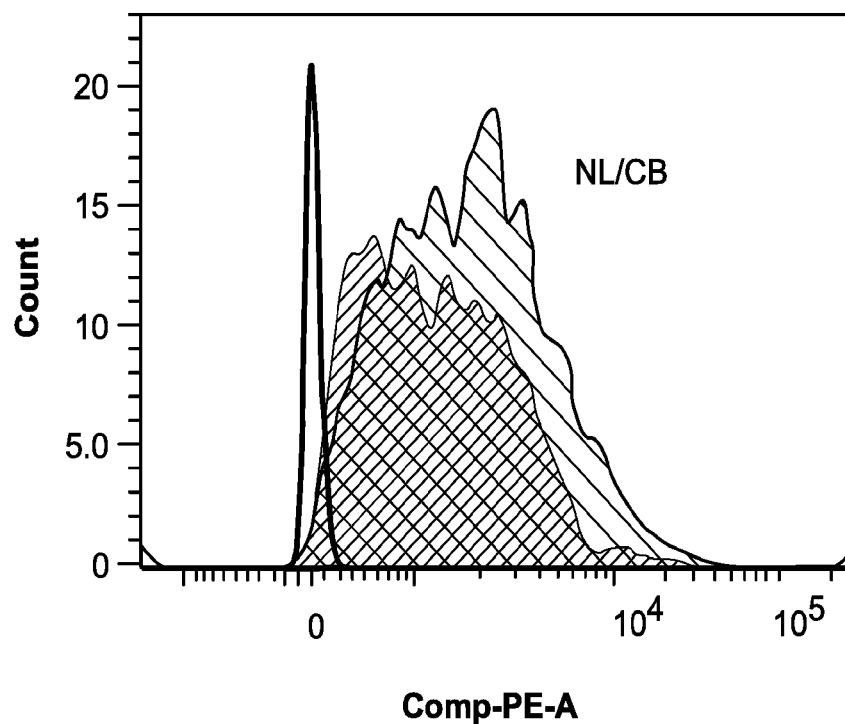
Figure 2C:
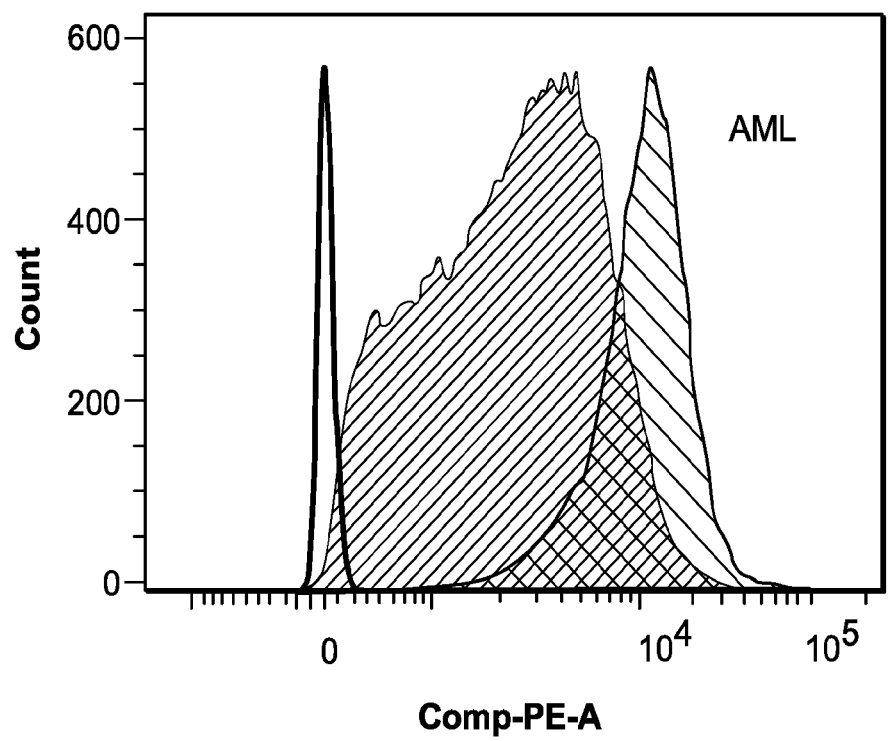
Figure 2D:
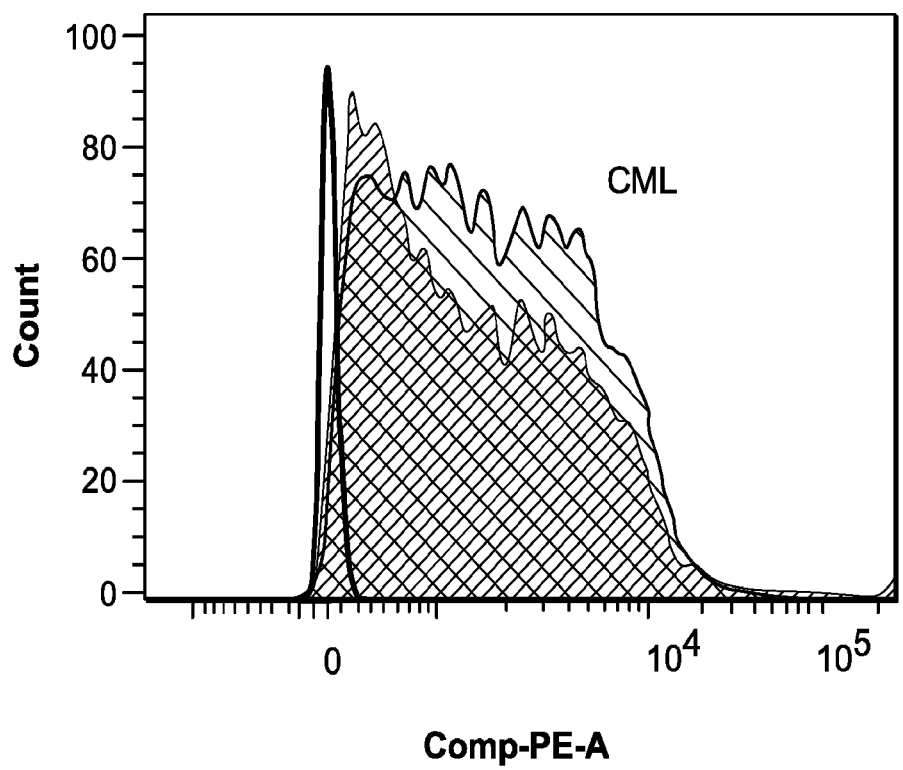

Provided herein, inter alia, a compound including a phosphorothioated CpG oligodeoxynucleotide (CpG-ODN), conjugated to an anti-microRNA (anti-miR) or to a microRNA (miRNA)-mimic nucleic acid sequence (miRNA-mimic) or a compound including an anti-microRNA (anti-miR) sequence, where the anti-miR sequence contains one or more phosphorothioate linkages and one or more chemically modified nucleotides. In embodiments, the compound described herein promotes the internalization of anti-miRs and/or miRNA-mimic. In embodiments, the modifications/conjugates used herein facilitate the leaving of the compounds described herein from endosomes. In embodiments, the modifications/conjugates used herein stabilize the anti-miRs and/or miRNA-mimics used herein.

Definitions

The following definitions are included for the purpose of understanding the present subject matter and for constructing the appended patent claims. Abbreviations used herein have their conventional meaning within the chemical and biological arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this disclosure. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, noncovalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformicacid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Unless indicated otherwise, the following annotations are used in the nucleic acid sequences disclosed herein: *=phosphorothioate linkage; xxxxx=any linker described herein and in embodiments xxxxx may be $-(CH_2)_n-PO_4-$ $[(CH_2)_n-PO_4]_z-(CH_2)_n)$ bonded to phosphate groups at both ends except at the termini where terminal phosphates are optionally added and 5'x has an OH terminus and 3' x has a $-C^6-NH_2$ bonded to the final phosphate group, other linkages are phosphodiester; mN indicates a 2'OMe modified nucleotide; fN indicates a 2'fluoro modified nucleotide; and rN indicates a ribonucleotide.

As used herein, the term "anti-microRNA (anti-miR)" or "anti-microRNA (anti-miR) nucleic acid sequence" is used according to its plain and ordinary meaning and refers to RNA that is capable of suppressing or reducing expression and/or activity of a target microRNA. In embodiments, the anti-miR oligomer may be a single stranded oligomer of 20-30 bases. In embodiments, the anti-miR oligomer may be a double stranded oligomer of 20-30 bases. In embodiments, the anti-miR oligomer may be partially double stranded, with single stranded overhangs. In embodiments, the oligomer may have a 2'chemical modification. In embodiments, the oligomer may have serum stability-enhancing chemical modification, e.g., a phosphothioate internucleotide linkage, a 2'-O-methyl ribonucleotide, a 2'-deoxy-2'fluoro ribonucleotide, a 2'-deoxy ribonucleotide, a universal base nucleotide, a 5-C methyl nucleotide, an inverted deoxybasic residue incorporation, or a locked nucleic acid. In embodiments, an anti-miR sequence hybridizes to the corresponding miR sequence. Full complementarity is not necessarily required, provided there is sufficient complementarity to cause hybridization. In some embodiments, the degree of complementarity between an anti-miR sequence and its corresponding miR sequence, when optimally aligned using a suitable alignment algorithm, is about or more than about 50%, 60%, 75%, 80%, 85%, 90%, 91%, 92%, 93%, 94%, 95%, 96%, 97%, 98%, 99%, or 100%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In embodiments, the anti-miR sequence has at least 80%, 85%, 90%, 95%, 96%, 97%, 98%, 99% or 100% sequence identity with the perfectly complementary sequence of the target miR sequence.

A "microRNA," "microRNA nucleic acid sequence," "miR," "miRNA" as used herein, refers to a nucleic acid that functions in RNA silencing and post-transcriptional regulation of gene expression. The term includes all forms of a miRNA, such as the pri-, pre-, and mature forms of the miRNA. In embodiments, microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA. In embodiments, a miRNA nucleic acid sequence described herein is about 10 to 80 nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 nucleotides) in length. In embodiments, a miRNA nucleic acid sequence described herein is about 15 to 50 nucleotides (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides) in length. In embodiments, a miRNA nucleic acid sequence described herein is about 18 to 25 nucleotides (e.g., 18, 19, 20, 21, 22, 23, 24, 25 nucleotides) in length.

As used herein, the term "miR126" or "miR142 nucleic acid sequence" includes all forms of miR126 including the pri-, pre-, and mature forms of miR126, as well as variants, homologues, modifications, and derivatives thereof (e.g., within at least 50%, 80%, 90%, 95%, 96%, 97%, 98%, 99% or 100% activity compared to the native miR126). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR126 is the miRNA as identified by NCBI Reference Sequence: NR_029695.1 or sequence:

```
                                                 (SEQ ID NO: 37)
 1 cgctggcgac gggacattat tacttttggt acgcgctgtg acacttcaaa ctcgtaccgt 61 gagtaataat gcgccgtcca cggca.
```

The term "anti-miR126" or "anti-miR126 nucleic acid sequence" refers to a sequence that is at least 80%, 85%, 90%, 95%, 96%, 97%, 98%, 99% or 100% sequence identity with the perfectly complementary sequence to the target miR126 nucleic acid as defined above.

As used herein, the term "miR142" or "miR142 nucleic acid sequence" includes all forms of miR142 including the pri-, pre-, and mature forms of miR142, as well as variants, homologues, modifications, and derivatives thereof (e.g., within at least 50%, 80%, 90%, 95%, 96%, 97%, 98%, 99% or 100% activity compared to the native miR142). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR142 is the miRNA as identified by NCBI Reference Sequence: NR_029683.1 or sequence:

```
                                                 (SEQ ID NO: 38)
 1 gacagtgcag tcacccataa agtagaaagc actactaaca gcactggagg gtgtagtgtt 61 tcctacttta tggatgagtg tactgtg.
```

The term "anti-miR142" or "anti-miR142 nucleic acid sequence" refers to a sequence that is at least 80%, 85%, 90%, 95%, 96%, 97%, 98%, 99% or 100% sequence identity with the perfectly complementary sequence to the target miR142 nucleic acid as defined above.

As used herein, the term "miR155" or "miR155 nucleic acid sequence" includes all forms of miR155 including the pri-, pre-, and mature forms of miR155, as well as variants, homologues, modifications, and derivatives thereof (e.g., within at least 50%, 80%, 90%, 95%, 96%, 97%, 98%, 99% or 100% activity compared to the native miR155). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR155 is the miRNA as identified by NCBI Reference Sequence: NR_030784.1 or sequence:

```
                                                 (SEQ ID NO: 39)
 1 ctgttaatgc taatcgtgat aggggttttt gcctccaact gactcctaca tattagcatt 61 aacag.
```

The term "anti-miR155" or "anti-miR155 nucleic acid sequence" refers to a sequence that is at least 80%, 85%, 90%, 95%, 96%, 97%, 98%, 99% or 100% sequence identity with the perfectly complementary sequence to the target miR155 nucleic acid as defined above.

As used herein, the term "miR9" or "miR9 nucleic acid sequence" includes all forms of miR9 including the pri-, pre-, and mature forms of miR9, as well as variants, homologues, modifications, and derivatives thereof (e.g., within at least 50%, 80%, 90%, 95%, 96%, 97%, 98%, 99% or 100% activity compared to the native miR9). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR9 is the miRNA as identified by NCBI Reference Sequence: NR_029691.1, NCBI Reference Sequence: NR_029692.1 or sequences:

```
                                                  (SEQ ID NO: 40)
  1 cggggttggt tgttatcttt ggttatctag ctgtatgagt ggtgtggagt cttcataaag 61 ctagataacc gaaagtaaaa ataacccca;
```

```
                                                  (SEQ ID NO: 41)
  1 ggaggcccgt ttctctcttt ggttatctag ctgtatgagt gccacagagc cgtcataaag 61 ctagataacc gaaagtagaa atgattctca.
```

The term "anti-miR9" or "anti-miR9 nucleic acid sequence" refers to a sequence that is at least 80%, 85%, 90%, 95%, 96%, 97%, 98%, 99% or 100% sequence identity with the perfectly complementary sequence to the target miR9 nucleic acid as defined above.

As used herein, the term "miR10b" or "miR10b nucleic acid sequence" includes all forms of miR10b including the pri-, pre-, and mature forms of miR10b, as well as variants, homologues, modifications, and derivatives thereof (e.g., within at least 50%, 80%, 90%, 95%, 96%, 97%, 98%, 99% or 100% activity compared to the native miR10b). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR10b is the miRNA as identified by NCBI Reference Sequence: NR_029609.1 or sequence:

```
                                                  (SEQ ID NO: 42)
  1 ccagaggttg taacgttgtc tatatatacc ctgtagaacc gaatttgtgt ggtatccgta 61 tagtcacaga ttcgattcta ggggaatata tggtcgatgc aaaaacttca.
```

The term "anti-miR10b" or "anti-miR10b nucleic acid sequence" refers to a sequence that is at least 80%, 85%, 90%, 95%, 96%, 97%, 98%, 99% or 100% sequence identity with the perfectly complementary sequence to the target miR10b nucleic acid as defined above.

As used herein, the term "miR21"" or "miR21 nucleic acid sequence" includes all forms of miR21 including the pri-, pre-, and mature forms of miR21, as well as variants, homologues, modifications, and derivatives thereof (e.g., within at least 50%, 80%, 90%, 95%, 96%, 97%, 98%, 99% or 100% activity compared to the native miR21). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR21 is the miRNA as identified by NCBI Reference Sequence: NR_029493.1 or sequence:

```
                                                      (SEQ ID NO: 43)
  1 tgtcgggtag cttatcagac tgatgttgac tgttgaatct catggcaaca ccagtcgatg 61 ggctgtctga ca.
```

The term "anti-miR21" or "anti-miR21 nucleic acid sequence" refers to a sequence that is at least 80%, 85%, 90%, 95%, 96%, 97%, 98%, 99% or 100% sequence identity with the perfectly complementary sequence to the target miR21 nucleic acid as defined above.

As used herein, the term "miR17" or "miR17 nucleic acid sequence" includes all forms of miR17 including the pri-, pre-, and mature forms of miR17, as well as variants, homologues, modifications, and derivatives thereof (e.g., within at least 50%, 80%, 90%, 95%, 96%, 97%, 98%, 99% or 100% activity compared to the native miR17). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR17 is the miRNA as identified by NCBI Reference Sequence: NR_029487.1 or sequence:

```
                                                      (SEQ ID NO: 44)
  1 gtcagaataa tgtcaaagtg cttacagtgc aggtagtgat atgtgcatct actgcagtga 61 aggcacttgt agcattatgg tgac.
```

The term "anti-miR17" or "anti-miR17 nucleic acid sequence" refers to a sequence that is at least 80%, 85%, 90%, 95%, 96%, 97%, 98%, 99% or 100% sequence identity with the perfectly complementary sequence to the target miR17 nucleic acid as defined above.

As used herein, the term "miR92" or "miR92 nucleic acid sequence" includes all forms of miR92 including the pri-, pre-, and mature forms of miR92, as well as variants, homologues, modifications, and derivatives thereof (e.g., within at least 50%, 80%, 90%, 95%, 96%, 97%, 98%, 99% or 100% activity compared to the native miR92). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR92 is the miRNA as identified by NCBI Reference Sequence: NR_029508.1 or sequence:

```
                                                      (SEQ ID NO: 45)
  1 ctttctacac aggttgggat cggttgcaat gctgtgtttc tgtatggtat tgcacttgtc 61 ccggcctgtt gagtttgg.
```

The term "anti-miR92" or "anti-miR92 nucleic acid sequence" refers to a sequence that is at least 80%, 85%, 90%, 95%, 96%, 97%, 98%, 99% or 100% sequence identity with the perfectly complementary sequence to the target miR92 nucleic acid as defined above.

As used herein, the term "miR125b" or "miR125b nucleic acid sequence" includes all forms of miR125b including the pri-, pre-, and mature forms of miR125b, as well as variants, homologues, modifications, and derivatives thereof (e.g., within at least 50%, 80%, 90%, 95%, 96%, 97%, 98%, 99% or 100% activity compared to the native miR125b). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR125b is the miRNA as identified by NCBI Reference Sequence: NR_029671.1 or sequence:

the 3'UTR unique to the target gene. Once introduced into cells, this RNA fragment, may mimic an endogenous miRNA, bind specifically to its target gene and produce posttranscriptional repression, more specifically translational inhibition, of the gene. Unlike endogenous miRNAs, miRNA-mimics may act in a gene-specific fashion. In embodiments, the miRNA-mimic may be a double stranded oligomer of 20-30 bases (e.g., 20, 21, 22, 23, 24, 25, 26, 27, 28, 29, 30 bases). In embodiments, the miRNA-mimic may be a triple stranded oligomer of 20-30 bases (e.g., 20, 21, 22, 23, 24, 25, 26, 27, 28, 29, 30 bases). In embodiments, the miRNA-mimic may have a 2'chemical modification. In embodiments, the miRNA-mimic may have serum stability-enhancing chemical modification, e.g., a phosphothioate internucleotide linkage, a 2'-O-methyl ribonucleotide, a 2'-deoxy-2'fluoro ribonucleotide, a 2'-deoxy ribonucleotide, a universal base nucleotide, a 5-C methyl nucleotide, an inverted deoxybasic residue incorporation, or a locked nucleic acid.

As used herein, the term "miR126-mimic" or "miR26-mimic nucleic acid sequence" refers to an oligonucleotide

```
                                                           (SEQ ID NO: 46)
  1 tgcgctcctc tcagtccctg agaccctaac ttgtgatgtt taccgtttaa atccacgggt 61 taggctcttg ggagctgcga gtcgtgct.
```

The term "anti-miR125b" or "anti-miR125b nucleic acid sequence" refers to a sequence that is at least 80%, 85%, 90%, 95%, 96%, 97%, 98%, 99% or 100% sequence identity with the perfectly complementary sequence to the target miR125b nucleic acid as defined above.

As used herein, the term "miR146a" or "miR146 nucleic acid sequence" includes all forms of miR146a including the pri-, pre-, and mature forms of miR146a, as well as variants, homologues, modifications, and derivatives thereof (e.g., within at least 50%, 80%, 90%, 95%, 96%, 97%, 98%, 99% or 100% activity compared to the native miR146a). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR146a is the miRNA as identified by NCBI Reference Sequence: NR_029701.1 or sequence:

that is structurally substantially similar to miR126 and is capable of effecting a biological function similar to miR126. In embodiments, the miR126-mimic has at least 50%, 80%, 90%, 95%, 96%, 97%, 98%, 99% or 100% activity compared to the native miR126. In embodiments, the miR126-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR126.

As used herein, the term "miR142-mimic" or "miR142-mimic nucleic acid sequence" refers to an oligonucleotide that is structurally substantially similar to miR142 and is capable of effecting a biological function similar to miR142. In embodiments, the miR142-mimic has at least 50%, 80%, 90%, 95%, 96%, 97%, 98%, 99% or 100% activity compared to the native miR142. In embodiments, the miR142-mimic has at least 50%, 80%, 85%, 90%, 91%, 92%, 93%, 94%, 95%, 96%, 97%, 98%, 99% or 100% sequence identity across the whole sequence or a portion of the sequence (e.g.

```
                                                           (SEQ ID NO: 47)
  1 ccgatgtgta tcctcagctt tgagaactga attccatggg ttgtgtcagt gtcagacctc 61 tgaaattcag ttcttcagct gggatatctc tgtcatcgt.
```

The term "anti-miR146a" or "anti-miR146a nucleic acid sequence" refers to a sequence that is at least 80%, 85%, 90%, 95%, 96%, 97%, 98%, 99% or 100% sequence identity with the perfectly complementary sequence to the target miR146a nucleic acid as defined above.

As used herein, the term "microRNA-mimic (miRNA-mimic)" or "miRNA-mimic nucleic acid sequence" is used according to its plain and ordinary meaning and refers to single, double or triple stranded oligonucleotide that is capable of effecting a biological function similar to a micro-RNA. In embodiments, miRNA-mimic may be non-natural double-stranded miR-like RNA fragments. Such an RNA fragment may be designed to have its 5'-end bearing a partially complementary motif to the selected sequence in a 10, 15, 20, 25, 30, 40, 45, 50, 55, 60, 65, 70, 75, or 80 continuous nucleotides portion) compared to native miR142.

As used herein, the term "miR155-mimic" or "miR155-mimic nucleic acid sequence" refers to an oligonucleotide that is structurally substantially similar to miR155 and is capable of effecting a biological function similar to miR155. In embodiments, the miR155-mimic has at least 50%, 80%, 90%, 95%, 96%, 97%, 98%, 99% or 100% activity compared to the native miR155. In embodiments, the miR155-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR155.

As used herein, the term "miR9-mimic" or "miR9-mimic nucleic acid sequence" refers to an oligonucleotide that is structurally substantially similar to miR9 and is capable of effecting a biological function similar to miR9. In embodiments, the miR9-mimic has at least 50%, 80%, 90%, 95%, 96%, 97%, 98%, 99% or 100% activity compared to the native miR9. In embodiments, the miR9-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR9.

As used herein, the term "miR10b-mimic" or "miR10b-mimic nucleic acid sequence" refers to an oligonucleotide that is structurally substantially similar to miR10b and is capable of effecting a biological function similar to miR10b. In embodiments, the miR10b-mimic has at least 50%, 80%, 90%, 95%, 96%, 97%, 98%, 99% or 100% activity compared to the native miR10b. In embodiments, the miR10b-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR10b.

As used herein, the term "miR21-mimic" or "miR21-mimic nucleic acid sequence" refers to an oligonucleotide that is structurally substantially similar to miR21 and is capable of effecting a biological function similar to miR21. In embodiments, the miR21-mimic has at least 50%, 80%, 90%, 95%, 96%, 97%, 98%, 99% or 100% activity compared to the native miR21. In embodiments, the miR21-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR21.

As used herein, the term "miR17-mimic" or "miR17-mimic nucleic acid sequence" refers to an oligonucleotide that is structurally substantially similar to miR17 and is capable of effecting a biological function similar to miR17. In embodiments, the miR17-mimic has at least 50%, 80%, 90%, 95%, 96%, 97%, 98%, 99% or 100% activity compared to the native miR17. In embodiments, the miR17-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR17.

As used herein, the term "miR92-mimic" or "miR92-mimic nucleic acid sequence" refers to an oligonucleotide that is structurally substantially similar to miR92 and is capable of effecting a biological function similar to miR92. In embodiments, the miR92-mimic has at least 50%, 80%, 90%, 95%, 96%, 97%, 98%, 99% or 100% activity compared to the native miR92. In embodiments, the miR92-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR92.

As used herein, the term "miR125b-mimic" or "miR125b-mimic nucleic acid sequence" refers to an oligonucleotide that is structurally substantially similar to miR125b and is capable of effecting a biological function similar to miR125b. In embodiments, the miR125b-mimic has at least 50%, 80%, 90%, 95%, 96%, 97%, 98%, 99% or 100% activity compared to the native miR125b. In embodiments, the miR125b-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR125b.

As used herein, the term "miR146a-mimic" or "miR146a-mimic nucleic acid sequence" refers to an oligonucleotide that is structurally substantially similar to miR146a and is capable of effecting a biological function similar to miR146a. In embodiments, the miR146a-mimic has at least 50%, 80%, 90%, 95%, 96%, 97%, 98%, 99% or 100% activity compared to the native miR146a. In embodiments, the miR146a-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR146a.

As used herein, the term "phosphorothioated oligodeoxynucleotide (ODN)" refers to a nucleic acid sequence, e.g., "CpG nucleic acid sequence" or "GpC nucleic acid sequence", in which some or all the internucleotide linkages constitute a phosphorothioate linkage. In embodiments, phosphorothioated oligodeoxynucleotide (ODN) is 15 to 30 bases long, single-stranded, partly or completely phosphorothioated. The partly phosphorothioated ODN is an ODN in which 1, 2, 3, 4, 5, 6, 7, 8, 9, 10, 11, 12, 13, 14, 15, 16, 17, 18, 19, 20, 21, 22, 23, 24, 25, 26, 27, or 28, internucleotide linkages constitute a phosphorothioate linkage.

In embodiments, the term "CpG motif" in a nucleic acid refers to a nucleic acid in which a 5' C nucleotide connected to a 3' G nucleotide through a phosphodiester internucleotide linkage or a phosphodiester derivative internucleotide linkage. In embodiments, the term "CpG motif" in a nucleic acid refers to a nucleic acid in which a 5' G nucleotide connected to a 3' C nucleotide through a phosphodiester internucleotide linkage or a phosphodiester derivative internucleotide linkage (aka a "GpC nucleic acid sequence). In embodiments, a CpG motif includes a phosphodiester internucleotide linkage. In embodiments, a CpG motif includes a phosphodiester derivative internucleotide linkage. In embodiments, a CpG motif includes a phosphorothioate linkage.

As used herein, the term "Class A CpG ODN" or "A-class CpG ODN" or "D-type CpG ODN" or "Class A CpG DNA sequence" is used in accordance with its common meaning in the biological and chemical sciences and refers to a CpG motif including oligodeoxynucleotide including one or more of poly-G sequence at the 5', 3', or both ends; an internal palindrome sequence including CpG motif; or one or more phosphodiester derivatives linking deoxynucleotides. In embodiments, a Class A CpG ODN includes poly-G sequence at the 5', 3', or both ends; an internal palindrome sequence including CpG motif; and one or more phosphodiester derivatives linking deoxynucleotides. In embodiments, the phosphodiester derivative is phosphorothioate. Examples of Class A CpG ODNs include ODN D19, ODN 1585, ODN 2216, and ODN 2336.

As used herein, the term "Class B CpG ODN" or "B-class CpG ODN" or "K-type CpG ODN" or "Class B CpG DNA sequence" is used in accordance with its common meaning in the biological and chemical sciences and refers to a CpG motif including oligodeoxynucleotide including one or more of a 6 mer motif including a CpG motif; phosphodiester derivatives linking all deoxynucleotides. In embodiments, a 6 mer motif comprises 5'-PuPyCGPyPu-3' (SEQ ID NO: 15), where Pu represents a purine containing nucleobase (e.g., A or G) and Py represents a pyrimidine containing nucleobase (e.g., T/U or C). In embodiments, a Class B CpG ODN includes one or more copies of a 6 mer motif including a CpG motif and phosphodiester derivatives linking all deoxynucleotides. In embodiments, the phosphodiester derivative is phosphorothioate. In embodiments, a Class B CpG ODN includes one 6 mer motif including a CpG motif. In embodiments, a Class B CpG ODN includes two copies of a 6 mer motif including a CpG motif. In embodiments, a Class B CpG ODN includes three copies of a 6 mer motif including a CpG motif. In embodiments, a Class B CpG ODN includes four copies of a 6 mer motif including a CpG motif. Examples of Class B CpG ODNs include ODN 1668, ODN 1826, ODN 2006, and ODN 2007.

As used herein, the term "Class C CpG ODN" or "C-class CpG ODN'" or "C-type CpG DNA sequence" is used in accordance with its common meaning in the biological and chemical sciences and refers to an oligodeoxynucleotide including a palindrome sequence including a CpG motif and phosphodiester derivatives (phosphorothioate) linking all deoxynucleotides. Examples of Class C CpG ODNs include ODN 2395 and ODN M362.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SW, and/or —SO$_2$W. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NR$SO_2$R', NR'NR"R''', —ONR'R", —NR'C=(O)NR"NR'''R'''', —CN, —$NO_2$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR, —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR''', —NR—C(NR'R")=NR''', —S(O)R', —S(O)$_2$R', —S(O)$_2$NR'R", —NR$SO_2$R', —NR'NR"R''', —ONR'R", —NR'C=(O)NR"NR'''R'''', —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R"')$_d$—, where s and d are independently integers of from 0 to 3, and X' is —O—, —NR—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

As used herein, the term "conjugated" when referring to two moieties means the two moieties are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der waal's bond(s)/interactions, hydrogen bond(s), polar bond(s), or combinations or mixtures thereof).

A "label" or a "detectable moiety" is a composition detectable by spectroscopic, photochemical, biochemical, immunochemical, chemical, magnetic resonance imaging, or other physical means. For example, useful detectable moieties include $^{32}P$, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline SPIO, monochrystalline SPIO aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable moieties also include any of the above compositions encapsulated in nanoparticles, particles, aggregates, coated with additional compositions, derivatized for binding to a targeting agent (e.g., compound described herein). Any method known in the art for conjugating an oligonucleotide or protein to the label may be employed, e.g., using methods described in Hermanson, Bioconjugate Techniques 1996, Academic Press, Inc., San Diego.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. The term "cell" as used herein also refers to individual cells, cell lines, or cultures derived from such cells. A "culture" refers to a composition comprising isolated cells of the same or a different type.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) nucleic acid sequence identity is defined as the percentage of nucleotides in a candidate sequence that are identical to the nucleotides in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self 17 hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

"Patient," "subject," "patient in need thereof," and "subject in need thereof" are herein used interchangeably and refer to a living organism suffering from or prone to a disease or condition that can be treated by administration using the methods and compositions provided herein. Non-limiting examples include humans, other mammals, bovines, rats, mice, dogs, monkeys, goat, sheep, cows, deer, and other non-mammalian animals. In some embodiments, a patient is human. Tissues, cells and their progeny of a biological entity obtained in vitro or cultured in vitro are also contemplated.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

The term "inhibiting" also means reducing an effect (disease state or expression level of a gene/protein/mRNA)

relative to the state in the absence of a compound or composition of the present disclosure.

A "test compound" as used herein refers to an experimental compound used in a screening process to identify activity, non-activity, or other modulation of a particularized biological target or pathway.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Disease" or "condition" refer to a state of being or health status of a patient or subject capable of being treated with the compounds or methods provided herein. In some instances, "disease" or "condition" refers to a "cancer".

As used herein, the term "cancer" refers to all types of cancer, neoplasm, malignant or benign tumors found in mammals, including leukemia, carcinomas and sarcomas. Exemplary cancers include breast cancer, ovarian cancer, colon cancer, liver cancer, kidney cancer and pancreatic cancer. Additional examples include leukemia (e.g., acute myeloid leukemia ("AML") or chronic myeloid leukemia ("CML")), cancer of the brain, lung cancer, non-small cell lung cancer, melanoma, sarcomas, and prostate cancer, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas.

An autoimmune disease refers to a disease in which the body's immune system attacks healthy cells. Examples of autoimmune diseases include, but are not limited to, rheumatoid arthritis, psoriasis, systemic lupus erythematosus (SLE), type II diabetes, non-alcoholic fatty liver disease, non-alcoholic steatohepatitis, multiple sclerosis (MS), Parkinson's disease (PD, Alzheimer's disease (AD) and inflammatory bowel disease (IBD).

An infectious disease refers to a medical condition caused by the growth and spread of harmful organisms (e.g., bacteria, viruses, fungi or parasites) within the body. Examples of infectious diseases include, but are not limited to, tuberculosis, influenza, Ebola, HIV, HPV infection and hepatitis.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture. In some embodiments contacting includes allowing a compound described herein to interact with a protein or enzyme.

The terms "phenotype" and "phenotypic" as used herein refer to an organism's observable characteristics such as onset or progression of disease symptoms, biochemical properties, or physiological properties.

The word "expression" or "expressed" as used herein in reference to a DNA nucleic acid sequence (e.g., a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual,* 18.1-18.88). When used in reference to polypeptides, expression includes any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

For specific proteins described herein (e.g., CD34 or CD38), the named protein includes any of the protein's naturally occurring forms, variants or homologs (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "CD34" refers to hematopoietic progenitor cell antigen CD34 also known as CD34 antigen that is encoded by the CD34 gene in humans. It is a cell surface glycoprotein and functions as a cell-cell adhesion factor. The term "CD34" as provided herein includes any of the CD34 protein naturally occurring forms, homologs or variants that maintain the activity of CD34 (e.g., within at least 50%, 80%, 90%, 95%, 96%, 97%, 98%, 99% or 100% activity compared to the native protein). In embodiments, variants or homologs have at least 50%, 80%, 85%, 90%, 91%, 92%, 93%, 94%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD34 protein is the protein as identified by the NCBI sequence reference NP_001764 or NP_001020280.1, homolog or functional fragment thereof.

The term "CD38" refers to cluster of differentiation 38, also known as cyclic ADP ribose hydrolase that is encoded by the CD38 gene in humans. It is a cell surface glycoprotein and functions in cell-cell adhesion and signaling transduction. The term "CD38" as provided herein includes any of the CD38 protein naturally occurring forms, homologs or variants that maintain the activity of CD38 (e.g., within at least 50%, 80%, 90%, 95%, 96%, 97%, 98%, 99% or 100% activity compared to the native protein). In embodiments, variants or homologs have at least 50%, 80%, 85%, 90%, 91%, 92%, 93%, 94%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD38 protein is the protein as identified by the NCBI sequence reference NP_001766.2, homolog or functional fragment thereof The term "an amount of" in reference to a polynucleotide or polypeptide, refers to an amount at which a component or element is detected. The amount may be measured against a control, for example, wherein an increased level of a particular polynucleotide or polypeptide in relation to the control, demonstrates enrichment of the polynucleotide or polypeptide. Thus, in embodiments, an increased amount indicates a greater level or efficiency of grafting HSPCs described herein into a host (e.g., mouse). The term refers to quantitative measurement of the enrichment as well as qualitative measurement of an increase or decrease relative to a control.

Throughout the description and claims of this specification the word "comprise" and other forms of the word, such as "comprising" and "comprises," means including but not limited to, and is not intended to exclude, for example, other components.

"Analog," "analogue," or "derivative" is used in accordance with its plain ordinary meaning within Chemistry and Biology and refers to a chemical agent that is structurally similar to another agent (i.e., a so-called "reference" agent) but differs in composition, e.g., in the replacement of one atom by an atom of a different element, or in the presence of a particular functional group, or the replacement of one functional group by another functional group, or the absolute stereochemistry of a chiral center of the reference agent. In some embodiments, a derivative may be a conjugate with a pharmaceutically acceptable agent, for example, phosphate or phosphonate.

As used herein, the term "salt" refers to acid or base salts of the agents used herein. Illustrative but non-limiting examples of acceptable salts are mineral acid (hydrochloric acid, hydrobromic acid, phosphoric acid, sulfuric acid, and the like) salts, organic acid (acetic acid, propionic acid, glutamic acid, citric acid, and the like) salts, and quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

An "adjuvant" (from Latin, adiuvare: to aid) is a pharmacological and/or immunological agent that modifies the effect of other agents.

A "diluent" (also referred to as a filler, dilutant or thinner) is a diluting agent. Certain fluids are too viscous to be pumped easily or too dense to flow from one particular point to the other. This can be problematic, because it might not be economically feasible to transport such fluids in this state. To ease this restricted movement, diluents are added. This decreases the viscosity of the fluids, thereby also decreasing the pumping/transportation costs.

The terms "administration" or "administering" refer to the act of providing an agent of the current embodiments or pharmaceutical composition including an agent of the current embodiments to the individual in need of treatment.

By "co-administer" it is meant that a composition described herein is administered at the same time, just prior to, or just after the administration of additional therapies. The compound or the composition of the disclosure can be administered alone or can be co-administered to the patient. Co-administration is meant to include simultaneous or sequential administration of the compound individually or in combination (more than one compound or agent). The preparations can also be combined, when desired, with other active substances (e.g. to reduce metabolic degradation).

As used herein, "sequential administration" includes that the administration of two agents (e.g., the compounds or compositions described herein) occurs separately on the same day or do not occur on a same day (e.g., occurs on consecutive days).

As used herein, "concurrent administration" includes overlapping in duration at least in part. For example, when two agents (e.g., any of the agents or class of agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and. Other modes of delivery include, but are not limited to, the use of liposomal formulations, intravenous infusion, transdermal patches, etc.

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Bioniater Sci. Polym. Ed.* 7:623-645, 1995; as biodegradable and injectable gel formulations (see, e.g., Gao *Phann. Res.* 12:857-863, 1995); or, as microspheres for oral administration (see, e.g., Eyles, *J. Phann. Pharmacol.* 49:669-674, 1997).

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compositions/formulations of this disclosure can be administered as frequently as necessary to achieve a therapeutic amount.

Pharmaceutical compositions may include compositions wherein the therapeutic drug (e.g., agents described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of therapeutic drug effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and agents of this disclosure. Adjustment and manipulation of established dosages (e.g., frequency and duration) are well within the ability of those skilled in the art.

For any therapeutic agent described herein, the therapeutically effective amount can be initially determined from cell culture assays. Target concentrations will be those concentrations of therapeutic drug(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring agent's effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the therapeutic drug being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the agent. Thereafter, the dosage is increased by small increments until the optimum effect under circumstances is reached. Dosage amounts and intervals can be adjusted individually to provide levels of the administered agent effective for the particular clinical indication being treated. This will provide a therapeutic regimen that is commensurate with the severity of the individual's disease state.

A weight percent of a component, unless specifically stated to the contrary, is based on the total weight of the formulation or composition in which the component is included.

"Excipient" is used herein to include any other agent that may be contained in or combined with a disclosed agent, in which the excipient is not a therapeutically or biologically active agent/agent. As such, an excipient should be pharmaceutically or biologically acceptable or relevant (for example, an excipient should generally be non-toxic to the individual). "Excipient" includes a single such agent and is also intended to include a plurality of excipients. For the purposes of the present disclosure the term "excipient" and "carrier" are used interchangeably in some embodiments of the present disclosure and said terms are defined herein as, "ingredients which are used in the practice of formulating a safe and effective pharmaceutical composition."

The term "about" refers to any minimal alteration in the concentration or amount of an agent that does not change the efficacy of the agent in preparation of a formulation and in treatment of a disease or disorder. The term "about" with respect to concentration range of the agents (e.g., therapeutic/active agents) of the current disclosure also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Compound

In one aspect, provided herein is a compound including a phosphorothioated CpG oligodeoxynucleotide (CpG-ODN), conjugated to an anti-microRNA (anti-miR) or to a microRNA (miRNA)-mimic nucleic acid sequence (miRNA-mimic) In embodiments, the CpG-ODN is a 15 to 30 bases (nucleobases) long, single-stranded, partly or completely phosphorothioated oligodeoxynucleotide.

In one aspect, provided herein is a compound including an anti-microRNA (anti-miR) sequence, where the anti-miR sequence includes one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more), phosphorothioate linkages and one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) chemically modified nucleotides.

In embodiments, the compound includes a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with at least a 15 nucleobase continuous sequence of one of SEQ ID NOs: 1-14, conjugated to an anti-miR. In embodiments, the compound includes a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with one of SEQ ID NOs: 1-14, conjugated to an anti-miR. In embodiments, provided herein is a compound including a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with at least a 15 nucleobase continuous sequence of one of SEQ ID NOs: 1-14, conjugated to a miRNA-mimic. In embodiments, the compound includes a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with one of SEQ ID NOs: 1-14, conjugated to an miRNA-mimic. In embodiments, the nucleic acid sequence (CpG-ODN) is 15 to 30 (e.g., 15, 16, 17, 18, 19, 20, 21, 22, 23, 24, 25, 26, 27, 28, 29, or 30) bases long, single-stranded, partly or completely phosphorothioated oligonucleotide In embodiments, the compound of the present disclosure includes a nucleic acid sequence (CpG-ODN) having about 80-85%, about 85-90%, about 90-95%, about 95%-100% sequence identity with at least a 15 nucleobase continuous sequence of one of SEQ ID NOs: 1-14, conjugated an anti-miR or a miRNA-mimic. In embodiments, the compound of the present disclosure includes a nucleic acid sequence (CpG-ODN) having about 80-85%, about 85-90%, about 90-95%, about 95%-100% sequence identity with one of SEQ ID NOs: 1-14, conjugated an anti-miR or a miRNA-mimic. In embodiments, the nucleic acid sequence (CpG-ODN) is a 15 to 30 (e.g., 15, 16, 17, 18, 19, 20, 21, 22, 23, 24, 25, 26, 27, 28, 29, or 30) bases long, single-stranded, partly or completely phosphorothioated oligonucleotide.

In embodiments, the anti-miR is anti-miR126. In embodiments, the anti-miR is anti-miR155. In embodiments, the anti-miR is anti-R125b. In embodiments, the anti-miR is anti-miR146a. In embodiments, the anti-miR is anti-miR9. In embodiments, the anti-miR is anti-miR142. In embodiments, the anti-miR is anti-miR10b. In embodiments, the anti-miR is anti-miR21. In embodiments, the anti-miR is anti-miR17. In embodiments, the anti-miR is anti-miR92.

In embodiments, the miRNA-mimic is miR126-mimic. In embodiments, the miRNA-mimic is miR155-mimic. In embodiments, the miRNA-mimic is R125b-mimic. In embodiments, the miRNA-mimic is miR146a-mimic. In embodiments, the miRNA-mimic is miR9-mimic. In embodiments, the miRNA-mimic is miR142-mimic. In embodiments, the miRNA-mimic is miR10b-mimic. In embodiments, the miRNA-mimic is miR21-mimic. In embodiments, the miRNA-mimic is miR17-mimic. In embodiments, the miRNA-mimic is miR92-mimic.

The nucleic acid sequences (CpG-ODN) of SEQ ID NOs: 1-14 are listed in Table 1.

TABLE 1

Compound and component sequences.

| NAME | SEQUENCE 5'-3' (* = phosphorothioate linkage) | SEQ ID NO: |
|---|---|---|
| CpG(A)-ODN | G*G*TGCATCGATGCAGG*G*G*G*G | 1 |
| GpC(A)-ODN | G*G*T GCA TGC ATG CAG G*G*G*G*G | 2 |
| D19-PS | G*G*T*G*C*A*T*C*G*A*T*G*C*A*G*G*G*G*G | 3 |
| CpG(B)-ODN | T*C*C*A*T*G*A*C*G*T*T*C*C*T*G*A*T*G*C*T | 4 |
| ODN 1585 | G*G*GGTCAACGTTGAG*G*G*G*G*G or<br>G*GGGTCAACGTTGAG*G*G*G*G*G | 5 |
| ODN 2216 | G*G*GGGACGA:TCGTCG*G*G*G*G*G or<br>G*GGGGACGA:TCGTCG*G*G*G*G*G | 6 |
| ODN D19 | G*G*TGCATCGATGCAGG*G*G*G*G or<br>G*GTGCATCGATGCAGG*G*G*G*G | 7 |
| ODN 2336 | G*G*G*GACGAC:GTCGTGG*G*G*G*G*G or<br>G*G*GGACGAC:GTCGTGG*G*G*G*G*G | 8 |
| ODN 1668 | T*C*C*A*T*G*A*C*G*T*T*C*C*T*G*A*T*G*C*T | 9 |
| ODN 1826 | T*C*C*A*T*G*A*C*G*T*T*C*C*T*G*A*C*G*T*T | 10 |
| ODN 2006 (ODN7909) | T*C*G*T*C*G*T*T*T*T*G*T*C*G*T*T*T*T*G*T*C*G*T*T | 11 |
| ODN 2007 | T*C*G*T*C*G*T*T*G*T*C*G*T*T*T*T*G*T*C*G*T*T | 12 |
| ODN 2395 | T*C*G*T*C*G*T*T*T*T*C*G*G*C*G*C*G*C*G*C*C*G | 13 |
| ODN M362 | T*C*G*T*C*G*T*C*G*T*T*C*G*A*A*C*G*A*C*G*T*T*G*A*T | 14 |

In embodiments, the anti-miRNA sequence is an anti-miR126, anti-miR142, anti-miR155, anti-miR125b, anti-miR146a, anti-miR9, anti-miR10b, anti-miR17, anti-miR18, anti-miR19, anti-miR20, anti-miR21, anti-miR22, anti-miR23, anti-miR24, anti-miR25, anti-miR26, anti-miR27, anti-miR28, anti-miR29, anti-miR30, anti-miR31, anti-miR32, anti-miR33, anti-miR34, anti-miR35, anti-miR36, anti-miR37, anti-miR38, anti-miR39, anti-miR40, anti-miR41, anti-miR42, anti-miR43, anti-miR44, anti-miR45, anti-miR46, anti-miR47, anti-miR48, anti-miR49, anti-miR50, anti-miR51, anti-miR52, anti-miR53, anti-miR54, anti-miR55, anti-miR56, anti-miR57, anti-miR58, anti-miR59, anti-miR60, anti-miR61, anti-miR62, anti-miR63, anti-miR64, anti-miR65, anti-miR66, anti-miR67, anti-miR68, anti-miR69, anti-miR70, anti-miR71, anti-miR72, anti-miR73, anti-miR74, anti-miR75, anti-miR76, anti-miR77, anti-miR78, anti-miR79, anti-miR80, anti-miR81, anti-miR82, anti-miR83, anti-miR84, anti-miR85, anti-miR86, anti-miR87, anti-miR88, anti-miR89, anti-miR90, anti-miR91, or anti-miR92 nucleic acid sequence.

In embodiment, the mimic of the compound of the present disclosure is a miR126-mimic, miR142-mimic, miR155-mimic, miR125b-mimic, miR146a-mimic, miR9-mimic, miR10b-mimic, miR17-mimic, miR18-mimic, miR19-mimic, miR20-mimic, miR21-mimic, miR22-mimic, miR23-mimic, miR24-mimic, miR25-mimic, miR26-mimic, miR27-mimic, miR28-mimic, miR29-mimic, miR30-mimic, miR31-mimic, miR32-mimic, miR33-mimic, miR34-mimic, miR35-mimic, miR36-mimic, miR37-mimic, miR38-mimic, miR39-mimic, miR40-mimic, miR41-mimic, miR42-mimic, miR43-mimic, miR44-mimic, miR45-mimic, miR46-mimic, miR47-mimic, miR48-mimic, miR49-mimic, miR50-mimic, miR51-mimic, miR52-mimic, miR53-mimic, miR54-mimic, miR55-mimic, miR56-mimic, miR57-mimic, miR58-mimic, miR59-mimic, miR60-mimic, miR61-mimic, miR62-mimic, miR63-mimic, miR64-mimic, miR65-mimic, miR66-mimic, miR67-mimic, miR68-mimic, miR69-mimic, miR70-mimic, miR71-mimic, miR72-mimic, miR73-mimic, miR74-mimic, miR75-mimic, miR76-mimic, miR77-mimic, miR78-mimic, miR79-mimic, miR80-mimic, miR81-mimic, miR82-mimic, miR83-mimic, miR84-mimic, miR85-mimic, miR86-mimic, miR87-mimic, miR88-mimic, miR89-mimic, miR90-mimic, miR91-mimic, or miR92-mimic nucleic acid sequence.

In embodiments, provided herein is a compound linking CpG-ODN to an anti-miR126, which has the sequence: 5' G*G*T GCA TCG ATG CAGG*G*G* G*G (SEQ ID NO: 1) xxxxx CGC AUU AUU ACU CAC GGU ACG A (SEQ ID NO: 16) 3' and xxxxx indicates one or more linkers described herein. In embodiments, provided herein is a compound linking CpG-ODN to an anti-miR126, which has the sequence: 5' G*G*T GCA TCG ATG CAGG*G*G* G*G (SEQ ID NO: 1) xxxxx mCmGmC mAmUmU mAmUmU mAmCmU mCmAmC mGmGmU mAmCmG mA (SEQ ID NO: 17) 3', where xxxxx indicates one or more linkers described herein.

In embodiments, provided herein is a compound linking CpG-ODN to an anti-miR126, which has the sequence: 5' G*GT GCA TGC ATG CAG G*G*G*G*G (SEQ ID NO: 2) xxxxx CGC AUU AUU ACU CAC GGU ACG A (SEQ ID NO: 16) 3'. In embodiments, provided herein is a compound linking CpG-ODN to an anti-miR126, which has the sequence: 5' G*GT GCA TGC ATG CAG G*G*G*G*G (SEQ ID NO: 2) xxxxx mCmGmC mAmUmU mAmUmU mAmCmU mCmAmC mGmGmU mAmCmG mA (SEQ ID NO: 17) 3', where xxxxx indicates one or more linkers described herein.

In embodiments, provided herein is a compound linking CpG-ODN to an anti-miR126, which has the sequence: 5' G*G*T*G*C*A*T*C*G*A*T*G*C*A*G*G*G*G*G*G (SEQ ID NO: 3) xxxxx CGC AUU AUU ACU CAC GGU ACG A (SEQ ID NO: 16) 3'. In embodiments, provided herein is a compound linking CpG-ODN to an anti-miR126, which has the sequence: 5' G*G*T*G*C*A*T*C*G*A*T*G*C*A*G*G*G*G*G*G (SEQ ID NO: 3) xxxxx mCmGmC mAmUmU mAmUmU mAmCmU mCmAmC mGmGmU mAmCmG mA (SEQ ID NO: 17) 3', where xxxxx indicates one or more linkers described herein. In embodiments, provided herein is a compound linking CpG-ODN to an anti-miR126, which has the sequence: 5' G*G*T*G*C*A*T*C*G*A*T*G*C*A*G*G*G*G*G*G (SEQ ID NO: 3) xxxxx mC*mG*mC* mA*mU*mU* mA*mU*mU* mA*mC*mU* mC*mA*mC* mG*mG*mU* mA*mC*mG*mA (SEQ ID NO: 48) 3', where xxxxx indicates one or more linkers described herein.

Exemplary miR126 mimic sequences are listed in Table 2.

TABLE 2

| compounds including CpG-ODN linked to miR126 mimics | | | |
|---|---|---|---|
| CpG(D19)-<br>Sense miR126<br>unmodified | PS + 3<br>x | 5'-G*G*TGCATCGATGCAGG*G*G*G*G<br>xxxxx rUrCrG rUrArC rCrGrU rGrArG<br>rUrArA rUrArA rUrGrC rGrUrU-3' | SEQ ID NOS: 1, 18 |
| CpG(D19)-<br>Sense miR126<br>Fluoro<br>modified 2U<br>at 3' end | PS + 3<br>x<br>2'F | 5'-G*G*TGCATCGATGCAGG*G*G*G*G<br>xxxxx rUrCrG rUrArC rCrGrU<br>rGrArG rUrArA rUrArA rUGrC<br>rGfUfU-3' | SEQ ID NOS: 1, 19 |
| CpG D19-<br>Sense mir126<br>All pyrimidines<br>Fluoro modified | PS + 3<br>x<br>2'F | 5'-G*G*TGCATCGATGCAGG*G*G*G*G<br>xxxxx fUrAfC fCrGfU rGrArG<br>fUrArA fUrArA fUrGfC rGfUfU-3' | SEQ ID NOS: 1, 20 |
| Complementary<br>mir | | 5'-rCrGrC rArUrU rArUrU rArCrU<br>rCrArC rGrGrU rArCrG rA-3' | SEQ ID NO: 21 |

In the above sequences, xxxxx may be $-(CH_2)_n-PO_4-[(CH_2)n-PO_4]_z-(CH_2)_n$
*: phosphorothioation (One none-bridging oxygen replaced with sulfur)

In embodiments, the linker represented by "xxxxx" or the like described herein (e.g. in Tables 2, 3, and 4 (infra)) is a bond, substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, substituted (e.g. substituted with a substituent group, size-limited substituent group or lower substituent group) or unsubstituted cyclo-heteroalkylene or $-(CH_2)_n-PO_4-[(CH_2)_n-PO_4]_z-(CH_2)_n$, in which the symbol n is an integer from 1 to 5 (e.g., 3) and the symbol z is an integer from 0 to 50 (e.g. from 0 to 25, 0 to 10, or 0 to 5). In embodiments, n is 3 and z is 0 to 5 or 1 to 5. In embodiments, n is 3 and z is 0 to 4 or 1 to 4. In embodiments, n is 3 and z is 0 to 3 or 1 to 3. In embodiments, n is 3 and z is 3. 2' OMe (2'-O-Methylnucleoside; Hydroxyl in 2'-position replaced with 2'-OMethyl); PS is phoshorothioation. One none-bridging oxygen replaced with sulfur; PS+3 represents three phosphates in the sequence modified, had one none-bridging oxygen replaced with sulfur; PS+5 represents five phosphates in the sequence modified, had one none-bridging oxygen replaced with sulfur.

For example, as shown below, in embodiments, nucleobases in the phosphorothioated oligonucleotide of the present disclosure sequence may include a phosphorothioate internucleotide linkage. A portion of such a phosphorothioated oligonucleotide is shown below.

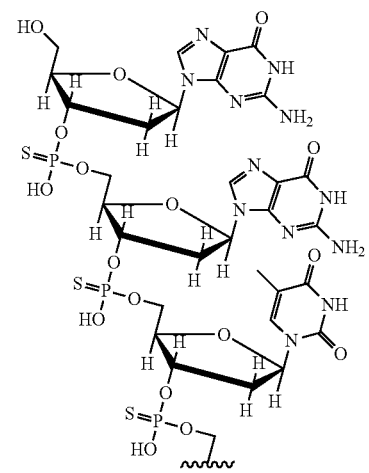

The linker may have the structure below, where the linker connects with the 3' phosphate of the guanine on one end and the 5' phosphate of the thymidine on the other end, and the nucleobases in the antisense part may be modified with 2'OMe.

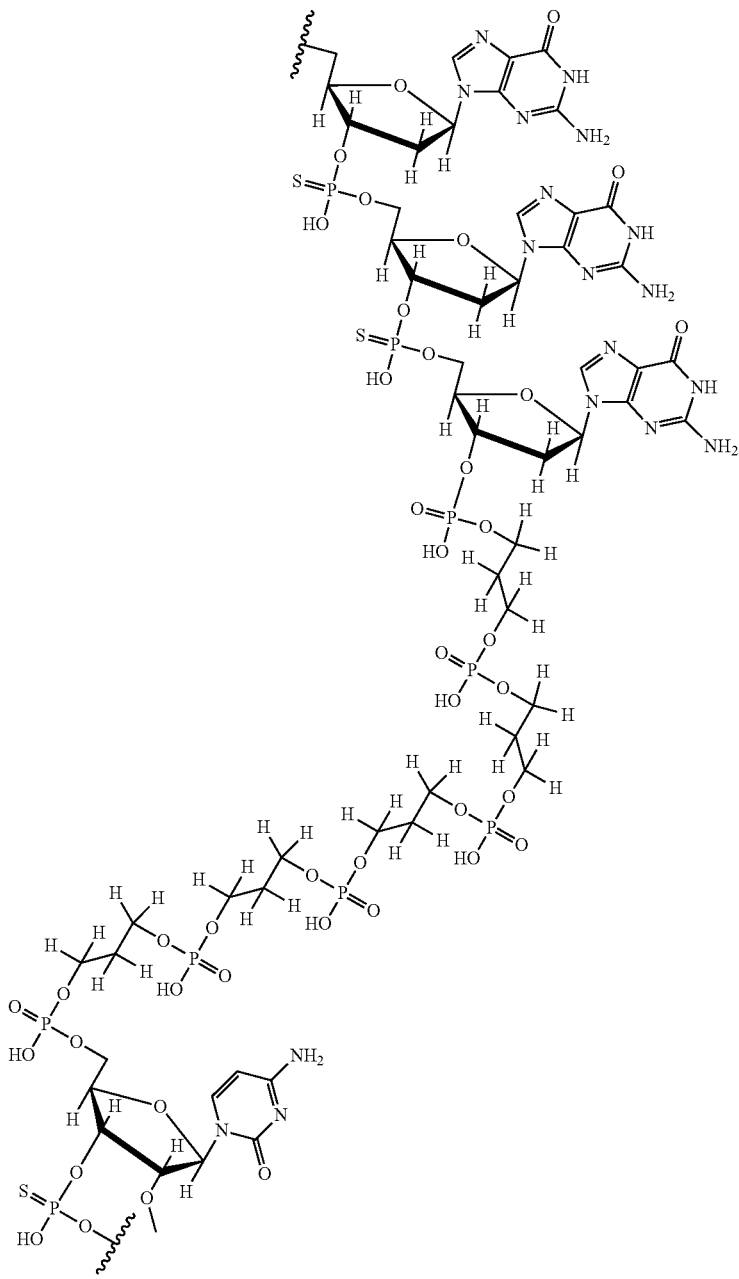

Five C3 Linkers

The above formula represents a portion of the CpG-ODN linked at the 3'-OH end with a (CH$_2$)$_3$ linker (also referred to herein as the C3 linker), which links to the 5'-phosphate of the anti-sense RNA.

The linker may be a bond, substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted or unsubstituted heteroarylene.

In embodiments, the present disclosure includes a composition linking phosphorothioated oligonucleotide of the present disclosure to an anti-miR142, which has the sequence: 5' G*G*T GCA TCG ATG CAGG*G*G* G*G (SEQ ID NO: 1) xxxxx UCCAUAAAGUAGGAAACAC-UACA (SEQ ID NO: 22)3'. The miR142 mimics are listed in Table 3:

TABLE 3

Compound and component sequences.

| NAME | SEQUENCE (* = phosphorothioate linkage), xxxxx may be -(CH$_2$)$_n$-PO$_4$-[(CH$_2$)$_n$-PO$_4$]$_z$-(CH$_2$)$_n$) bonded to phosphate groups at both ends except at the termini where terminal phosphates are optionally added and 5'x has an OH terminus and 3' x has a -C$^6$-NH$_2$ bonded to the final phosphate group, other linkages are phosphodiester. | SEQ ID NOS: |
|---|---|---|
| CpG D19-Sense miR142 unmodified | 5'-G*G*TGCATCGATGCAGG*G*G*G*G xxxx rUrGrU rArGrU rGrUrU rUrCrC rUrArC rUrUrU rArUrG rGrArUrU-3' | 1, 23 |
| CpG D12-Sense miR42 fluoro modified 2U at 3' end | 5'-G*G*TGCATCGATGCAGG*G*G*G*G xxxx rUrGrU rArGrU rGrUrU rUrCrC rUrArC rUrUrU rArUrG rGrAfUfU-3' | 1, 24 |
| Complementary mir | 5'-rUrCrC rArUrA rArArG rUrArG rGrArA rArCrA rCrUrA rCrA-3' | 24 |

In embodiments, provided herein is a composition linking CpG-ODN to an anti-miR155 having the sequence: 5' G*G*T GCA TCG ATG CAGG*G*G* G*G (SEQ ID NO: 1) xxxxx UGUUAAUGCUAAUAUGUAGGAG (SEQ ID NO: 26) 3'. In embodiments, provided herein is a composition linking CpG-ODN to an anti-miR155 having the sequence: 5' G*G*T GCA TCG ATG CAGG*G*G* G*G (SEQ ID NO: 1) xxxxx ACCCCTATCACAATTAGCATTAA (SEQ ID NO: 27) 3', where nucleotide T in SEQ ID NO: 27 can be substituted with nucleotide U. In embodiments, a compound described herein includes a composition linking CpG-ODN to an anti-miR155 having the sequence: 5' G*G*T GCA TCG ATG CAGG*G*G* G*G (SEQ ID NO: 1) xxxxx mA*mC*mC*mC*mC*mU*mA*mU*mC*mA*mC* mA*mA*mU*mU*mA*mG*mC*mA*m U*mU*mA*mA (SEQ ID NO: 28) 3'. In embodiments, provided herein is a composition linking CpG-ODN to an anti-miR155 having the sequence: 5' T*G*C*T*G*C*T*T*T*T*G*T*G*C*T*T*T*T*G* T*G*C*T*T (SEQ ID NO: 11) xxxxx ACCCCTATCACAATTAGCATTAA (SEQ ID NO: 27) 3'. In embodiments, provided herein is a composition linking CpG-ODN to an anti-miR155 having the sequence: 5' T*G*C*T*G*C*T*T*T*T*G*T*G*C*T*T*T*T*G* T*G*C*T*T (SEQ ID NO: 11) xxxxx mA*mC*mC*mC*mC*mU*mA*mU*mC*mA*mC* mA*mA*mU*mU*mA*mG*mC*mA*m U*mU*mA*mA (SEQ ID NO: 28) 3'. Sequences of the miR155 mimics are listed in Table 4:

TABLE 4

Compound and component sequences.

| NAME | SEQUENCE (* = phosphorothioate linkage), xxxxx may be -(CH$_2$)$_n$-PO$_4$-[(CH$_2$)$_n$-PO$_4$]$_z$-(CH$_2$)$_n$) bonded to phosphate groups at both ends except at the termini where terminal phosphates are optionally added and 5'x has an OH terminus and 3' x has a -C$^6$-NH$_2$ bonded to the final phosphate group, other linkages are phosphodiester. | SEQ ID NOS: |
|---|---|---|
| CpG D19-Sense miR155 unmodified | 5'-G*G*TGCATCGATGCAGG*G*G*G*G xxxxx rCrUrC rCrUrA rCrArU rArUrU rArGrC rArUrU rArArC rArUrU-3' | 1, 29 |
| CpG D12-Sense miR155 fluoro modified 2U at 3' end | 5'-G*G*TGCATCGATGCAGG*G*G*G*G xxxxx rCrUrC rCrUrA rCrArU rArUrU rArGrC rArUrU rArArC rAfUfU-3' | 1, 30 |
| Complementary mir | 5'-rUrGrU rUrArA rUrGrC rUrArA rUrArU rGrUrA rGrGrA rG-3' | 31 |

In embodiments, a CpG(D19)-scrambled RNA of sequence 5' G*G*T GCA TCG ATG CAGG*G*G* G*G (SEQ ID NO: 1) xxxxx mGmUmAmGmAmAmCmCmG-mUmAmCmUmCmGmUmCmAmCmUmUmA (SEQ ID NO: 32) 3' is used as a control ODN (included in FIG. 1).

In embodiments, provided herein is a composition linking CpG-ODN to an anti-miR125b having the sequence: 5' G*G*T GCA TCG ATG CAGG*G*G* G*G (SEQ ID NO: 1) xxxxx TCACAAGTTAGGGTCTCAGGGA (SEQ ID NO: 33) 3', where nucleotide T can be substituted with nucleotide U in SEQ ID NO: 33. In embodiments, provided herein is a composition linking CpG-ODN to an anti-miR125b having the sequence: 5' G*G*T GCA TCG ATG CAGG*G*G* G*G (SEQ ID NO: 1) xxxxx mU*mC*mA*mC*mA*mA*mG*mU*mU*mA*mG* mG*mG*mU*mC*mU*mC*mA*mG*m G*mG*mA (SEQ ID NO: 34) 3'.

In embodiments, provided herein is a composition linking CpG-ODN to an anti-miR146a having the sequence: 5' G*G*T GCA TCG ATG CAGG*G*G* G*G (SEQ ID NO: 1) xxxxx CCCATGGAATTCAGTTCTCA (SEQ ID NO: 35) 3', where nucleotide T can be substituted with nucleotide U in SEQ ID NO: 35. In embodiments, provided herein is a composition linking CpG-ODN to an anti-miR125b having the sequence: 5' G*G*T GCA TCG ATG CAGG*G*G* G*G (SEQ ID NO: 1) xxxxx mC*mC*mC*mA*mT*mG*mG*mA*mA*mT*mT* mC*mA*mG*mT*mT*mC*mT*mC*mA (SEQ ID NO: 36) 3'. In embodiments, provided herein is a composition linking CpG-ODN to an anti-miR146a having the sequence: 5' G*G*T GCA TGC ATG CAGG*G*G* G*G (SEQ ID NO: 2) xxxxx CCCATGGAATTCAGTTCTCA (SEQ ID NO: 35) 3'. In embodiments, provided herein is a composition linking CpG-ODN to an anti-miR146a having the sequence: G*G*T GCA TGC ATG CAGG*G*G* G*G (SEQ ID NO: 2) xxxxx mC*mC*mC*mA*mT*mG*mG*mA*mA*mT*mT* mC*mA*mG*mT*mT*mC*mT*mC*mA (SEQ ID NO: 36) 3'.

In embodiments, the compound including a nucleic acid sequence (CpG-ODN) is conjugated to an anti-miR or miRNA-mimic sequence, with one or more linkers described herein.

In embodiments, the compound including a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID NOs: 1-14, is conjugated to an anti-miR or miRNA-mimic sequence, with one or more linkers described herein.

In embodiments, the compound including a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID NOs: 1-14, is conjugated to a nucleic acid sequence having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID Nos 16-31, 33-36 and 48, with one or more linkers described herein.

In embodiments, the compound including a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID NOs: 1-14, is conjugated to a second nucleic acid sequence having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID Nos 16-31, 33-36 and 48, with one or more linkers described herein, where the second nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) phosphorothioate linkages.

In embodiments, the compound including a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID NOs: 1-14, is conjugated to a second nucleic acid sequence having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID Nos 16-31, 33-36 and 48, with one or more linkers described herein, where the second nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) chemically modified nucleotides. In embodiments, a chemical modification is selected from the group consisting of a 2' 0-Methyl, 2'-deoxy-2'fluoro, 2'-deoxy, a universal base, 5-C-methyl, an inverted deoxy abasic residue incorporation, and a locked nucleic acid.

In embodiments, the compound including a nucleic acid sequence (CpG-ODN) having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID NOs: 1-14, is conjugated to a second nucleic acid sequence having about 80%-100% (e.g., 80%, 85%, 90%, 91%, 92%, 93%, 94%, 95%, 96%, 97%, 98%, 99% or 100%) sequence identity with at least a 15 nucleobase sequence of one of SEQ ID Nos 16-31, 33-36 and 48, with one or more linkers described herein, where the second nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) phosphorothioate linkages and one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) chemically modified nucleotides. In embodiments, a chemical modification is selected from the group consisting of a 2' 0-Methyl, 2'-deoxy-2'fluoro, 2'-deoxy, a universal base, 5-C-methyl, an inverted deoxy abasic residue incorporation, and a locked nucleic acid.

In embodiments, the compound including a nucleic acid sequence (CpG-ODN) selected from SEQ ID NOs: 1-14, is conjugated to an anti-miR or miRNA-mimic sequence, with one or more linkers described herein.

In embodiments, the compound including a nucleic acid sequence (CpG-ODN) selected from one of SEQ ID NOs: 1-14, is conjugated to a nucleic acid sequence selected from SEQ ID Nos 16-31, 33-36 and 48, with one or more linkers described herein.

In embodiments, the compound including a nucleic acid sequence (CpG-ODN) selected from one of SEQ ID NOs: 1-14, is conjugated to a second nucleic acid sequence selected from SEQ ID Nos 16-31, 33-36 and 48, with one or more linkers described herein, where the second nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) phosphorothioate linkages.

In embodiments, the compound including a nucleic acid sequence (CpG-ODN) selected from one of SEQ ID NOs: 1-14, is conjugated to a second nucleic acid sequence selected from SEQ ID Nos 16-31, 33-36 and 48, with one or more linkers described herein, where the second nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) chemically modified nucleotides. In embodiments, a chemical modification is selected from the group consisting of a 2' 0-Methyl, 2'-deoxy-2'fluoro, 2'-deoxy, a universal base, 5-C-methyl, an inverted deoxy abasic residue incorporation, and a locked nucleic acid.

In embodiments, the compound including a nucleic acid sequence (CpG-ODN) selected from one of SEQ ID NOs: 1-14, is conjugated to a second nucleic acid sequence selected from SEQ ID Nos 16-31, 33-36 and 48, with one or more linkers described herein, where the second nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) phosphorothioate linkages and one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) chemically modified nucleotides. In embodiments, a chemical modification is selected from the group consisting of a 2' 0-Methyl, 2'-deoxy-2'fluoro, 2'-deoxy, a universal base, 5-C-methyl, an inverted deoxy abasic residue incorporation, and a locked nucleic acid.

In embodiments, the compound including a nucleic acid sequence (CpG-ODN) selected from one of SEQ ID NOs: 1-14, is conjugated to a second nucleic acid sequence selected from SEQ ID Nos 16-31, 33-36 and 48, with one or more linkers described herein, where the second nucleic acid sequence contains phosphorothioate linkages for all the internucleotide linkages.

In embodiments, the compound including a nucleic acid sequence (CpG-ODN) selected from one of SEQ ID NOs: 1-14, is conjugated to a second nucleic acid sequence selected from SEQ ID Nos 16-31, 33-36 and 48, with one or more linkers described herein, where the second nucleic acid sequence contains nucleotides that are all chemically modified (e.g., 2' 0-Methyl).

In embodiments, the compound including a nucleic acid sequence (CpG-ODN) selected from one of SEQ ID NOs: 1-14, is conjugated to a second nucleic acid sequence selected from SEQ ID Nos 16-31, 33-36 and 48, with one or more linkers described herein, where the second nucleic acid sequence contains phosphorothioate linkages for all the internucleotide linkages and contains nucleotides that are all chemically modified (e.g., 2' 0-Methyl).

In embodiments, the compound including a nucleic acid sequence of an anti-miR or miRNA-mimic sequence, where the nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) phosphorothioate linkages and/or one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) chemically modified nucleotides. In embodiments, a chemical modification is selected from the group consisting of a 2' 0-Methyl, 2'-deoxy-2'fluoro, 2'-deoxy, a universal base, 5-C-methyl, an inverted deoxy abasic residue incorporation, and a locked nucleic acid.

In embodiments, the compound including a nucleic acid sequence of an anti-miR or miRNA-mimic sequence selected from SEQ ID Nos 16-31, 33-36 and 48, where the nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) phosphorothioate linkages and/or one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) chemically modified nucleotides. In embodiments, a chemical modification is selected from the group consisting of a 2' 0-Methyl, 2'-deoxy-2'fluoro, 2'-deoxy, a universal base, 5-C-methyl, an inverted deoxy abasic residue incorporation, and a locked nucleic acid.

In embodiments, the linker is a covalent linker (i.e. a linker that covalently attaches at least two (e.g. 2) portions of a compound). In embodiments, the linker is or includes a substituted (e.g. substituted with a substituent group, size-limited substituent group or lower substituent group) or unsubstituted alkylene or heteroalkylene linker. In embodiments, the nucleic acid conjugated to anti-miRs and miRNA mimics includes more than one substituted (e.g. substituted with a substituent group, size-limited substituent group or lower substituent group) or unsubstituted heteroalkylene linkers. Linkers may be added during the synthesis in sequence. In embodiments, heteroalkylene linkers are connected to each other with an intervening phosphate bond. In embodiments, the covalent linker is a substituted (e.g. substituted with a substituent group, size-limited substituent group or lower substituent group) or unsubstituted heteroalkylene linker.

In embodiments, the linker is a substituted (e.g. substituted with a substituent group, size-limited substituent group or lower substituent group) or unsubstituted heteroalkylene or substituted (e.g. substituted with a substituent group, size-limited substituent group or lower substituent group) or unsubstituted cyclo-heteroalkylene. A "cyclo-heteroalkylene," as used herein is a heteroalkylene having a one or more divalent cyclic moieties within the heteroalkylene chain. The cyclic moiety may be a substituted (e.g. substituted with a substituent group, size-limited substituent group or lower substituent group) or unsubstituted cycloalklylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene or substituted (e.g. substituted with a substituent group, size-limited substituent group or lower substituent group) or unsubstituted heteroarylene. In embodiments, the cyclic moiety is a substituted (e.g. substituted with a substituent group, size-limited substituent group or lower substituent group) or unsubstituted ribose (e.g., a nucleoside). In embodiments, the cyclic moiety serves as a branch point of the linker thereby forming a branched linker. The cyclic moiety branch point may be used to attach additional functional moieties to the conjugates provided herein, such as detectable moieties, drug moieties or biomolecule. As explained in more detail below, the additional functional moieties may be connected using click chemistry techniques as known in the art.

In embodiments, the linker is or contains a moiety having the formula:

In the formula above, the symbol n is an integer from 1 to 5 (e.g., 3) and the symbol z is an integer from 0 to 50 (e.g. from 0 to 25, 0 to 10, or 0 to 5). In embodiments, n is 3 and z is 0 to 5 or 1 to 5. In embodiments, n is 3 and z is 0 to 4 or 1 to 4. In embodiments, n is 3 and z is 0 to 3 or 1 to 3. In embodiments, n is 3 and z is 3.

For example, the linker may have the structure below, where the linker connects with the 3' phosphate of the guanine on one end and the 5' phosphate of the thymidine on the other end:

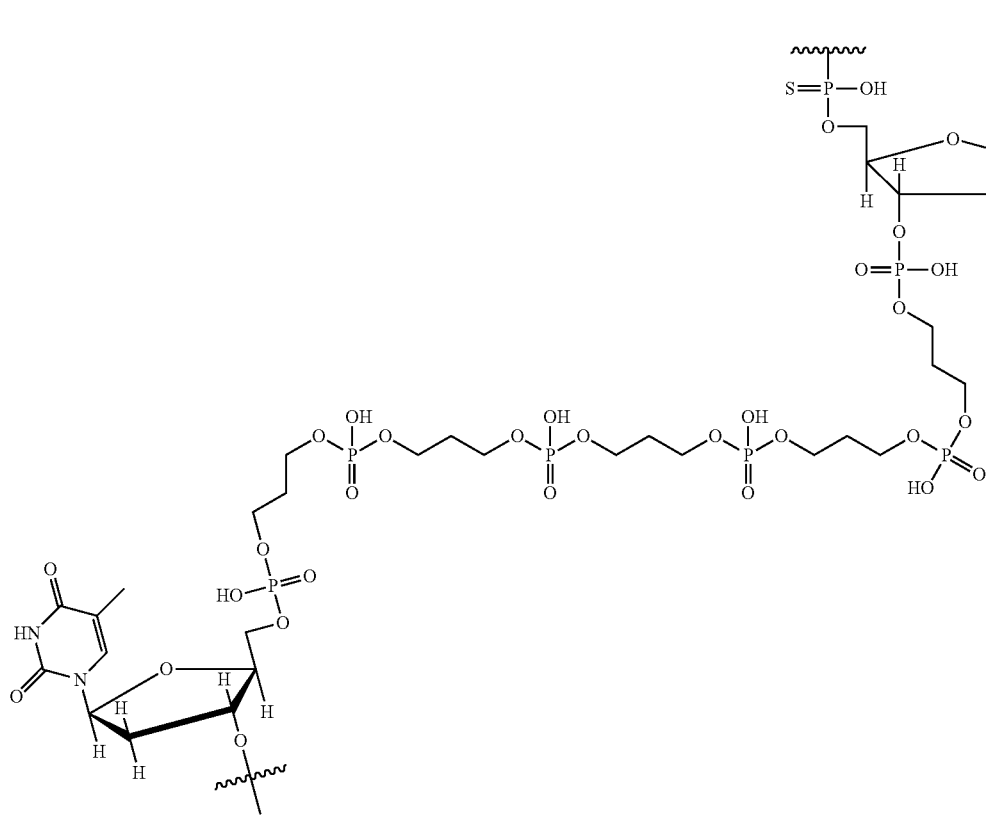

In embodiments, the guanidine above is connected to the nucleic acid sequence (CpG-ODN), and the thymidine is connected to an anti-miR or miRNA-mimic sequence.

In embodiments, the linker may include a moiety selected from an azide group, a protected amino group, N-hydroxysuccinimide (NHS) group, and a protected sulfhydryl group.

In embodiments, the linker may include a protected sulfhydryl group that is conjugated to a moiety selected from the group consisting of divinyl sulfone derivative, acryloyl derivative, and/or maleimido derivative. In embodiments, the acryloyl derivative is acryloyl chloride.

In embodiments, linker may be conjugated to polyethylene glycol (PEG) or bisphosphonate moiety.

In embodiments, linker may include an unsubstituted $C_3$ heteroalkylene.

In embodiments, linker may include an unsubstituted $C_6$ to $C_{12}$ heteroalkylene.

In embodiments, the linker may be substituted with a reactive group (e.g. a click chemistry reactive group) or a protected reactive group. The reactive group may be used to conjugate the CpG-ODN to an anti-miR or miRNA-mimic and/or to an additional functional moiety as described herein, such as a detectable moiety or biomolecule (e.g. a targeting moiety).

Thus, the linker may include further modification, conjugation, or attachment of additional moieties.

The reactive group used to conjugate the CpG-ODN to an anti-miR or miRNA-mimic compound to an additional functional moiety may be any applicable reactive group useful in bioconjugate chemistry. See Hermanson, *Bioconjugate Techniques* 1996, Academic Press, Inc., San Diego.

In embodiments, the reactive group is a click chemistry reactive groups. Click chemistry refers to a group of reactions that are fast, simple to use, easy to purify, versatile, regiospecific, and give high product yields. Four different click reactions are possible: (1) Cycloadditions—these primarily refer to 1,3-dipolar cycloadditions, but also include hetero-Diels-Alder cycloadditions; (2) Nucleophilic ring-openings—these refer to the opening of strained heterocyclic electrophiles, such as aziridines, epoxides, cyclic sulfates, aziridinium ions, episulfonium ions; (3) carbonyl chemistry of the non-aldol type—examples include the formations of ureas, thioureas, hydrazones, oxime ethers, amides, aromatic heterocycles; (4) additions of carbon-carbon multiple bonds—examples include epoxidations, aziridinations, dihydrooxylations, sulfenyl halide additions, nitrosyl halide additions, and certain Michael additions. In embodiments, the click reaction used may be $Cu^I$-catalyzed Huisgen 1,3-dipolar cycloaddition (HDC) of azides or terminal alkynes to form 1,2,3-triazoles. In embodiments, the click reaction may be a copper-free reaction.

In embodiments, the click chemistry reactive group is or includes an azide groups, an alkene group, an amino groups, an N-hydroxysuccinimide group, a sulfhydryl group, a divinyl sulfone derivative, or a maleimido derivative. Thus, in embodiments, the linker is substituted with a reactive group (e.g. a click chemistry reactive group) or a protected reactive group, including, for example, a protected amino group or a N-hydroxysuccinimide group, suitable for conjugation by N-hydroxysuccinimide (NHS) chemistry; a sulfhydryl group that may be conjugated with divinyl sulfone; a protected sulfhydryl group, which may be conjugated with 1-alkyl-3-methylacryloyl (acryloyl) chloride or acryloyl derivatives; a protected sulfhydryl group, which may be conjugated with maleimido derivatives.

Provided below is a structural example of a cyclo-heteroalkylene branched linker:
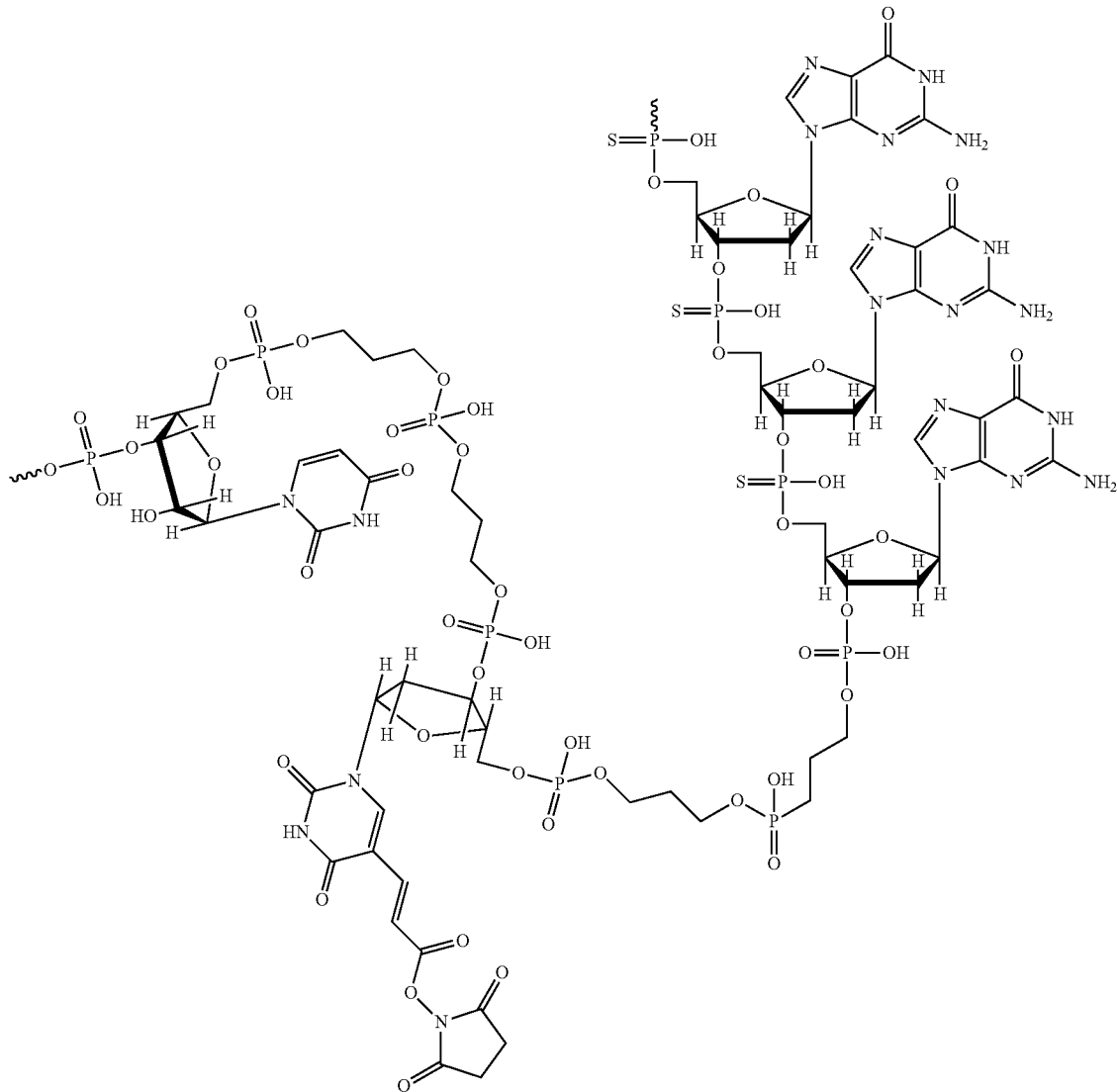
Substitution with NHS-Carboxy-dT
NHS esters react with nucleophiles, e.g., amines. NHS ester can be used for the introduction of the substituent, e.g., PEG (reaction with PEG-amine).
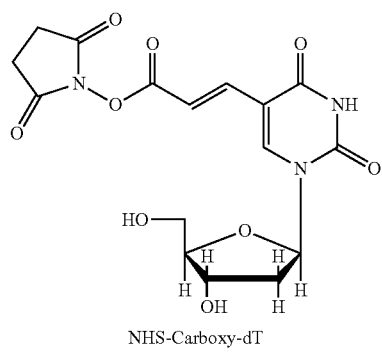
NHS-Carboxy-dT As shown above, a cyclo-heteroalkylene branched linker connects with the 3' phosphate of the guanine on one end and the 5' phosphate of the thymidine on the other end. The moiety of the cyclo-heteroalkylene branched linker is a branch point and is a 5-substituted thymidine. The thymidine is substituted in position 5 with a reactive group containing an NHS moiety, which can serve as a reactive group to connect to an additional functional moiety Additional examples of compounds that can be used to serve as moiety branch points containing reactive functional groups and protected reactive functional groups are provided below.

Fmoc amino-modifier C6 dT

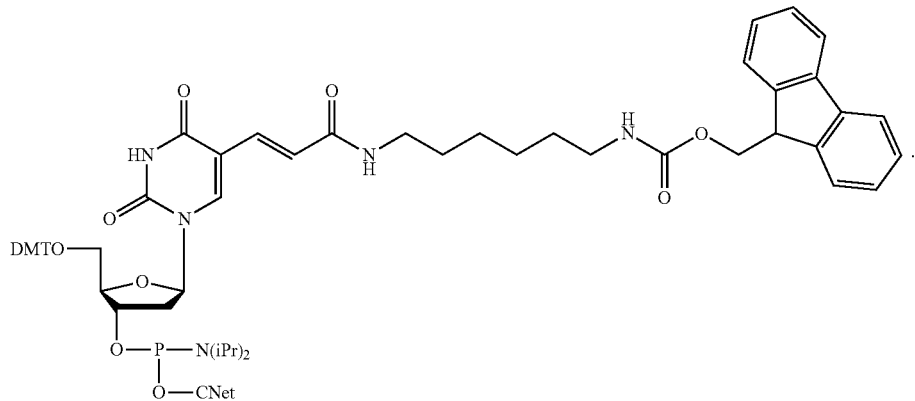

S-Bz-thiol-modifier C6 dT

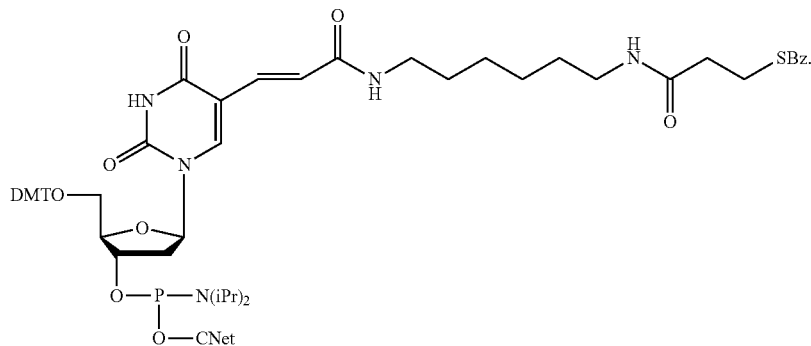

DBCO-dT

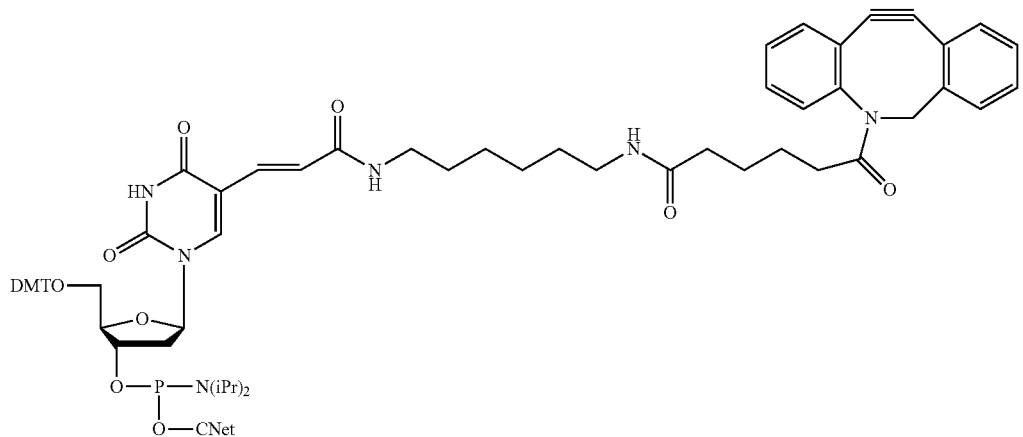

DBCO-sulfo-NHS Ester

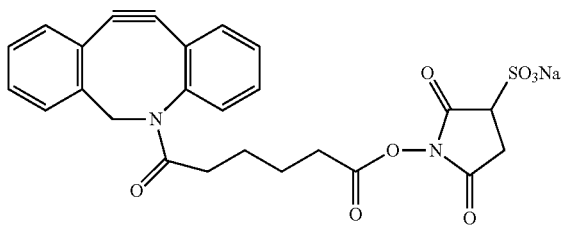

In embodiments, the linker branch point may be non-cyclic. An example of a compound that can be used to serve as non-cyclic moiety branch point within the linker that contains a reactive functional group and protected reactive functional groups is provided below.

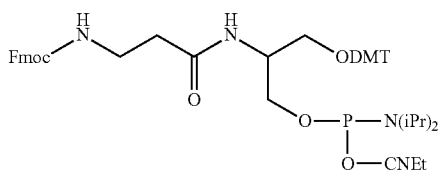

As set forth above, the reactive group may be used to conjugate the CpG-ODN to an anti-miR or miRNA mimic nucleic acid sequence and/or to an additional functional moiety such as a detectable moiety, therapeutic moiety (e.g., drug moiety), targeting moiety or biomolecule. Additional functional moieties include a fluorescent label, a targeting compound (bone targeting bisphosphonates), a drug, or an antibody. In embodiments, additional moiety is a chemically reactive moiety, detectable moiety, therapeutic moiety (e.g. anti-cancer agent or anti-viral agent), nucleic acid sequence, DNA sequence, or nucleic acid analogs. In embodiments, the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, an additional moiety is a therapeutic moiety (e.g. anti-cancer agent or anti-viral agent).

In embodiments, the additional functional moiety is a substituted (e.g. substituted with a substituent group, size-limited substituent group or lower substituent group) or unsubstituted alkyl, substituted (e.g. substituted with a substituent group, size-limited substituent group or lower substituent group) or unsubstituted heteroalkyl, substituted (e.g. substituted with a substituent group, size-limited substituent group or lower substituent group) or unsubstituted cycloalkyl, substituted (e.g. substituted with a substituent group, size-limited substituent group or lower substituent group) or unsubstituted heterocycloalkyl, substituted (e.g. substituted with a substituent group, size-limited substituent group or lower substituent group) or unsubstituted aryl, or substituted (e.g. substituted with a substituent group, size-limited substituent group or lower substituent group) or unsubstituted heteroaryl. In embodiments, the additional moiety is a substituted (e.g. substituted with a substituent group, size-limited substituent group or lower substituent group) or unsubstituted $C_1$-$C_{40}$ alkyl, substituted (e.g. substituted with a substituent group, size-limited substituent group or lower substituent group) or unsubstituted 2 to 40 membered heteroalkyl, substituted (e.g. substituted with a substituent group, size-limited substituent group or lower substituent group) or unsubstituted $C_3$-$C_8$ cycloalkyl, substituted or unsubstituted 3 to 8 membered heterocycloalkyl, substituted or unsubstituted $C_6$-$C_{10}$ aryl, or substituted (e.g. substituted with a substituent group, size-limited substituent group or lower substituent group) or unsubstituted 5 to 10 membered heteroaryl. In embodiments, the additional moiety is a substituted (e.g. substituted with a substituent group, size-limited substituent group or lower substituent group) $C_1$-$C_{40}$ alkyl, substituted 2 to 40 membered heteroalkyl, substituted (e.g. substituted with a substituent group, size-limited substituent group or lower substituent group) $C_3$-$C_8$ cycloalkyl, substituted (e.g. substituted with a substituent group, size-limited substituent group or lower substituent group) 3 to 8 membered heterocycloalkyl, substituted (e.g. substituted with a substituent group, size-limited substituent group or lower substituent group) $C_6$-$C_{10}$ aryl, or substituted (e.g. substituted with a substituent group, size-limited substituent group or lower substituent group) 5 to 10 membered heteroaryl. In embodiments, the additional functional moiety is an $R^1$-substituted $C_1$-$C_{40}$ alkyl, $R^1$-substituted 2 to 40 membered heteroalkyl, $R^1$-substituted $C_3$-$C_8$ cycloalkyl, $R^1$-substituted 3 to 8 membered heterocycloalkyl, $R^1$-substituted $C_6$-$C_{10}$ aryl, or $R^1$-substituted 5 to 10 membered heteroaryl. In embodiments, the additional functional moiety is an $R^1$-substituted $C_1$-$C_{40}$ alkyl. In embodiments, the additional functional moiety is an -(unsubstituted $C_1$-$C_{40}$ alkylene)-$R^1$. In embodiments, the additional functional moiety is an -(unsubstituted linear $C_1$-$C_{40}$ alkylene)-$R^1$. In embodiments, the additional functional moiety is an -(unsubstituted $C_3$-$C_{21}$ alkylene)-$R^1$. In embodiments, the additional functional moiety is an -(unsubstituted $C_3$-$C_{18}$ alkylene)-$R^1$. In embodiments, the additional functional moiety is an -(unsubstituted linear $C_3$-$C_{15}$ alkylene)-$R^1$. In embodiments, the additional functional moiety is an -(unsubstituted linear $C_6$-$C_{21}$ alkylene)-$R^1$. In embodiments, the additional functional moiety is an -(unsubstituted linear $C_9$-$C_{21}$ alkylene)-$R^1$. In embodiments, the additional functional moiety is an -(unsubstituted linear $C_9$-$C_{18}$ alkylene)-$R^1$. In embodiments, the additional functional moiety is an -(unsubstituted linear $C_9$-$C_{15}$ alkylene)-$R^1$. In embodiments, the additional functional moiety is an -(unsubstituted linear $C_{12}$-$C_{15}$ alkylene)-$R^1$. In embodiments, the additional functional moiety is an -(unsubstituted linear $C_{12}$ alkylene)-$R^1$. In embodiments, the additional functional moiety is an -(unsubstituted linear $C_{13}$ alkylene)-$R^1$. In embodiments, the additional functional moiety is an -(unsubstituted linear $C_{14}$ alkylene)-

R¹. In embodiments, the additional functional moiety is an -(unsubstituted linear C₁₅ alkylene)-R¹. In embodiments, the additional functional moiety is an R¹-substituted 2 to 40 membered heteroalkyl. In embodiments, the additional functional moiety is an -(unsubstituted 2 to 40 membered heteroalkylene)-R¹. In embodiments, the additional functional moiety is a -(substituted linear 2 to 40 membered heteroalkylene)-R¹. In embodiments, the additional functional moiety is a -(substituted 5 to 40 membered heteroalkylene)-R¹. In embodiments, the additional functional moiety is a -(substituted 10 to 40 membered heteroalkylene)-R¹. In embodiments, the additional functional moiety is a -(substituted 15 to 40 membered heteroalkylene)-R¹. In embodiments, the additional functional moiety is a -(substituted 20 to 40 membered heteroalkylene)-R¹. In embodiments, the additional functional moiety is a -(substituted 30 to 40 membered heteroalkylene)-R¹. In embodiments, the additional functional moiety is a -(substituted 2 to 35 membered heteroalkylene)-R¹. In embodiments, the additional functional moiety is a -(substituted 2 to 30 membered heteroalkylene)-R¹. In embodiments, the additional functional moiety is a -(substituted 2 to 25 membered heteroalkylene)-R¹. In embodiments, the additional functional moiety is a -(substituted 2 to 20 membered heteroalkylene)-R¹. In embodiments, the additional functional moiety is a -(substituted 2 to 10 membered heteroalkylene)-R¹. In embodiments, the additional functional moiety is a -(substituted 2 to 50 membered heteroalkylene)-R¹. In embodiments, the additional functional moiety is a -(substituted 2 to 60 membered heteroalkylene)-R¹. In embodiments, the additional functional moiety is a substituted 2 to 40 membered heteroalkyl. In embodiments, the additional functional moiety is a substituted 10 to 50 membered heteroalkyl. In embodiments, the additional functional moiety is a substituted 20 to 40 membered heteroalkyl. In embodiments, the additional functional moiety is a substituted 25 to 40 membered heteroalkyl. In embodiments, the additional functional moiety is a substituted 30 to 40 membered heteroalkyl.

R¹ is a oxo, halogen, —CN, —CF₃, —NH₂, —OH, —SH, —N₃, substituted (e.g. substituted with a substituent group, size-limited substituent group or lower substituent group) or unsubstituted alkyl, substituted (e.g. substituted with a substituent group, size-limited substituent group or lower substituent group) or unsubstituted hetoeroalkyl, substituted (e.g. substituted with a substituent group, size-limited substituent group or lower substituent group) or unsubstituted substituted (e.g. substituted with a substituent group, size-limited substituent group or lower substituent group) or unsubstituted cycloalkyl, substituted (e.g. substituted with a substituent group, size-limited substituent group or lower substituent group) or unsubstituted heterocycloalkyl, substituted (e.g. substituted with a substituent group, size-limited substituent group or lower substituent group) or unsubstituted aryl or substituted or unsubstituted heteroaryl. In embodiments, R¹ in an additional functional moiety is a detectable moiety or a therapeutic moiety. In embodiments, R¹ in an additional functional moiety is a detectable moiety. In embodiments, the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety.

In embodiments, R¹ in an additional functional moiety is a therapeutic moiety (e.g. anti-cancer agent or anti-viral agent). In embodiments, R¹ in an additional functional moiety is H. In embodiments, an additional functional moiety is oxo. In embodiments, an additional functional moiety is oxygen. In embodiments, an additional functional moiety is sulfur. In embodiments, an additional functional moiety is =S.

In embodiments, the further linking substituent includes a substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene or substituted (e.g. substituted with a substituent group, size-limited substituent group or lower substituent group) or unsubstituted heteroarylene. The further linking substituent may include a PEG moiety attached to the reactive group or additional moiety.

In embodiments, the linker includes an unsubstituted C₃ alkylene (e.g. as described above). In embodiments, the linker may be unsubstituted C₁₅ alkylene. In embodiments, the linker includes an unsubstituted C₆ to C₁₆ alkylene. In embodiments, the linker may be a substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted (e.g. substituted with a substituent group, size-limited substituent group or lower substituent group) or unsubstituted heteroarylene. In embodiments, the linker may be a substituted (e.g. substituted with a substituent group, size-limited substituent group or lower substituent group) or unsubstituted C₁-C₄₀ alkylene, substituted (e.g. substituted with a substituent group, size-limited substituent group or lower substituent group) or unsubstituted 2 to 40 membered heteroalkylene, substituted (e.g. substituted with a substituent group, size-limited substituent group or lower substituent group) or unsubstituted C₃-C₈ cycloalkylene, substituted (e.g. substituted with a substituent group, size-limited substituent group or lower substituent group) or unsubstituted 3 to 8 membered heterocycloalkylene, substituted (e.g. substituted with a substituent group, size-limited substituent group or lower substituent group) or unsubstituted C₆-C₁₀ arylene, or substituted (e.g. substituted with a substituent group, size-limited substituent group or lower substituent group) or unsubstituted 5 to 10 membered heteroarylene. In embodiments, the linker may be an unsubstituted C₁-C₄₀ alkylene, unsubstituted 2 to 40 membered heteroalkylene, unsubstituted C₃-C₈ cycloalkylene, unsubstituted 3 to 8 membered heterocycloalkylene, unsubstituted C₆-C₁₀ arylene, or unsubstituted 5 to 10 membered heteroarylene. In embodiments, the linker may be a substituted (e.g. substituted with a substituent group, size-limited substituent group or lower substituent group) 2 to 40 membered heteroalkylene.

A linker may be a bond, nucleic acid sequence, two nucleic acid sequences, DNA sequence, two DNA sequences, nucleic acid analog sequence, substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted (e.g. substituted with a substituent group, size-limited substituent group or lower substituent group) or unsubstituted heteroarylene.

In embodiments, the linker is or contains a substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted (e.g. substituted with a substituent group, size-limited substituent group or lower substituent group) or unsubstituted heteroarylene. In embodiments, the linker is a substituted (e.g. substituted with a substituent group, size-limited substituent group or lower substituent group) or unsubstituted $C_1$-$C_{20}$ alkylene, substituted (e.g. substituted with a substituent group, size-limited substituent group or lower substituent group) or unsubstituted 2 to 20 membered heteroalkylene, substituted (e.g. substituted with a substituent group, size-limited substituent group or lower substituent group) or unsubstituted $C_3$-$C_8$ cycloalkylene, substituted (e.g. substituted with a substituent group, size-limited substituent group or lower substituent group) or unsubstituted 3 to 8 membered heterocycloalkylene, substituted (e.g. substituted with a substituent group, size-limited substituent group or lower substituent group) or unsubstituted $C_6$-$C_{10}$ arylene, or substituted (e.g. substituted with a substituent group, size-limited substituent group or lower substituent group) or unsubstituted 5 to 10 membered heteroarylene. In embodiments, the linker is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the linker is an unsubstituted $C_1$-$C_{20}$ alkylene. In embodiments, the linker is a substituted (e.g. substituted with a substituent group, size-limited substituent group or lower substituent group) or unsubstituted $C_1$-$C_{40}$ alkylene, substituted (e.g. substituted with a substituent group, size-limited substituent group or lower substituent group) or unsubstituted 2 to 40 membered heteroalkylene, substituted (e.g. substituted with a substituent group, size-limited substituent group or lower substituent group) or unsubstituted $C_3$-$C_8$ cycloalkylene, substituted (e.g. substituted with a substituent group, size-limited substituent group or lower substituent group) or unsubstituted 3 to 8 membered heterocycloalkylene, substituted (e.g. substituted with a substituent group, size-limited substituent group or lower substituent group) or unsubstituted $C_6$-$C_{10}$ arylene, or substituted (e.g. substituted with a substituent group, size-limited substituent group or lower substituent group) or unsubstituted 5 to 10 membered heteroarylene. In embodiments, the linker is a substituted (e.g. substituted with a substituent group, size-limited substituent group or lower substituent group) or unsubstituted $C_1$-$C_{40}$ alkylene. In embodiments, the linker is a substituted (e.g. substituted with a substituent group, size-limited substituent group or lower substituent group) or unsubstituted 2 to 40 membered heteroalkylene. In embodiments, the linker is a substituted (e.g. substituted with a substituent group, size-limited substituent group or lower substituent group) 2 to 40 membered heteroalkylene. In embodiments, the linker includes alkyl phosphates (e.g., propyl phosphates). In embodiments, the linker has alkyl phosphates (e.g., propyl phosphates) bonded to the reminder of the compound by phosphates at both ends. In embodiments, the linker has 1-5 alkyl phosphates (e.g., propyl phosphates) bonded to the reminder of the compound by phosphates at both ends. In embodiments, the linker has 1-4 alkyl phosphates (e.g., propyl phosphates) bonded to the reminder of the compound by phosphates at both ends. In embodiments, the linker has 4 alkyl phosphates (e.g., propyl phosphates) bonded to the reminder of the compound by phosphates at both ends. A person having ordinary skill in the art will recognize that a linker having alkyl phosphates that is bonded to the remainder of the compound by phosphates on both ends will have one more phosphate than alkylene groups (e.g., a linker having 4 alkyl phosphates that is bonded to the reminder of the compound by phosphates at both ends will have five phosphates and four alkyl groups with alternating phosphate groups and alkyl groups).

In embodiments, anti-miR and miRNA mimics may include modifications such as 2' 0-Methyl, 2'-deoxy-2'fluoro, 2'-deoxy, a universal base, 5-C-methyl, an inverted deoxy abasic residue incorporation, or a locked nucleic acid, or any combination(s) thereof. In embodiments, the anti-miR and miRNA mimics may have a modification positioned at the terminal nucleobase of the anti-miR and miRNA mimics. In embodiments, the anti-miR and miRNA mimics may not have a modification positioned at the terminal nucleobase of the anti-miR and miRNA mimics. In embodiments, the modification of the anti-miR and miRNA mimics protects the compound against serum-derived nucleases (e.g. is nuclease resistant).

In embodiments, the (CpG-ODN) conjugated to an anti-miR or miRNA mimic has a terminal moiety. A terminal moiety is a chemically reactive moiety, detectable moiety, therapeutic moiety (e.g. anti-cancer agent or anti-viral agent), nucleic acid sequence, DNA sequence, substituted (e.g. substituted with a substituent group, size-limited substituent group or lower substituent group) or unsubstituted alkyl, substituted (e.g. substituted with a substituent group, size-limited substituent group or lower substituent group) or unsubstituted heteroalkyl, substituted (e.g. substituted with a substituent group, size-limited substituent group or lower substituent group) or unsubstituted cycloalkyl, substituted (e.g. substituted with a substituent group, size-limited substituent group or lower substituent group) or unsubstituted heterocycloalkyl, substituted (e.g. substituted with a substituent group, size-limited substituent group or lower substituent group) or unsubstituted aryl, or substituted (e.g. substituted with a substituent group, size-limited substituent group or lower substituent group) or unsubstituted heteroaryl.

In embodiments, a terminal moiety is a chemically reactive moiety, detectable moiety, therapeutic moiety (e.g. anti-cancer agent or anti-viral agent), nucleic acid sequence, DNA sequence, nucleic acid analogs, $R^1$-substituted or unsubstituted alkyl, $R^1$-substituted or unsubstituted heteroalkyl, $R^1$-substituted or unsubstituted cycloalkyl, $R^1$-substituted or unsubstituted heterocycloalkyl, $R^1$-substituted or unsubstituted aryl, or $R^1$-substituted or unsubstituted heteroaryl.

In embodiments, a CpG-ODN nucleic acid sequence conjugated to an anti-miR or miRNA-mimic conjugates includes a terminal moiety, wherein the terminal moiety is a detectable moiety. In embodiments, the CpG-ODN conjugated to an anti-miR or miRNA-mimic includes a terminal detectable moiety such as, a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, the CpG-ODN conjugated to an anti-miR or miRNA-mimic includes a terminal moiety, which is a therapeutic moiety (e.g., anti-cancer agent or anti-viral agent).

In embodiments, the CpG-ODN conjugated to an anti-miR or miRNA-mimic includes a terminal moiety, which is a hydrogen, oxo, halogen, —CN, —$CF_3$, —$NH_2$, —OH, —SH, —$N_3$, substituted (e.g. substituted with a substituent group, size-limited substituent group or lower substituent group) or unsubstituted alkyl, substituted (e.g. substituted with a substituent group, size-limited substituent group or lower substituent group) or unsubstituted heteroalkyl, substituted (e.g. substituted with a substituent group, size-limited substituent group or lower substituent group) or unsubstituted cycloalkyl, substituted (e.g. substituted with a substituent group, size-limited substituent group or lower substituent group) or unsubstituted heterocycloalkyl, substituted (e.g. substituted with a substituent group, size-limited substituent group or lower substituent group) or unsubstituted aryl, or substituted (e.g. substituted with a substituent group, size-limited substituent group or lower substituent group) or unsubstituted heteroaryl. In embodiments, the CpG-ODN conjugated to an anti-miR or miRNA-mimic includes a terminal moiety, which is a substituted (e.g. substituted with a substituent group, size-limited substituent group or lower substituent group) or unsubstituted $C_1$-$C_{40}$ alkyl, substituted (e.g. substituted with a substituent group, size-limited substituent group or lower substituent group) 2 to 40 membered heteroalkyl, substituted (e.g. substituted with a substituent group, size-limited substituent group or lower substituent group) $C_3$-$C_8$ cycloalkyl, substituted (e.g. substituted with a substituent group, size-limited substituent group or lower substituent group) 3 to 8 membered heterocycloalkyl, substituted (e.g. substituted with a substituent group, size-limited substituent group or lower substituent group) $C_6$-$C_{10}$ aryl, or substituted (e.g. substituted with a substituent group, size-limited substituent group or lower substituent group) 5 to 10 membered heteroaryl. In embodiments, the CpG-ODN conjugated to an anti-miR or miRNA-mimic includes a terminal moiety, which is a substituted (e.g. substituted with a substituent group, size-limited substituent group or lower substituent group) or unsubstituted $C_1$-$C_{40}$ alkyl, substituted (e.g. substituted with a substituent group, size-limited substituent group or lower substituent group) 2 to 40 membered heteroalkyl, substituted (e.g. substituted with a substituent group, size-limited substituent group or lower substituent group) $C_3$-$C_8$ cycloalkyl, substituted (e.g. substituted with a substituent group, size-limited substituent group or lower substituent group) 3 to 8 membered heterocycloalkyl, substituted (e.g. substituted with a substituent group, size-limited substituent group or lower substituent group) $C_6$-$C_{10}$ aryl, or substituted (e.g. substituted with a substituent group, size-limited substituent group or lower substituent group) 5 to 10 membered heteroaryl. In embodiments, the terminal moiety is an $R^1$-substituted $C_1$-$C_{40}$ alkyl, $R'$-substituted 2 to 40 membered heteroalkyl, $R^1$-substituted $C_3$-$C_8$ cycloalkyl, $R^1$-substituted 3 to 8 membered heterocycloalkyl, $R'$-substituted $C_6$-$C_{10}$ aryl, or $R'$-substituted 5 to 10 membered heteroaryl. In embodiments, the terminal moiety is an $R^1$-substituted $C_1$-$C_{40}$ alkyl. In embodiments, the terminal moiety is an -(unsubstituted $C_1$-$C_{40}$ alkylene)-$R^1$. In embodiments, the terminal moiety is an -(unsubstituted linear $C_1$-$C_{40}$ alkylene)-$R^1$. In embodiments, the terminal moiety is an -(unsubstituted $C_3$-$C_{21}$ alkylene)-$R^1$. In embodiments, the terminal moiety is an -(unsubstituted $C_3$-$C_{18}$ alkylene)-$R^1$. In embodiments, the terminal moiety is an -(unsubstituted linear $C_3$-$C_{15}$ alkylene)-$R^1$. In embodiments, the terminal moiety is an -(unsubstituted linear $C_6$-$C_{21}$ alkylene)-$R^1$. In embodiments, the terminal moiety is an -(unsubstituted linear $C_9$-$C_{21}$ alkylene)-$R^1$. In embodiments, the terminal moiety is an -(unsubstituted linear $C_9$-$C_{18}$ alkylene)-$R^1$. In embodiments, the terminal moiety is an -(unsubstituted linear $C_9$-$C_{15}$ alkylene)-$R^1$. In embodiments, the terminal moiety is an -(unsubstituted linear $C_{12}$-$C_{15}$ alkylene)-$R^1$. In embodiments, the terminal moiety is an -(unsubstituted linear $C_{12}$ alkylene)-$R^1$. In embodiments, the terminal moiety is an -(unsubstituted linear $C_{13}$ alkylene)-$R^1$. In embodiments, the terminal moiety is an -(unsubstituted linear $C_{14}$ alkylene)-$R^1$. In embodiments, the terminal moiety is an -(unsubstituted linear $C_{15}$ alkylene)-$R^1$. In embodiments, the terminal moiety is an $R^1$-substituted 2 to 40 membered heteroalkyl. In embodiments, the terminal moiety is an -(unsubstituted 2 to 40 membered heteroalkylene)-$R^1$. In embodiments, the terminal moiety is a -(substituted linear 2 to 40 membered heteroalkylene)-$R^1$. In embodiments, the terminal moiety is a -(substituted 5 to 40 membered heteroalkylene)-$R^1$. In embodiments, the terminal moiety is a -(substituted 10 to 40 membered heteroalkylene)-$R^1$. In embodiments, the terminal moiety is a -(substituted 15 to 40 membered heteroalkylene)-$R^1$. In embodiments, the terminal moiety is a -(substituted 20 to 40 membered heteroalkylene)-$R^1$. In embodiments, the terminal moiety is a -(substituted 30 to 40 membered heteroalkylene)-$R^1$. In embodiments, the terminal moiety is a -(substituted 2 to 35 membered heteroalkylene)-$R^1$. In embodiments, the terminal moiety is a -(substituted 2 to 30 membered heteroalkylene)-$R^1$. In embodiments, the terminal moiety is a -(substituted 2 to 25 membered heteroalkylene)-$R^1$. In embodiments, the terminal moiety is a -(substituted 2 to 20 membered heteroalkylene)-$R^1$. In embodiments, the terminal moiety is a -(substituted 2 to 10 membered heteroalkylene)-$R^1$. In embodiments, the terminal moiety is a -(substituted 2 to 50 membered heteroalkylene)-$R^1$. In embodiments, the terminal moiety is a -(substituted 2 to 60 membered heteroalkylene)-$R^1$.

In embodiments, the CpG-ODN conjugated to an anti-miR or miRNA-mimic includes a terminal moiety, which is a substituted (e.g. substituted with a substituent group, size-limited substituent group or lower substituent group) 2 to 40 membered heteroalkyl. In embodiments, the CpG-ODN conjugated to an anti-miR or miRNA-mimic includes a terminal moiety, which is a substituted (e.g. substituted with a substituent group, size-limited substituent group or lower substituent group) 10 to 50 membered heteroalkyl. In embodiments, the CpG-ODN conjugated to an anti-miR or miRNA-mimic includes a terminal moiety, which is a substituted (e.g. substituted with a substituent group, size-limited substituent group or lower substituent group) 20 to 40 membered heteroalkyl. In embodiments, the CpG-ODN conjugated to an anti-miR or miRNA-mimic includes a terminal moiety, which is a substituted (e.g. substituted with a substituent group, size-limited substituent group or lower substituent group) 25 to 40 membered heteroalkyl. In embodiments, the CpG-ODN conjugated to an anti-miR or miRNA-mimic includes a terminal moiety, which is a substituted (e.g. substituted with a substituent group, size-limited substituent group or lower substituent group) 30 to 40 membered heteroalkyl.

In embodiments, the CpG-ODN conjugated to an anti-miR or miRNA-mimic includes a terminal moiety with a $R^1$ group, in which $R^1$ is a detectable moiety or a therapeutic moiety. In embodiments, $R^1$ in the CpG-ODN conjugated to an anti-miR or miRNA-mimic includes a terminal moiety, which is a detectable moiety. In embodiments, $R^1$ in the CpG-ODN conjugated to an anti-miR or miRNA-mimic includes a detectable moiety, which is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, $R^1$ in the CpG-ODN conjugated to an anti-miR or miRNA-mimic includes a terminal moiety, which is a therapeutic moiety (e.g., anti-cancer agent or anti-viral agent). In embodiments, $R^1$ in the CpG-ODN conjugated to an anti-miR or miRNA-mimic includes a terminal moiety, which is H. In embodiments, $R^1$ in the CpG-ODN conjugated to an anti-miR or miRNA-mimic includes an oxo as a terminal moiety. In embodiments, $R^1$ in the CpG-ODN conjugated to an anti-miR or miRNA-mimic includes oxygen as a terminal moiety. In embodiments, $R^1$ in the CpG-ODN conjugated to an anti-miR or miRNA-mimic includes sulfur as a terminal moiety. In embodiments, $R^1$ in the CpG-ODN conjugated to an anti-miR or miRNA-mimic includes =S as a terminal moiety.

In embodiments, the CpG-ODN nucleic acid sequence of the compound includes unmethylated CpG motif (e.g., a CpG nucleic acid sequence or a GpC nucleic acid sequence). In embodiments, the CpG-ODN nucleic acid sequence includes a Class A CpG nucleic acid sequence, a Class B CpG nucleic acid sequence, or a Class C CpG nucleic acid sequence.

In embodiments, the compound includes CpG-ODN, in which C and G are nucleotides connected by a phosphodiester internucleotide linkage. In embodiments, the compound includes CpG, wherein C and G are nucleotides connected by a phosphodiester derivative internucleotide linkage. In embodiments, the CpG motif is unmethylated. In embodiments, C and G are connected as 5'C-G 3'. In embodiments, C and G are connected as 5'G-C 3'.

In embodiments, a Toll-like receptor (TLR)-binding DNA substituent is a Class A CpG oligodeoxynucleotide (ODN). In embodiments, a TLR-binding DNA substituent is a Class B CpG oligodeoxynucleotide (ODN). In embodiments, a TLR-binding DNA substituent is a Class C CpG oligodeoxynucleotide (ODN). In embodiments, a TLR-binding DNA substituent (e.g., TLR9-binding DNA substituent) consists of deoxyribonucleic acids with A, G, C, or T bases and phosphodiester linkages and/or phosphodiester derivative linkages (e.g., phosphorothioate linkage(s)).

In embodiments, the compound binds an endosomal TLR. In embodiments, the compound preferentially binds an endosomal TLR over other TLR. In embodiments, the compound specifically binds an endosomal TLR. In embodiments, the compound binds TLR3. In embodiments, the compound preferentially binds TLR3 over other TLR. In embodiments, the compound specifically binds TLR3. In embodiments, the compound binds TLR7. In embodiments, the compound preferentially binds TLR7 over other TLR. In embodiments, the compound specifically binds TLR7. In embodiments, the compound binds TLR8. In embodiments, the compound preferentially binds TLR8 over other TLR. In embodiments, the compound specifically binds TLR8. In embodiments, the compound binds TLR9. In embodiments, the compound preferentially binds TLR9 over other TLR. In embodiments, the compound specifically binds TLR9. In embodiments, the compound includes CpG, wherein C and G are nucleotides connected by a phosphodiester internucleotide linkage or phosphodiester derivative internucleotide linkage.

In embodiments, the TLR-binding DNA substituent is a Class A CpG oligodeoxynucleotide (ODN). In embodiments, the TLR-binding DNA substituent is a Class B CpG oligodeoxynucleotide (ODN). In embodiments, the TLR-binding DNA substituent is a Class C CpG oligodeoxynucleotide (ODN). In embodiments, the TLR-binding DNA substituent is ODN 1585, ODN 2216, ODN D19, or ODN 2336. In embodiments, the TLR-binding DNA substituent is ODN 1668, ODN 1826, ODN 2006, or ODN 2007. In embodiments, the TLR-binding DNA substituent is ODN 2395 or ODN M362. In embodiments, the TLR-binding DNA substituent is a derivative of ODN 1585, ODN 2216, ODN D19, ODN 2336, ODN 1668, ODN 1826, ODN 2006, ODN 2007, ODN 2395 or ODN M362. In embodiments, a derivative of ODN 1585, ODN 2216, ODN D19, ODN 2336, ODN 1668, ODN 1826, ODN 2006, ODN 2007, ODN 2395 or ODN M362 includes one or more (e.g., 1, 2, 3, 4, 5, 6, 7, 8, 9, or 10) nucleotide substitutions (e.g., A, C, G, or T substituted with a different nucleotide). In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, or 10) internucleotide linkage replacements (e.g., phosphodiester replaced with a phosphodiester derivative or a phosphodiester derivative replaced with a phosphodiester). In embodiments, a derivative of ODN 1585, ODN 2216, ODN D19, ODN 2336, ODN 1668, ODN 1826, ODN 2006, ODN 2007, ODN 2395 or ODN M362 includes one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide deletions. In embodiments, a derivative of ODN 1585, ODN 2216, ODN D19, ODN 2336, ODN 1668, ODN 1826, ODN 2006, ODN 2007, ODN 2395 or ODN M362 includes one or more (e.g., 1, 2, 3, 4, 5, 6, 7, 8, 9, or 10) nucleotide additions.

In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages). In embodiments, the compound includes a plurality of phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof). In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the TLR9-binding DNA substituent. In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the TLR-binding nucleic acid (e.g., endosomal TLR-, TLR3-, TLR7-, TLR8-, or TLR9-binding nucleic acid) substituent.

In embodiments, the phosphodiester derivative linkage in the compound may be phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage.

In embodiments, one or more of the nucleic acid internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g., 1, 2, 3, 4, 5, 6, 7, 8, 9, 10, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)).

In embodiments, provided herein is a compound linking a CpG-ODN to an anti-miR targeting miR-126 or an miRNA-mimic of miR-142.

In embodiments, provided herein is a compound linking a CpG-ODN to an anti-miR targeting miR-155.

In embodiments, provided herein is a compound linking a CpG-ODN to an anti-miR targeting miR-125b.

In embodiments, provided herein is a compound linking a CpG-ODN to an anti-miR targeting miR-146a or an miRNA-mimic of miR-146a.

In embodiments, the CpG-ODN conjugated to an anti-miR or miRNA-mimic is present in the cytoplasm (and in the cell nucleus).

Pharmaceutical Composition

In one aspect, provided herein is pharmaceutical compositions including a pharmaceutically acceptable excipient and a compound disclosed herein. In embodiments, the composition includes a second therapeutic agent. In embodiments, the second therapeutic agent is a anti-tumor or anti-cancer agent, anti-angiogenic agent, cytotoxic agent, cytostatic agent, anti-inflammatory agent, analgesic, anti-infective agent, growth inhibitory agent, immunogenic agent, immunomodulatory agent, or a chemokine. In embodiments, an anti-tumor or anti-cancer agent in the pharmaceutical composition of the present disclosure is a cell death promoting agent.

In embodiments, the second therapeutic agent in the pharmaceutical composition of the present disclosure includes a second therapeutic agent, for example ctinomycin D/Dactinomycin, Bleomycin, Daunorubicin, Doxorubicin, Doxorubicin (pegylated liposomal), Epirubicin, Idarubicin, Mitomycin, Mitoxantrone, Etoposide, Docetaxel, Irinotecan, Paclitaxel, Topotecan, Vinblastine, Vincristine, Vinorelbine, Carboplatin, Cisplantin, Oxaliplatin, Alemtuzamab, BCG, Bevacizumab, Cetuximab, Denosumab, Erlotinib, Gefitinib, Imatinib, Interferon, Ipilimumab, Lapatinib, Monomethyl auristatin E (MMEA), Mertansine (DM1), Rituximab, Sunitinib, Sorafenib, Temsirolimus, Trastuzumab, or any combination(s) thereof.

In embodiments, the present disclosure includes compositions of a combination of a compound of the present disclosure with one or more additional anti-cancer therapies, e.g., an anti-VEGF antibody, or anti-STAT agents.

In embodiments of any of the methods and uses, the disclosure includes treating cancer, by administering effective amounts of a compound of the present disclosure and a chemotherapeutic agents to a subject diagnosed with cancer. A variety of chemotherapeutic agents may be used in the combined treatment methods and uses of the present disclosure. In embodiments, the chemotherapeutic agent may be temolozolomide. In embodiments, the chemotherapeutic agent may be administered concommitantly with radiotherapy.

In one example, the combined treatment may involve administration which includes simultaneous administration, using separate formulations or a single pharmaceutical formulation, and consecutive administration in either order, where there may be a time period when both (or all) active agents simultaneously exert their biological activities. Preparation and dosing schedules for such chemotherapeutic agents may be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). The chemotherapeutic agent may precede, or follow administration of a compound or composition of the present disclosure or may be given simultaneously therewith.

In embodiments of any of the methods and uses, other therapeutic agents useful for combination tumor therapy with a compound of the present disclosure include antagonist of other factors that are involved in tumor growth, such as VEGF, EGFR, ErbB3, ErbB4, STAT or TNF. Sometimes, it may be beneficial to also administer one or more cytokines to the subject. In embodiments, a compound or composition of the present disclosure is co-administered with a growth inhibitory agent. For example, the growth inhibitory agent may be administered first, followed by the compound or composition of the present disclosure. However, simultaneous administration or administration of a compound or composition of the present disclosure first may be possible. Suitable dosages for the growth inhibitory agent are those presently used and may be lowered due to the combined action (synergy) of the growth inhibitory agent and a compound of the present disclosure.

The composition herein may also contain more than one active compound as necessary for the particular indication being treated, e.g., those with complementary activities that do not adversely affect each other. For example, it may be desirable to further provide agents which bind to EGFR, VEGF (e.g., an antibody which binds a different epitope or same epitope on VEGF), VEGFR, or ErbB2 in the one formulation. Such molecules may be suitably present in combination in amounts that are effective for the purpose intended.

In embodiments of the methods and uses, other therapeutic agents useful for combination cancer therapy with a compound or composition of the present disclosure include other anti-angiogenic agents. Many anti-angiogenic agents have been identified and are known in the arts, including those listed by Carmeliet and Jain (2000). In embodiments, a compound or composition of the present disclosure is used in combination with another miR antagonist, neutralizing antibodies against miR complex, low molecule weight inhibitors of miR, and any combinations thereof.

The present disclosure includes compositions with an effective dose of a compound of the present disclosure. The effective dose may be between about 0.001 mg/kg to about 100 mg/kg of the agent (e.g., 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/kg).

In embodiments, an effective dose of a compound including an anti-miR, e.g., anti-miR126, of the present disclosure is administered to a subject in need thereof for treating a disease (e.g., a cancer, an autoimmune disease or an infectious disease). The anti-miR suppresses expression/activity of a miR (e.g., miR126) in a cell, and induces the cancer cell (e.g., leukemia stem cell (LSC)) to undergo cell cycle, and render the cancer cell (e.g., LS) more sensitive to chemotherapy.

In embodiments, an effective dose of a compound including a miR-mimic, e.g., miR142-mimic, of the present disclosure is administered to a subject in need thereof for treating a disease (e.g., a cancer, an autoimmune disease or an infectious disease). The miR-mimic blocks cancer, e.g., leukemia, development.

The compound may be administered to a subject in need thereof, at a dose between about 0.001 mg/kg to about 0.01 mg/kg of the compound, between about 0.01 mg/kg to about 0.1 mg/kg of the compound, between about 0.1 mg/kg to about 1.0 mg/kg of the compound, between about 1.0 mg/kg to about 5.0 mg/kg of the compound, between about 5.0 mg/kg to about 10 mg/kg of the compound, between about 10 mg/kg to about 15 mg/kg of the compound, between about 15 mg/kg to about 20 mg/kg of the compound, between about 20 mg/kg to about 25 mg/kg of the compound, between about 25 mg/kg to about 30 mg/kg of the compound, between about 30 mg/kg to about 35 mg/kg of the compound, between about 35 mg/kg to about 40 mg/kg of the compound, between about 40 mg/kg to about 45 mg/kg of the compound, between about 45 mg/kg to about 50 mg/kg of the compound, between about 50 mg/kg to about 55 mg/kg of the compound, between about 55 mg/kg to about 60 mg/kg of the compound, between about 60 mg/kg to about 65 mg/kg of the compound, between about 65 mg/kg to about 70 mg/kg of the compound, between about 70 mg/kg to about 75 mg/kg of the compound, between about 75 mg/kg to about 80 mg/kg of the compound, between about 80 mg/kg to about 85 mg/kg of the compound, between about 85 mg/kg to about 90 mg/kg of the compound, between about 90 mg/kg to about 95 mg/kg of the compound, or between about 95 mg/kg to about 100 mg/kg of the compound.

In embodiments, the present disclosure includes compositions with an effective dose of a compound of the present disclosure in which the compound may be between about 0.1% to about 20% w/v of the composition.

For example, the effective dose of a compound disclosed herein may be between about 0.001%-about 0.01%, between about 0.01%-about 0.1%, between about 0.1%-about 1.0%, between about 1.0%-about 2.0%, between about 2.0%-about 3.0%, between about 3.0%-about 4.0%, between about 4.0%-about 5.0%, between about 5.0%-about 6.0%, between about 6.0%-about 7.0%, between about 7.0%-about 8.0%, between about 8.0%-about 9.0%, between about 9.0%-about 10%, between about 10%-about 11%, between about 11%-about 12%, between about 12%-about 13%, between about 13%-about 14%, between about 14%-about 15%, between about 15%-about 16%, between about 16%-about 17%, between about 17%-about 18%, between about 18%-about 19%, or between about 19%-about 20% w/v of the composition.

Methods of Treatment or Use

Provided herein is a method of treating a disease in a subject in need thereof, the method including administering to the subject an effective amount of a compound or the pharmaceutical composition including a compound disclosed herein. In embodiments, the disease is a cancer, an autoimmune disease or an infectious disease.

In embodiments, the cancer may be a hematopoietic cell cancer. In embodiments, the cancer is not a hematopoietic cell cancer. In embodiments, the cancer is myeloma or acute myeloid leukemia or chronic myeloid leukemia. In embodiments, the cancer is prostate cancer, breast cancer, glioblastoma, ovarian cancer, lung cancer, head and neck cancer, esophageal cancer, skin cancer, melanoma, brain cancer, colorectal cancer, leukemia, lymphoma, or myeloma.

In embodiments, the autoimmune disease is rheumatoid arthritis, psoriasis, systemic lupus erythematosus (SLE), type II diabetes, non-alcoholic fatty liver disease, non-alcoholic steatohepatitis, multiple sclerosis (MS), Parkinson's disease (PD, Alzheimer's disease (AD) or inflammatory bowel disease (IBD).

In embodiments, the infectious disease is tuberculosis, influenza, Ebola, HIV, HPV infection or hepatitis.

In embodiments, the compound or the composition is administered to the subject by intravenous, parenteral, subcutaneous, intramuscular, transdermal, intraperitoneal, intranasal, aerosol, oral, or topical administration. In embodiments, the treatment is dose-dependent of the compound or composition. In embodiments, about 0.001 mg/kg to about 100 mg/kg of the compound is administered to the subject. All digits and various ranges within this range are also implied.

Provided herein is a method of suppressing miR, e.g., miR126, in a cell, the method including contacting the cell with an effective amount of a compound or a pharmaceutical composition of a compound disclosed herein. Provided herein is a method of inhibiting cell growth including contacting the cell with an effective amount of a compound or a pharmaceutical composition of a compound disclosed herein.

In embodiments, the cell is a cancer cell. In embodiments, the cell is an acute myeloid lymphoid (AML) cell or a chronic myeloid leukemia cell (CML). In embodiments, the AML cell is from the bone marrow. In embodiments, the cell is a cultured cell in vitro; the cell is in situ in a host; the cell is in a cultured tissue ex vivo. In embodiments, the contacting step is free of viral transduction. In embodiments, the contacting step is free of viral transduction and the cell is contacted with a compound of the present disclosure or a pharmaceutical composition including a compound of the present disclosure. In embodiments the cell is contacted with about 1 nanomole to about 100 nanomoles (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nm) of the compound. All digits and various ranges within this range are also implied.

In embodiments, the heteroalkylene linker allow for further modification, conjugation, or attachment of additional moieties after completion of the synthesis and while the oligonucleotide is still attached to the support.

In embodiments, provided herein is a CpG-ODN conjugated to an anti-miR or miRNA-mimic with a substituted (e.g. substituted with a substituent group, size-limited substituent group or lower substituent group) heteroalkylene linker, which may allow further modification, conjugation, or attachment during synthesis and while the oligonucleotide is attached to a support.

In embodiments, the substituted (e.g. substituted with a substituent group, size-limited substituent group or lower substituent group) heteroalkylene linker is modified, conjugated, or attached to substituents. A modification may include the conversion of the original substituent into a different substituent. For example, a bromo-alkane substituent may be converted into an azido-alkane. Conjugation may result in bonding of two large moieties together. For example, an NHS derivative may be conjugated with PEG-NH$_2$. A peptide may also be conjugated with an oligonucleotide or an antibody may be conjugated to an oligonucleotide. Attachment may result in bonding of the small molecule to a large molecule. For example, NHS-ester of biotin might be attached to the amino derivative of an oligo.

In embodiments, provided herein is a compound having CpG-ODN conjugated to an anti-miR or miRNA-mimic with linkers multiple different linkers, multiple identical linkers, or a substitution of linkers selected from the following groups:

Fmoc amino-modifier C6 dT (introduction of the amino group) which can be further used for functionalization, by reacting with NHS ester and divinyl sulfone and its analogues.

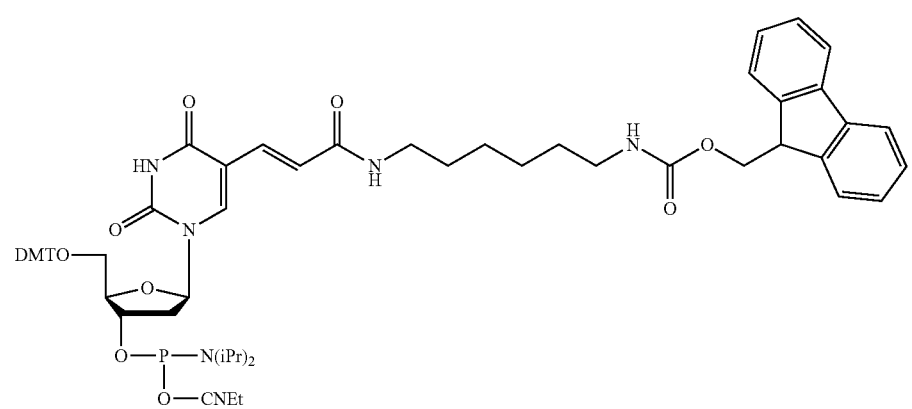

S-Bz-thiol-modifier C6-dT (introduction of sulfuhydryl group), which can be further used for functionalization by reacting with divinyl sulfone and acrylic analogues.

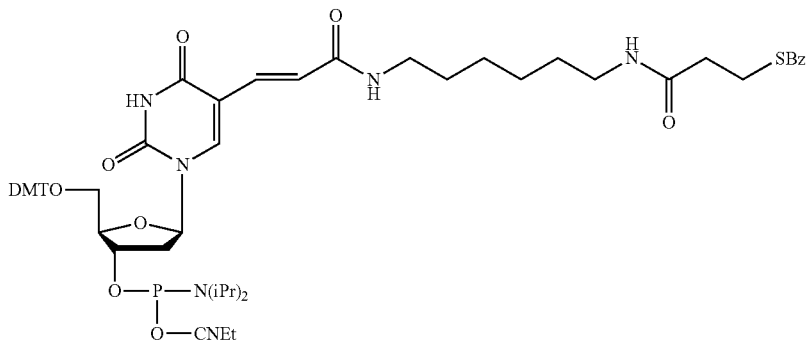

Amino-modifier Serinol Phosphoramidite (introduction of the amino group) which can be further be used for functionalization, by reacting with NHS ester and divinyl sulfone and its analogues.

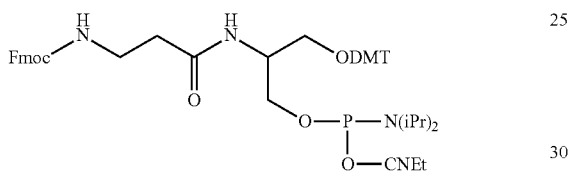

DBCO-dT (introduction of alkyne, copper free Click Chemistry) which can be further used for functionalization with azido-reactants

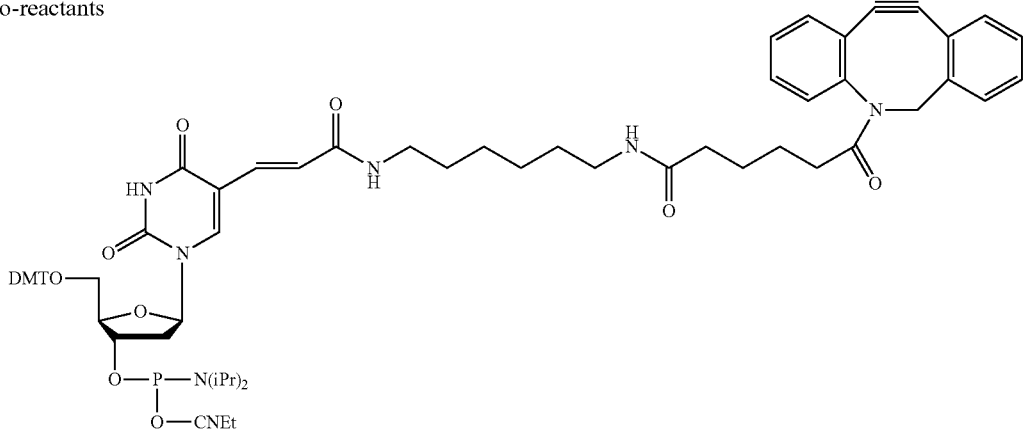

DBCO-sulfo-NHS Ester (introduction of the of alkyne, copper free Click Chemistry, by reacting with the amino groups)

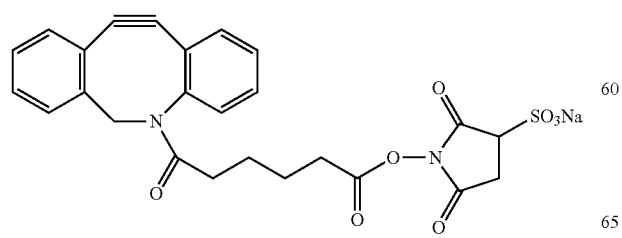

EXAMPLES

Example 1: Uptake of CpG-Anti-miR126 Inhibitor in Normal, Cord Blood, AML and CML CD34+ Cells Normal, cord blood, AML and CML CD34+ cells were cultured with CpG-anti-miR126 inhibitor-Cy3 or anti-miR126 inhibitor-Cy3 for 16 hours, and the uptake was measured by Cy3 expression in the cells by flow cytometry (FIGS. 2A-2D). All tested cells internalized CpG-anti-miR126-Cy3 but not the anti-miR126-Cy3 with high efficiency.

Figure 3A:
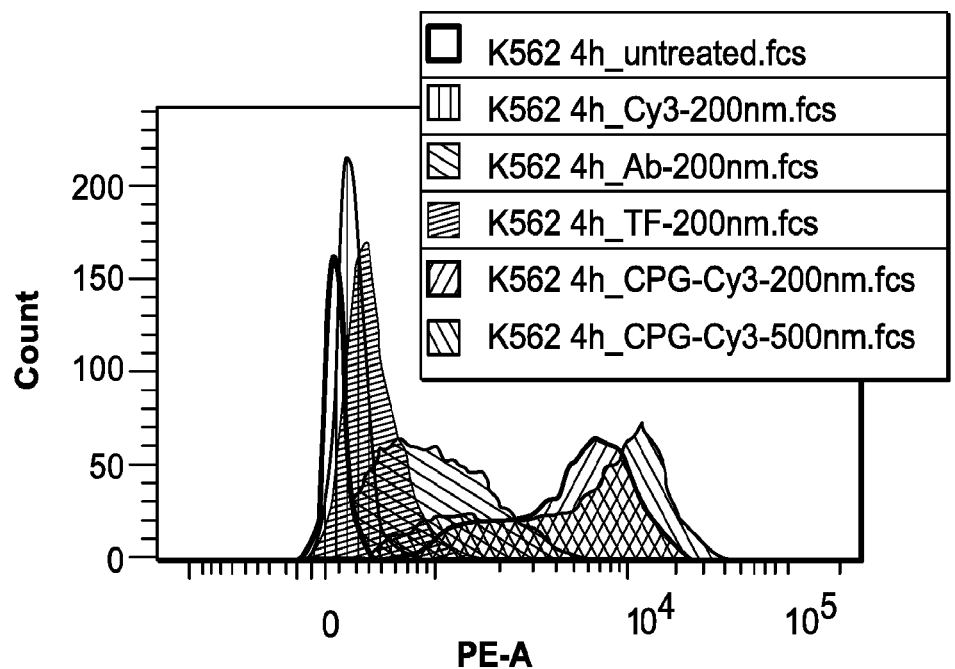
FIGS. 3A-3G are flow cytometry histograms showing results of CpG-anti-miR-126 uptake in AML and CML cell lines. Cells were cultured with miR126-inhibitor-Cy3 (Cy3-200 nM0, human CD45 (Ab-200 nM) or Transferrin (TF-200 nM)-conjugated nanoparticles (NP) containing antagomiR-126-Cy3, CpG-miR126 inhibitor-Cy3 (CpG-Cy3-200 nM and 500 nM) for 4 hours, then uptake was analyzed by measuring Cy3 expression in these cells by flow cytometry.
Figure 3B:
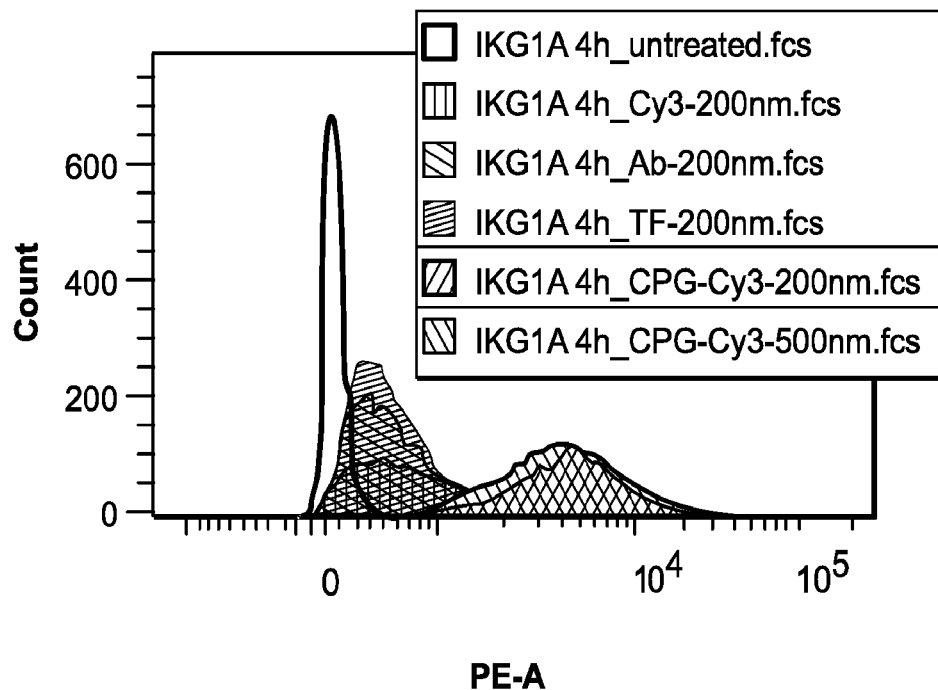
Figure 3C:
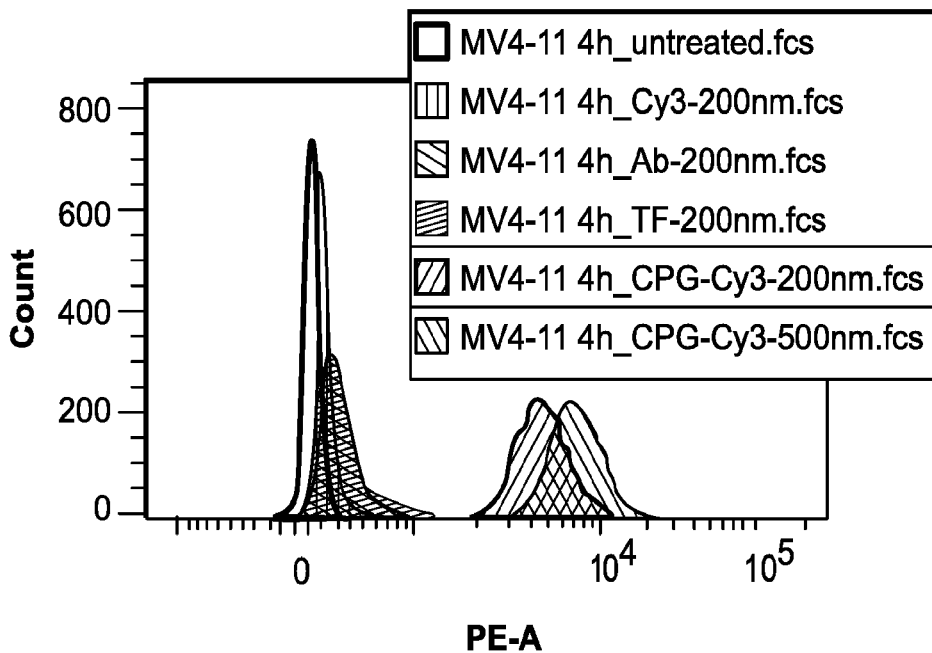
Figure 3D:
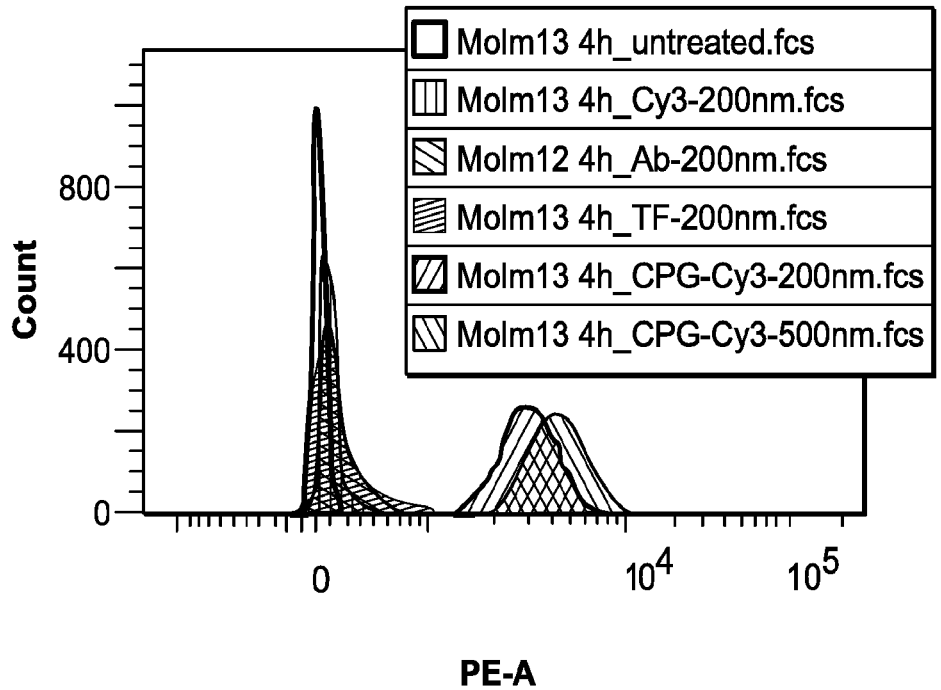
Figure 3E:
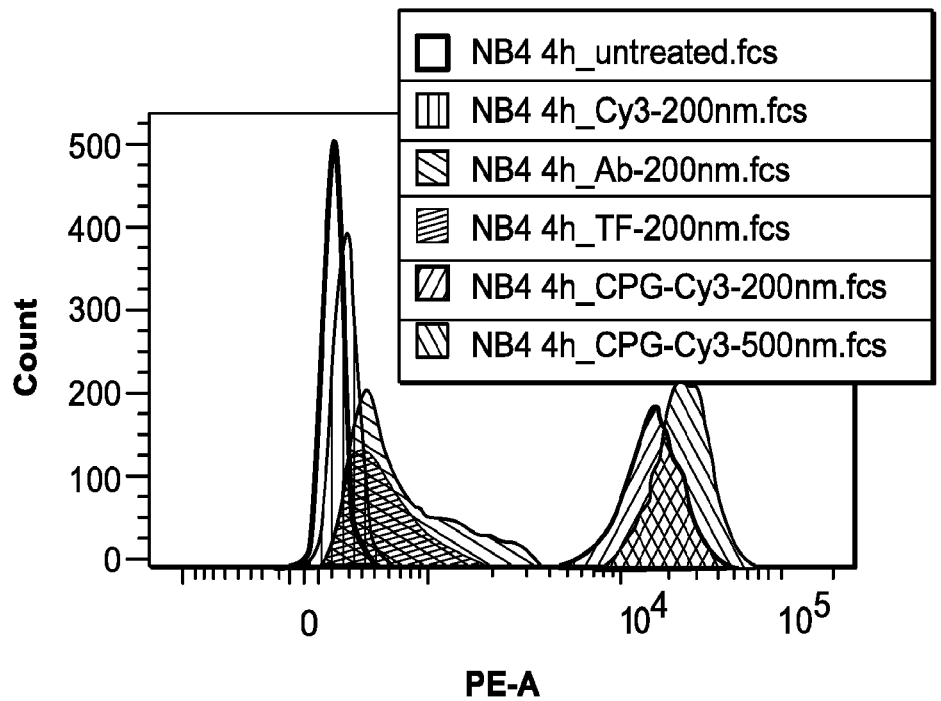
Figure 3F:
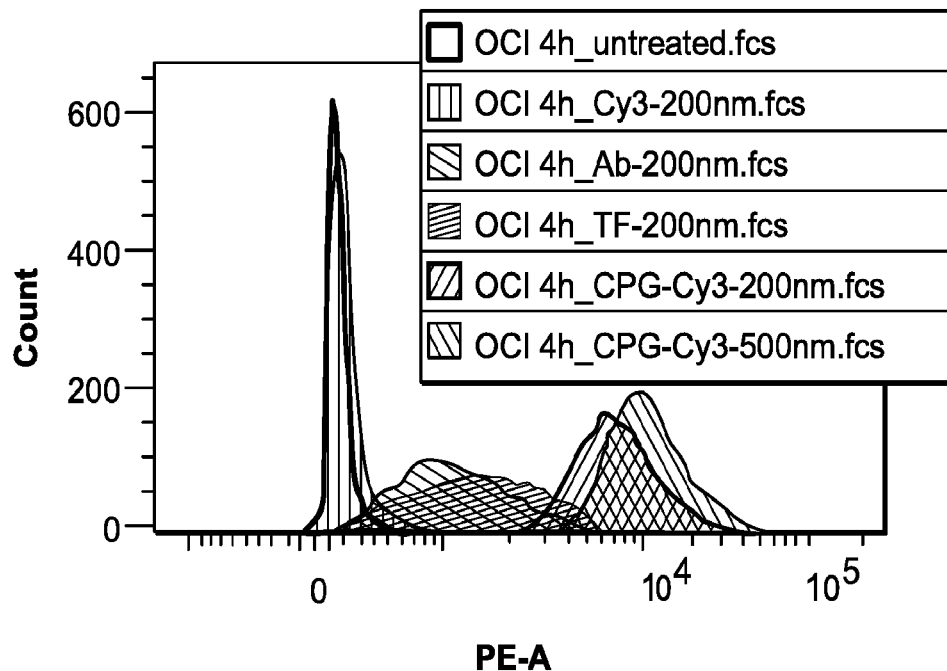
Figure 3G:
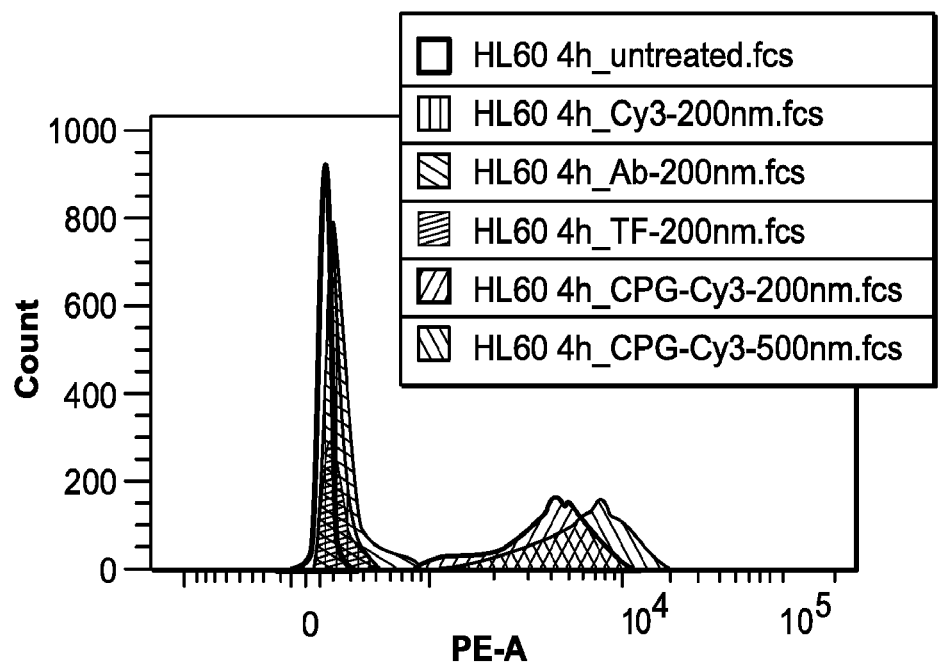
Figure 4B:
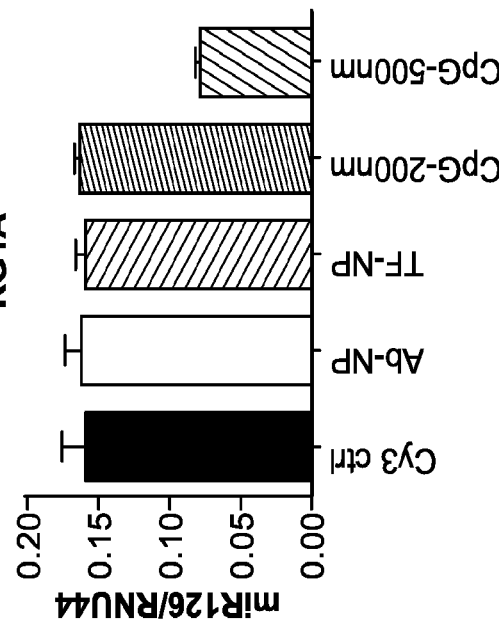
FIGS. 4A-4G are bar graphs showing miRNA 126 expression in AML and CML cell lines. Cells were cultured with miR126-inhibitor-Cy3 (Cy3-200 nM0, human CD45 (Ab-200 nM) or Transferrin (TF-200 nM)-conjugated NP containing antagomiR-126-Cy3, CpG-miR126 inhibitor-Cy3 (CpG-Cy3-200 nM and 500 nM) for 24 hours, then miR126 and RNU44 (control) expression in these cells was analyzed by q-RT PCR. The miR126 expression levels were normalized to RNU44 and calculated by using the comparative $2^{-\Delta\Delta Ct}$ method.
Figure 4A:
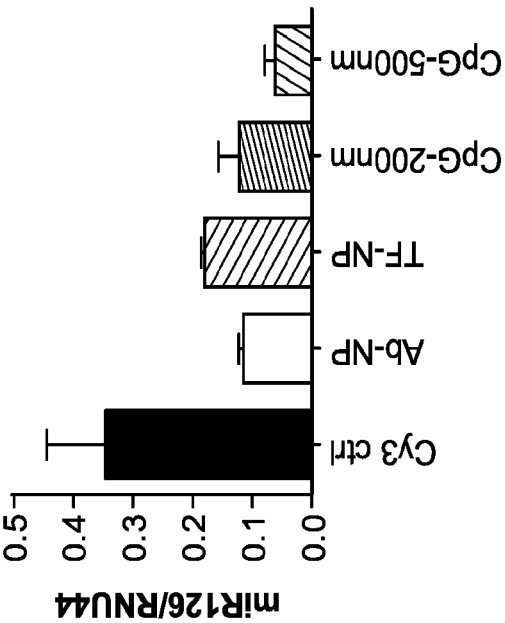
Figure 4D:
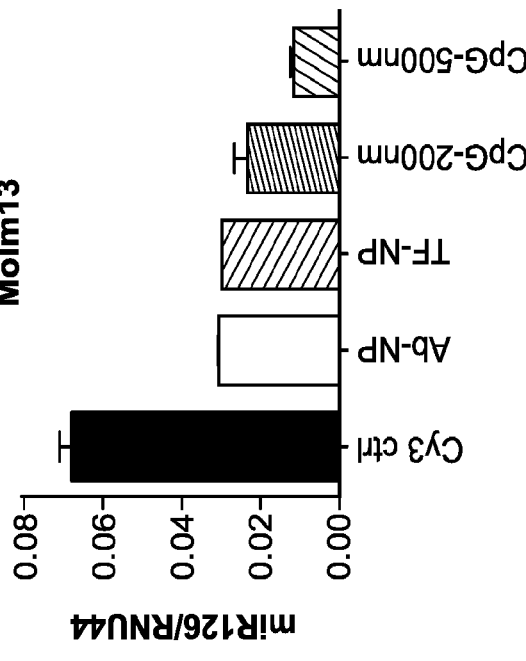
Figure 4C:
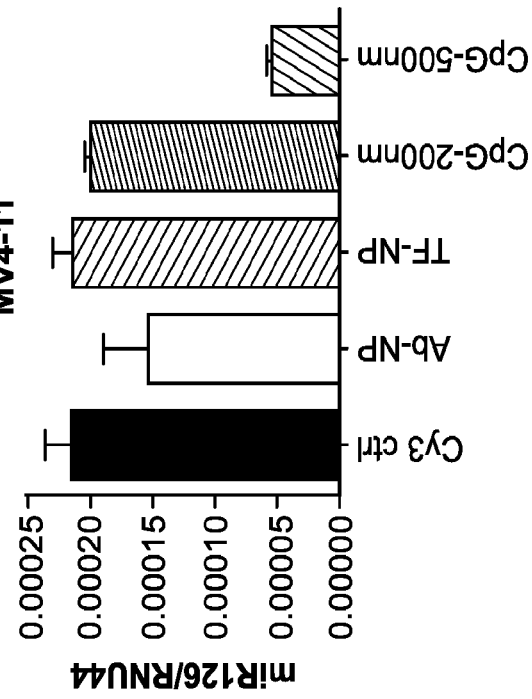
Figure 4E:
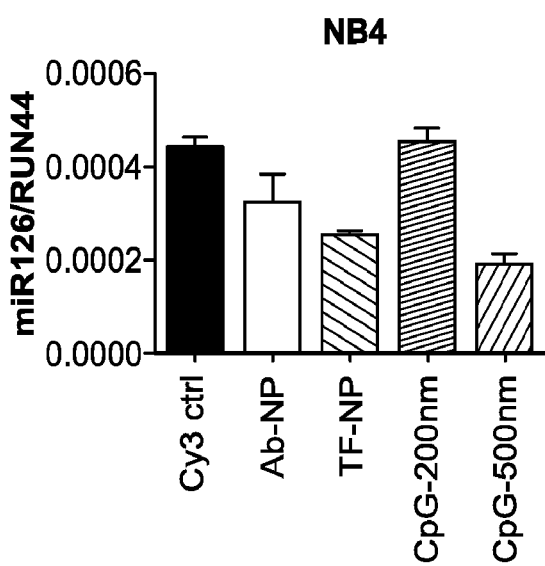
Figure 4F:
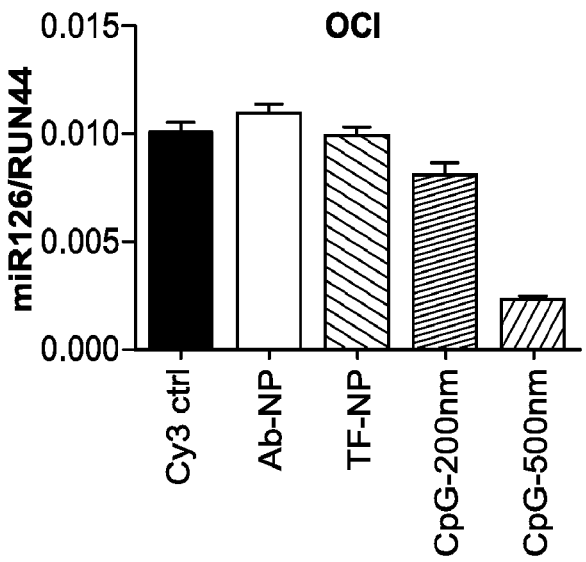
Figure 4G:
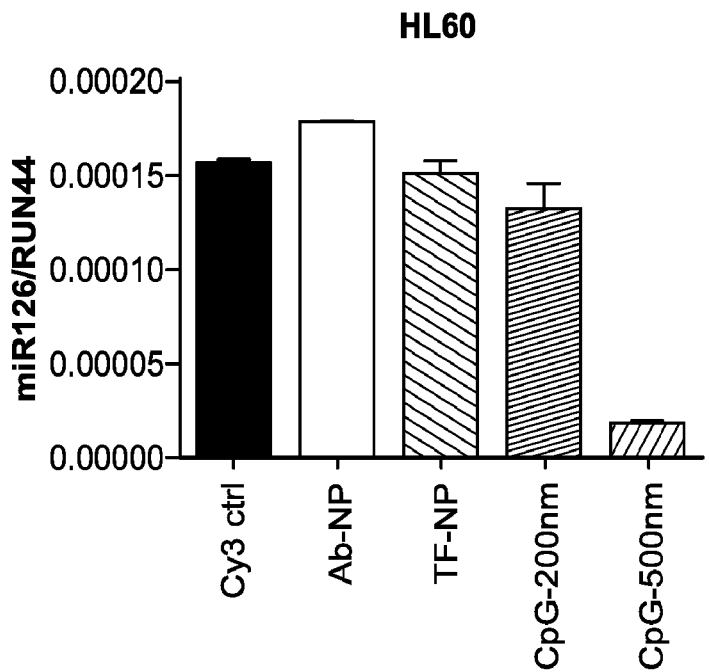

Example 2: Uptake and Expression of CpG-Anti-miR126 Inhibitor in AML and CML Cell Lines CML (K562) (FIG. 3A) and AML cell lines (KG1A, MV4-11, Molm13, NB4, OCI and HL60) (FIGS. 3B-3G) were cultured with anti-miR126 inhibitor-Cy3 (Cy3-200 nM) alone, human CD45 (Ab-200 nM) or Transferrin (TF-200 nM)-conjugated nanoparticles (NP) containing anti-miR126-Cy3 or unformulated CpG-anti-miR126 inhibitor-Cy3 in two concentrations (200 nM and 500 nM) for 4 hours, the uptake was analyzed by measuring Cy3 expression in these cells by flow cytometry. The myeloid cell-specific CpG-anti-miR126 conjugate was quickly and dose-dependently internalized by a variety of human AML and CML cell lines in vitro. The level of CpG-anti-miR126 internalization in absence of any transfection regents exceeded that of all other oligonucleotides including NP-formulated anti-miR126 inhibitor miRNA 126 expression in AML and CML lines was evaluated. CML (K562) (FIG. 4A) and AML cell lines (KG1A, MV4-11, Molm13, NB4, OCI and HL60) (FIGS. 4B-4G) were cultured with anti-miR126 inhibitor-Cy3 (Cy3 ctrl, 200 nM), human CD45 (Ab-NP, 200 nM) or Transferrin (TF-NP, 200 nM)-conjugated NP containing anti-miR-126-Cy3, or CpG-anti-miR126 inhibitor-Cy3 (CpG-200 nM and 500 nM) for 24 hours, then miR126 and RNU44 (control) expression in these cells were analyzed by Q-RT-PCR. The myeloid cell-specific CpG-anti-miR-126 conjugate (500 nM) leds to the most effective downregulation of miRNA126 in all the tested human AML and CML cell lines in vitro, with more than 50% reduction of target miRNA expression in HL60, K562, MV4-11, MOLM13 and OCI cells

Example 3: miRNA126 Expression in NL/CB, AML and CML CD34+ Cells

Figure 5:
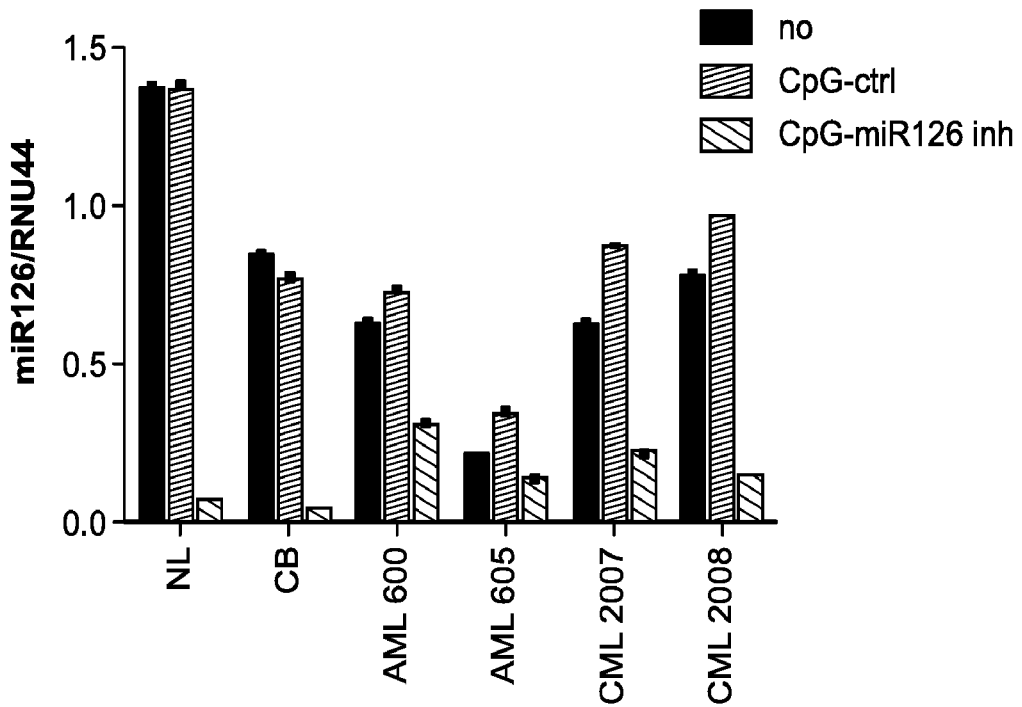
FIG. 5 is a bar graph showing the expression of miRNA 126 in NL/CB, AML and CML CD34+ cells. Normal, cord blood, AML and CML CD34+ cells were cultured with CpG-scramble RNA (500 nM) and CpG-miR 126 inhibitor-Cy3 (500 nM) for 24 hours. miR126 and RNU44 (control) expression was analyzed by q-RT-PCR. The miR126 expression levels were normalized to RNU44 and calculated by using the comparative $2^{-\Delta\Delta Ct}$ method.

Normal, cord blood, AML and CML CD34+ cells were cultured with CpG-scramble RNA (500 nM) and CpG-anti-miR126 inhibitor-Cy3 (500 nM) for 24 hours, and then miR126 and RNU44 (ctrl) expression in these cells were analyzed by Q-RT-PCR (FIG. 5). The miR126 expression levels were normalized to RNU44 and calculated by using the comparative $2^{-\Delta\Delta Ct}$ method. The myeloid cell-specific CpG-anti-miR-126 conjugate (500 nM) was quickly internalized by a variety of primary patients' AML and CML CD34+ cells in vitro and significant reduction of miR126 expression (60%-90% reduction) was seen in these cells.

Figure 6:
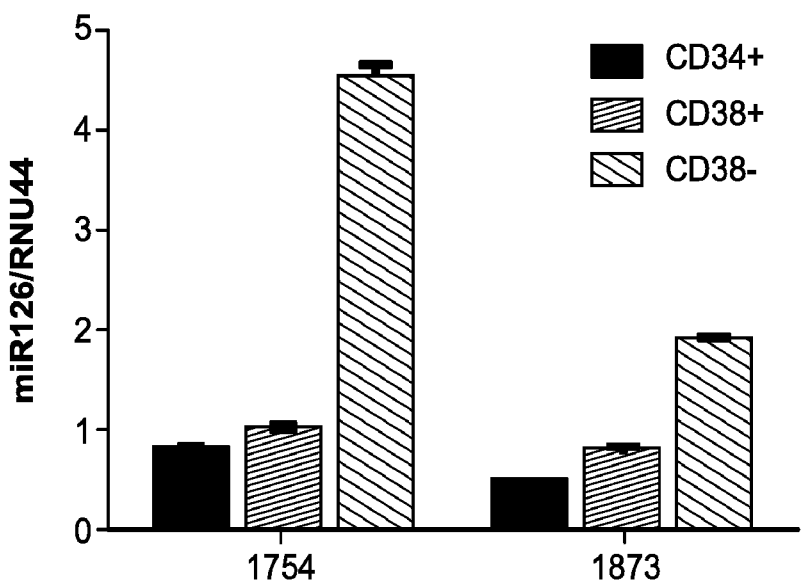
FIG. 6 is a bar graph showing higher expression of miR126 in CML CD34+CD38-primitive progenitors compared to CD34+CD38− committed progenitors. CML CD34+, CD34+CD38+ committed and CD34+CD38− primitive progenitors were sorted and then miR126 and RNU44 (ctrl) expression in these cells were analyzed by Q-RT-PCR. The miR126 expression levels were normalized to RNU44 and calculated by using the comparative 2-ΔΔCt method.

Example 4: CML CD34+CD38− Primitive Progenitors Showed Higher miR126 Expression than CD34+CD38+ Committed Progenitors CML CD34+, CD34+CD38+ committed and CD34+CD38− primitive progenitors were sorted and then miRNA126 and RNU44 (control) expression in these cells were analyzed by Q-RT-PCR. The miR126 expression levels were normalized to RNU44 and calculated by using the comparative $2^{-\Delta\Delta Ct}$ method (FIG. 6). CML CD34+CD38− primitive progenitors showed higher miR126 expression than CD34+CD38+ committed progenitors.

Figure 7:
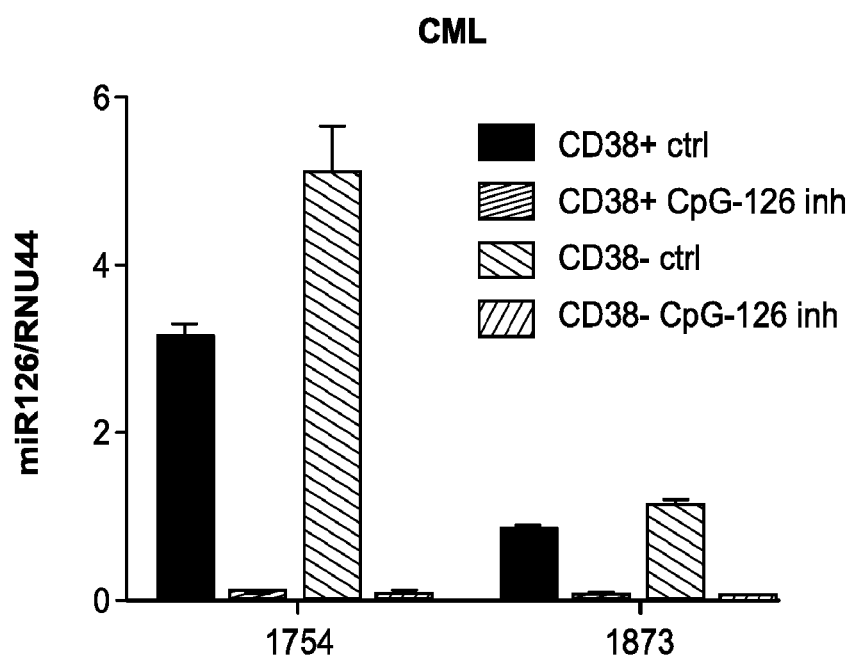
FIG. 7 is a bar graph showing that miR126 expression was significantly reduced in CML CD34+CD38+ committed and CD34+CD38− primitive cells treated with CpG-mirR126 inhibitor. CML CD34+CD38+ committed and CD34+CD38− primitive progenitors were cultured with CpG-scramble RNA (500 nM) or CpG-miR126 inhibitor (500 nM) for 36 hours and then miR126 and RNU44 (control) expression in these cells were analyzed by q-RT-PCR. The miR126 expression levels were normalized to RNU44 and calculated by using the comparative $2^{-\Delta\Delta Ct}$ method.
Figure 8:
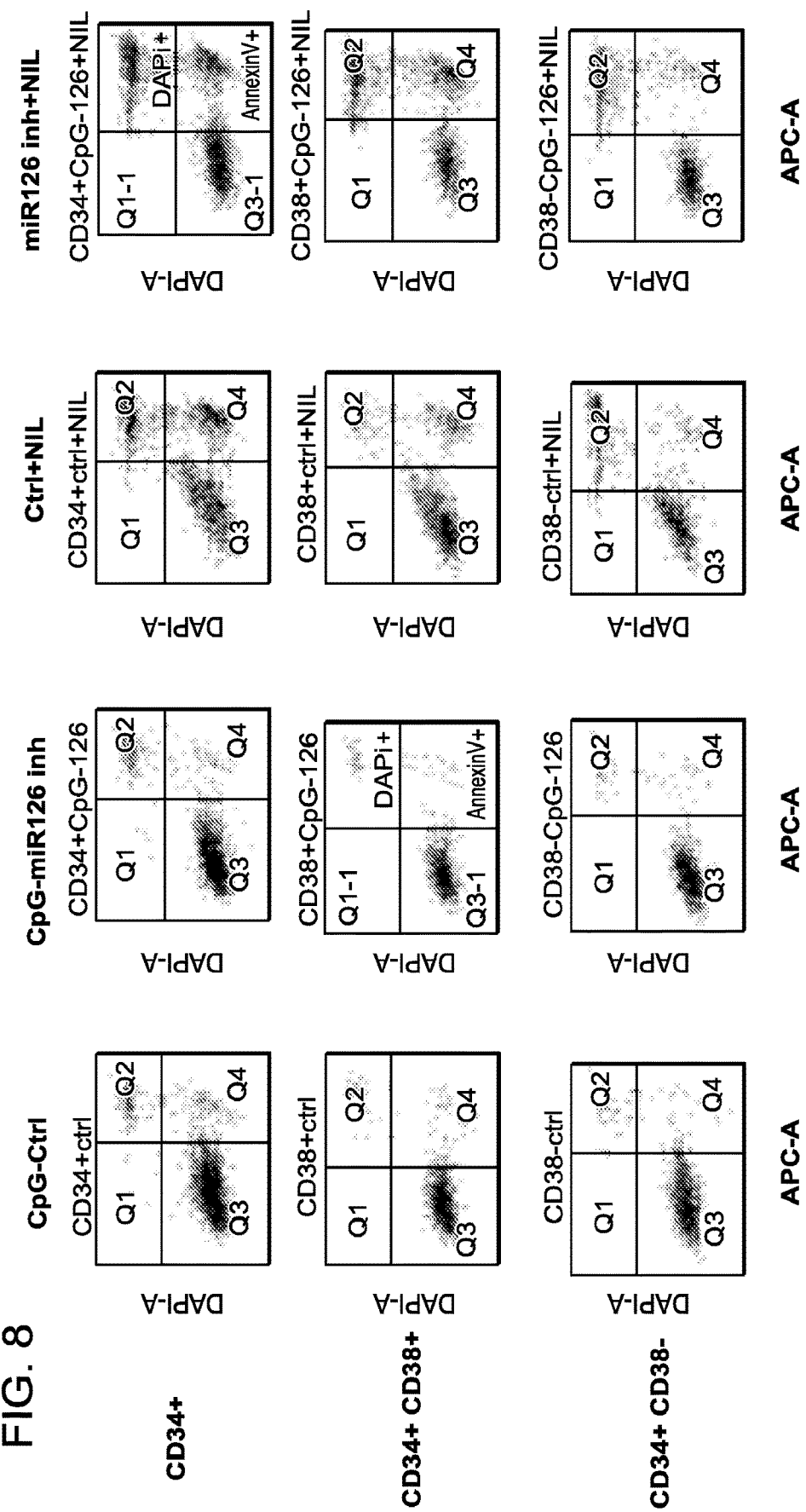
FIG. 8 is a series of plots showing increased apoptosis of CML CD34+, CD34+CD38+ committed and CD34+CD38− primitive progenitors treated with CpG-miR126 inhibitor and Nilotinib (NIL). CML CD34+, CD34+CD38+ committed and CD34+CD38− primitive progenitors were cultured with CpG-scramble RNA (500 nM), CpG-miR126 inhibitor (500 nM), CpG-scramble RNA (500 nM)+Nilotinib (5 μM), and CpG-miR126 inhibitor (500 nM)+NIL (5 μM) for 72 hours and then apoptosis was analyzed by Annexin V/DAPI staining.
Figure 10A:
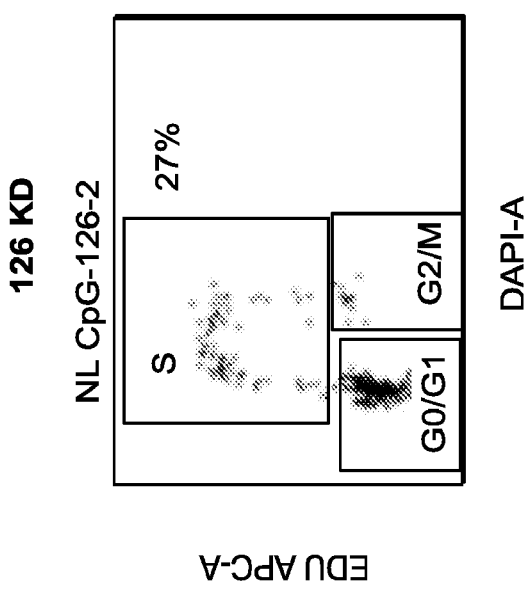
FIGS. 10A-D are a series of cell sorting plots showing increased cell cycling in normal (NL) and CML LTHSC after knockdown of miR-126. Normal (NL) and CML murine LTHSC (Lin-Sca-1+Kit+Fit3-CD150+CD48− cells) were sorted and then treated with 500 nm CpG-miR126 inhibitor or CpG-SCR for 72 hours, then cell cycling was analyzed by EDU/DAPi staining. Increased cell cycling was seen in NL and CML LTHSC after knockdown of miR-126 (FIG. 10D).
Figure 10B:
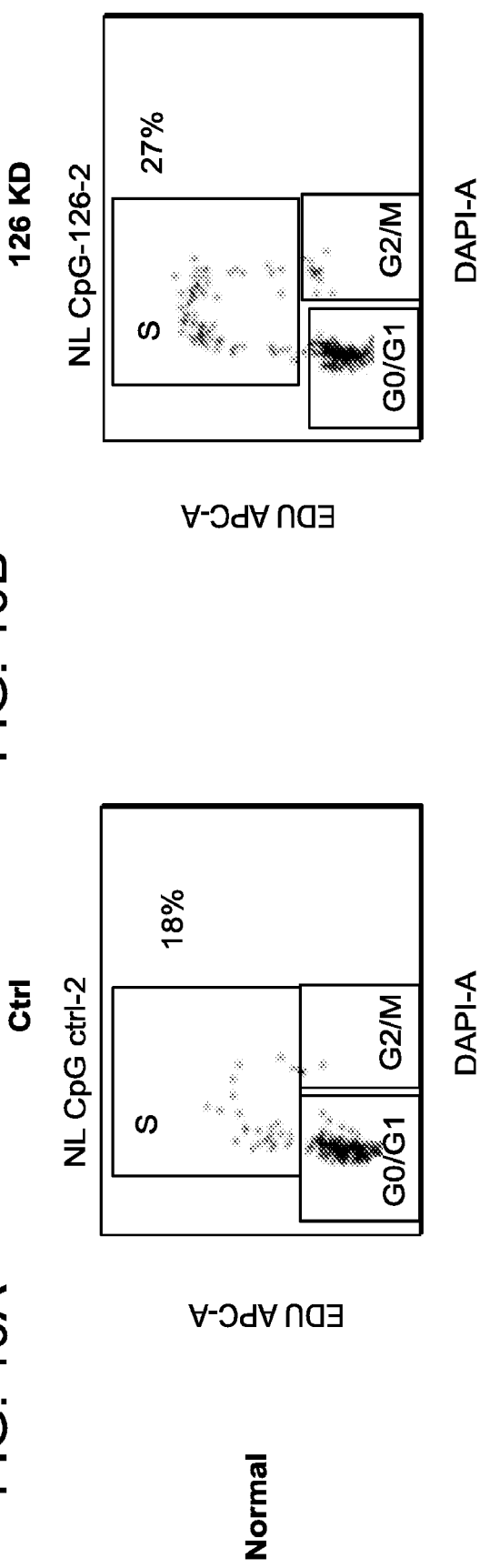
Figure 10C:
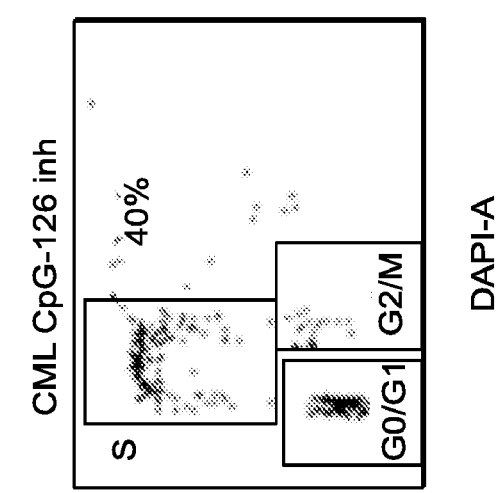
Figure 10D:
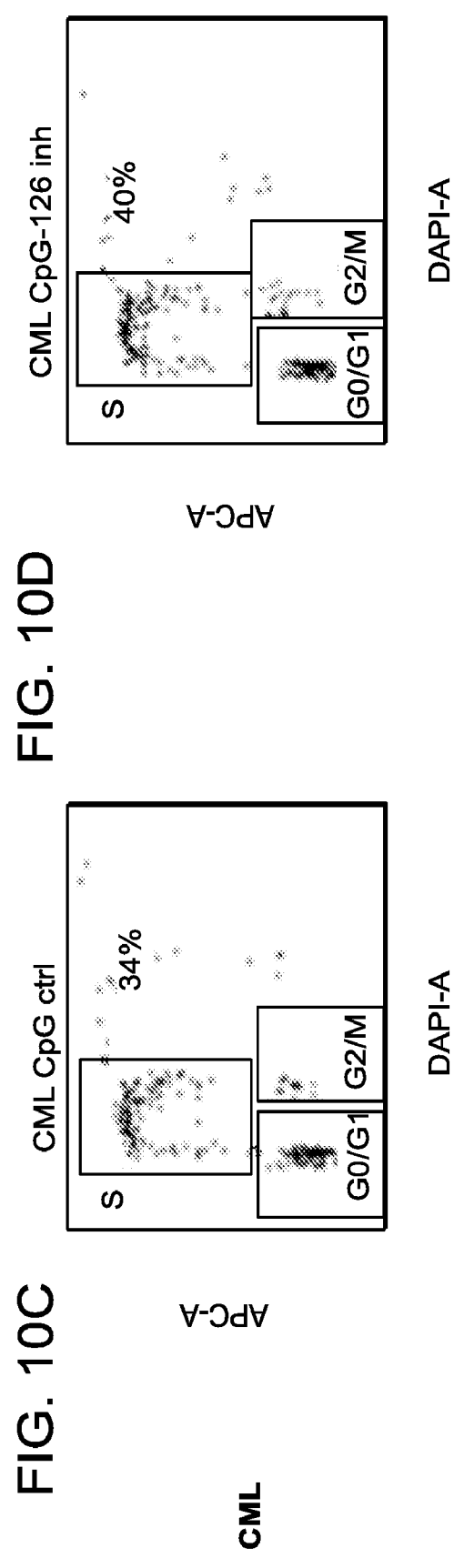

Example 5: Increased Apoptosis of CML CD34+, CD34+CD38+ Committed and CD34+CD38− Primitive Progenitors Treated with CpG-Anti-miR126 Inhibitor and NIL CML CD34+, CD34+CD38+ committed and CD34+CD38− primitive progenitors were cultured with CpG-scramble RNA (500 nM), CpG-anti-miR126 inhibitor (500 nM), CpG-scramble RNA (500 nM)+Nilotinib (NIL, 5 uM), and CpG-anti-miR126 inhibitor (500 nM)+NIL (5 uM) for 72 hours and then cell cycling and apoptosis were analyzed by EDU/DAPi and Annexin V/DAPi staining. More than 90% reduction of miR126 expression was seen in CpG-anti-miR126 inhibitor treated cells (FIG. 7). Increased apoptosis of CML CD34+, CD34+CD38+ committed and CD34+CD38− primitive progenitors treated with CpG-anti-miR126 inhibitor and NIL was observed, compared with the cells treated with CpG-scramble and NIL (FIG. 8). Increased cell cycling was seen in normal and CML CD34+CD38− primitive progenitors treated with CpG-anti-miR126 inhibitor (FIG. 9).

Figure 11A:
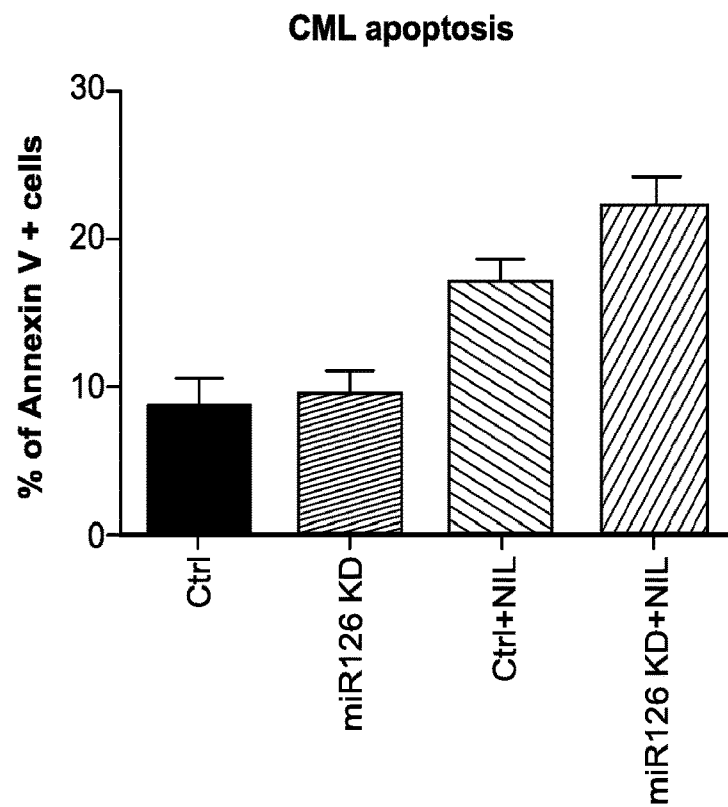
FIGS. 11A-B are bar graphs of cell sorting experiment showing significantly increased apoptosis and significant reduction of cell growth of LSC compared with SCR+NIL. Mouse CML leukemia stem cells (LSC, Lin-Sca-1+c-kit+Fit3-CD150+CD48−) were sorted and treated with CpG-anti-miR-126 inhibitor or CpG-SCR (500 nM) for 48 hours, then furthered treated with miR126 inhibitor+NIL or SCR+NIL for 72 hours, then apoptosis and cell growth were measured. CpG-anti-miR126 inhibitor+NIL resulted in significantly increased apoptosis (FIG. 11A) and significant reduction of cell growth (FIG. 11B) of LSC compared with SCR+NIL.
Figure 11B:
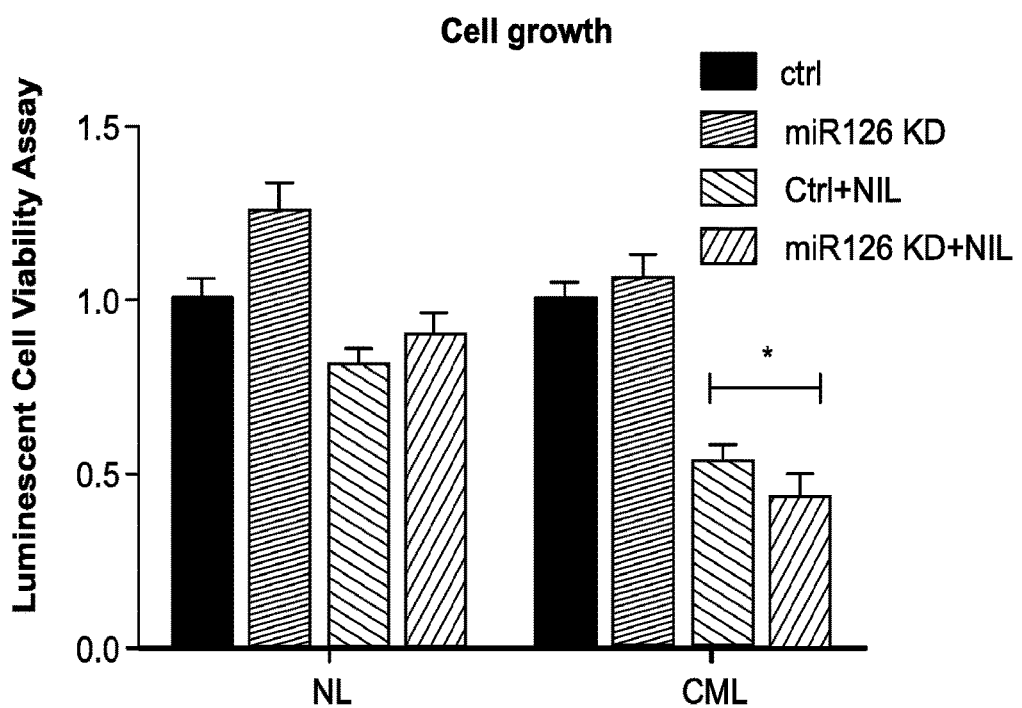

Moreover, incubation with CpG-anti-miR-126 inhibitor (500 nM) resulted in increased cell-cycle entry of long term hematopoietic stem cells (LTHSC, Lin-Sca-1+c-kit+Fit3-CD150+CD48-) from normal and CML mouse, measured by EDU/DAPi staining (FIG. 10), compared with the CpG-Scr. CpG-anti-miR126 inhibitor combined with NIL also resulted in significantly increased apoptosis (FIG. 11A) and significant reduction of cell growth (FIG. 11B) of LSC compared with CpG-SCR+NIL treatment.

Figure 12A:
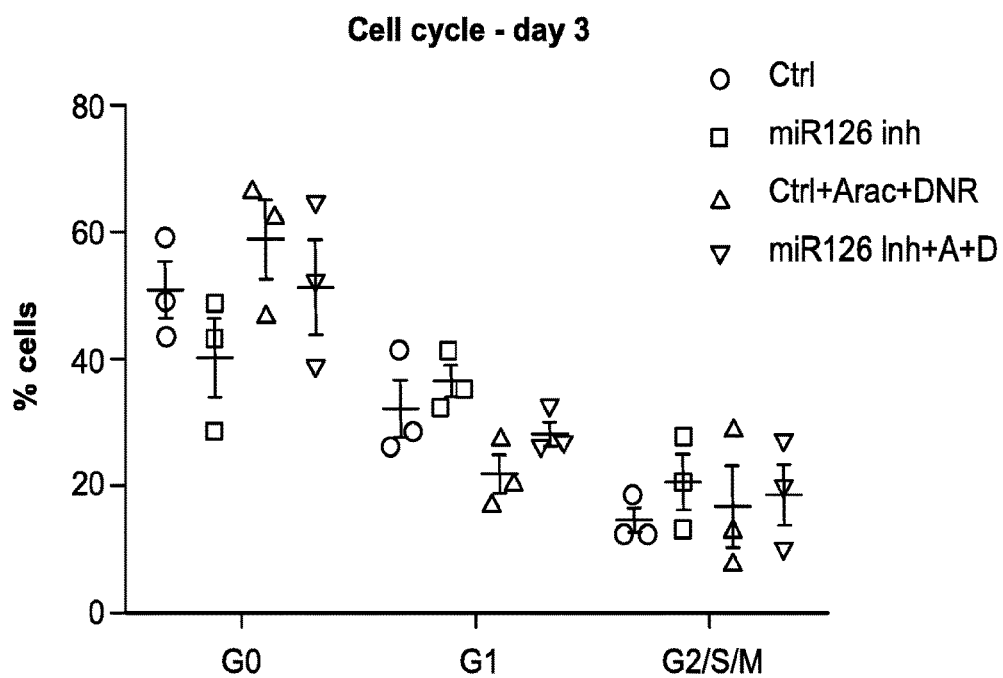
FIG. 12A is a scatter plot and FIGS. 12B-12C are bar graphs showing significantly increased cell cycling and apoptosis compared with SCR+Ara-c+Doxo, resulting in reduction of cell growth. AML CD34+ cells were cultured with CpG-anti-miR-126 or CpG-SCR (500 nM) for 48 hours, then furthered cultured with miR126 inh+Ara-c+Doxo or SCR+A+D for 72 hours, then cell cycling, apoptosis (FIG. 12B) and cell growth (FIG. 12C) were analyzed. CpG-anti-miR-126 inhibitor combined with Ara-c and Doxo significantly increased cell cycling and apoptosis compared with SCR+Ara-c+Doxo, resulting in reduction of cell growth.
Figure 12B:
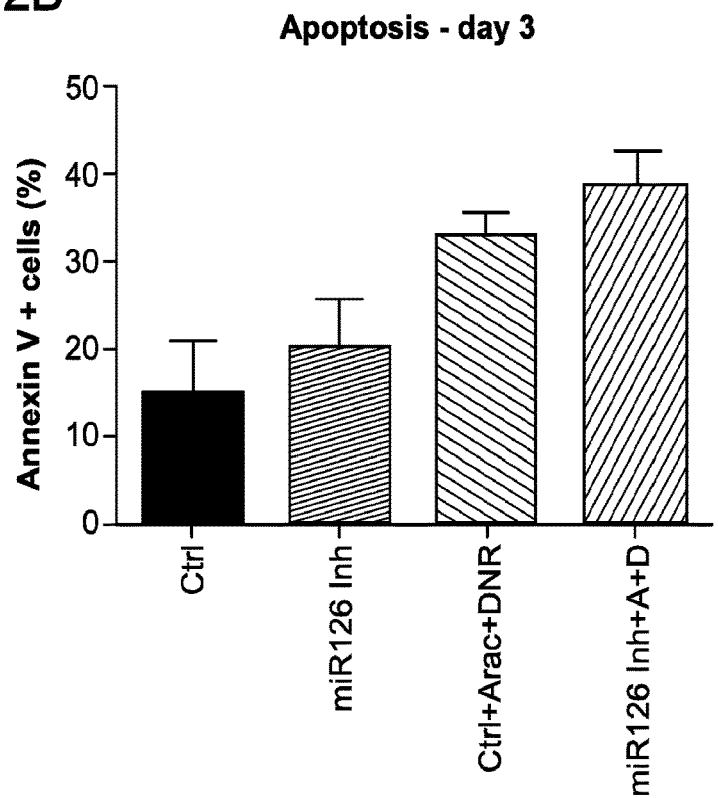
Figure 12C:
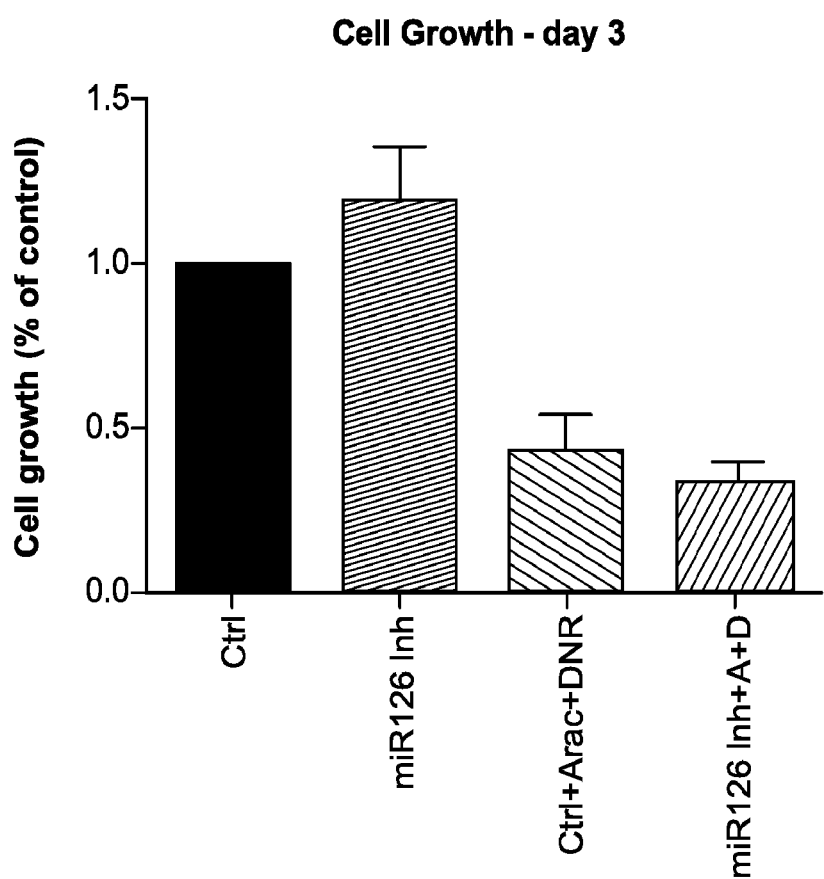

Example 6: Silencing of miR126 by CpG-Anti-miR-126 Inhibitor Combined with Arabinose-c and Doxo Significantly Increased Apoptosis of LSC Compared to Each Treatment Alone Silencing of miR-126 in human AML CD34+ cells by CpG-anti-miR-126 inhibitor (500 nM) combined with Ara-c and Doxo significantly increased cell cycling (FIG. 12A) and apoptosis (FIG. 12B) compared with Ara-c and Doxo alone, resulting in reduction of cell growth (FIG. 12C).

Figure 13A:
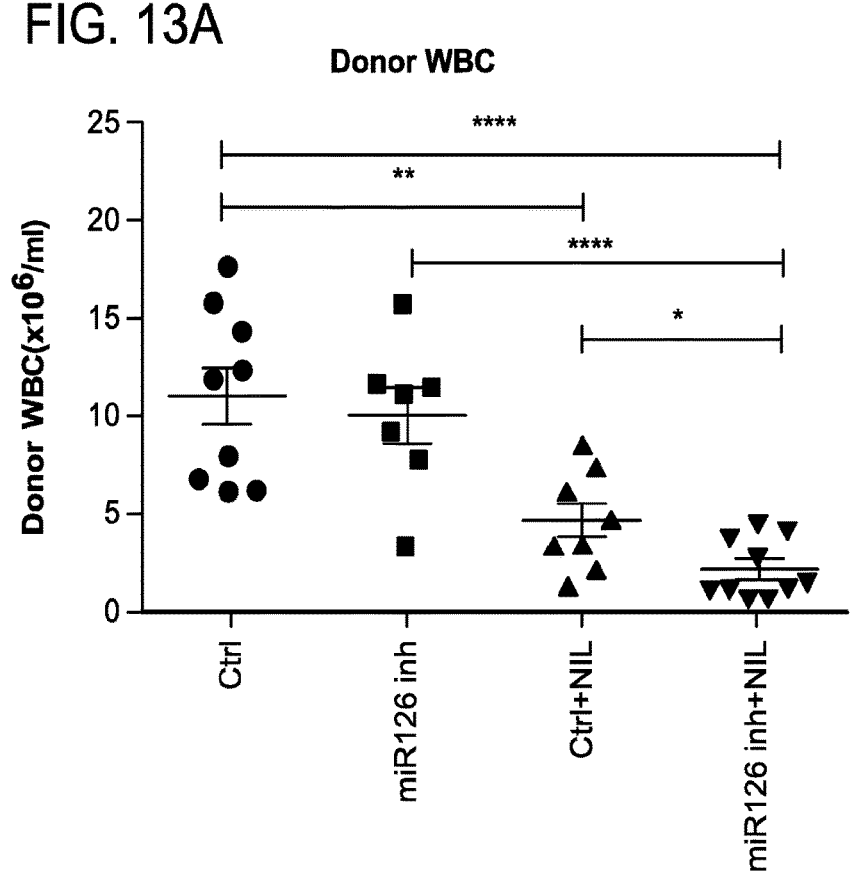
FIGS. 13A-D are scatter plots showing reduced spleen weight (FIG. 13B) and reduced CML cells observed in the bone marrow (BM) (FIG. 13C) and spleen (FIG. 13D) of the mice treated with NIL+miR126 inhibitor compared with the mice treated with NIL+SCR. SCLtTA/BCR-ABL mice were treated with CpG-miR-126 inhibitor (5 mg/kg, every other day, iv injection), SCR (5 mg/kg, every other day, iv injection), NIL (50 mg/kg, daily by garage)+SCR, NIL+miR-126 inhibitor for 3 weeks and then the remaining CML cells in the PB (FIG. 13A), BM (FIG. 13C) and spleen (FIG. 13D) were analyzed. Reduced CML white blood cells in the PB of the mice treated with the NIL+miR126 inhibitor were seen (FIG. 13A), compared with the mice treated with NIL+SCR. Reduced spleen weight (FIG. 13B) and reduced CML cells were observed in the BM (FIG. 13C) and spleen (FIG. 13D) of the mice treated with NIL+miR126 inhibitor compared with the mice treated with NIL+SCR.
Figure 13B:
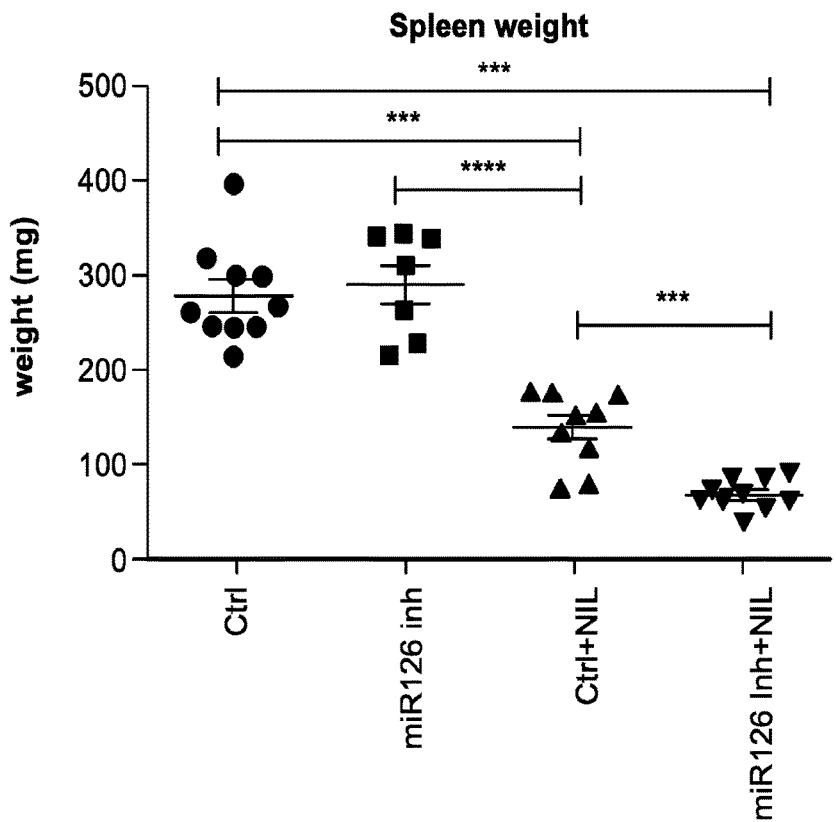
Figure 13C:
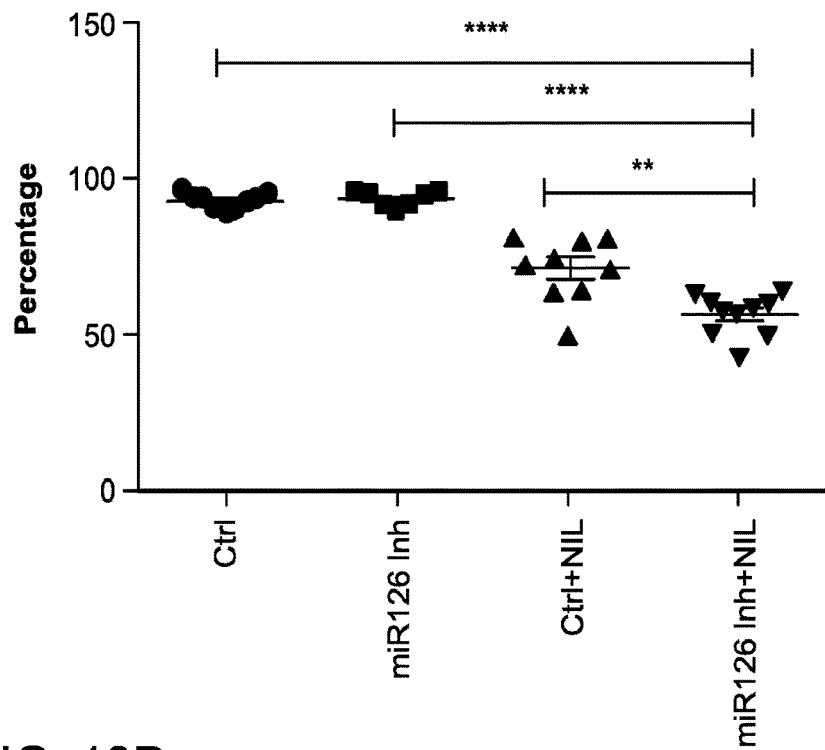
Figure 13D:
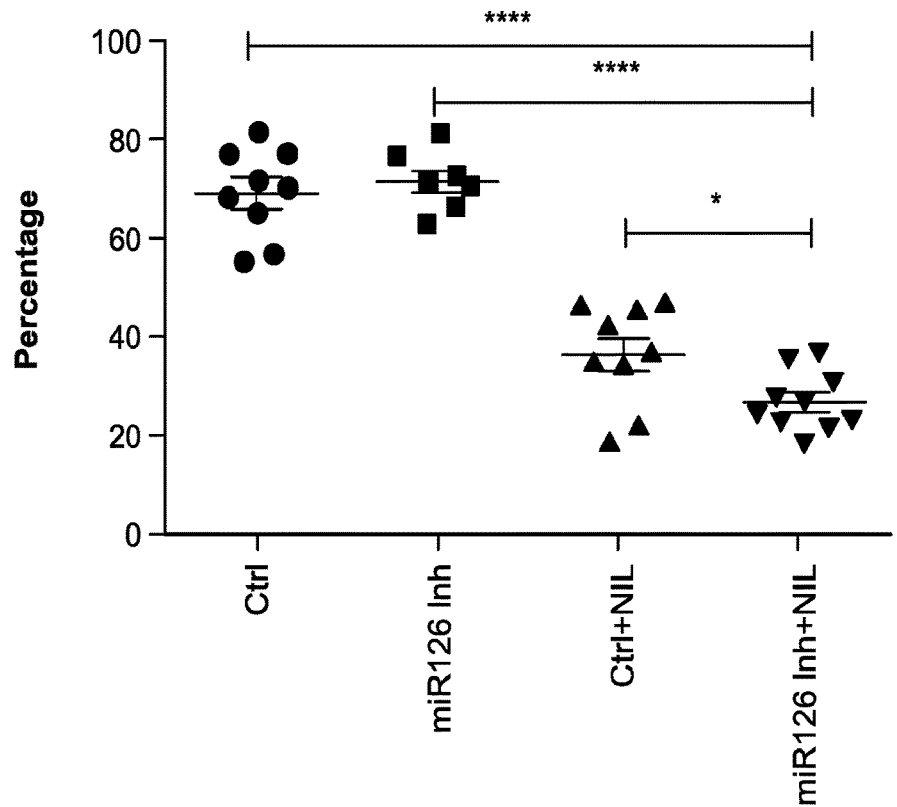
Figure 14A:
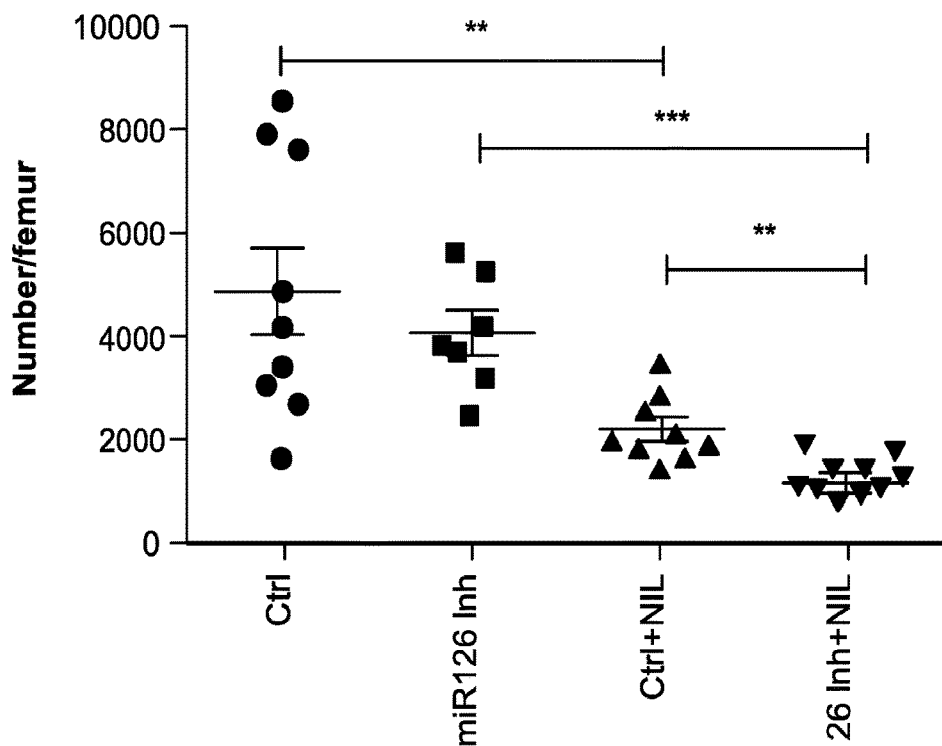
FIGS. 14A-D are scatter plots showing reduced CML LSK and LSC observed in the bone marrow (BM) (FIGS. 14A, 14C) and spleen (FIGS. 14B, 14D) of the mice treated with NIL+miR126 inhibitor compared with the mice treated with NIL+SCR. SCLtTA/BCR-ABL mice were treated with CpG-miR-126 inhibitor, SCR, NIL+SCR, NIL+miR-126 inhibitor for 3 weeks and then the remaining CML LSK primitive cells and LSC in the BM and spleen were analyzed. Reduced CML LSK and LSC were observed in the BM (FIGS. 14A, 14C) and spleen (FIGS. 14B, 14D) of the mice treated with NIL+miR126 inhibitor compared with the mice treated with NIL+SCR.
Figure 14B:
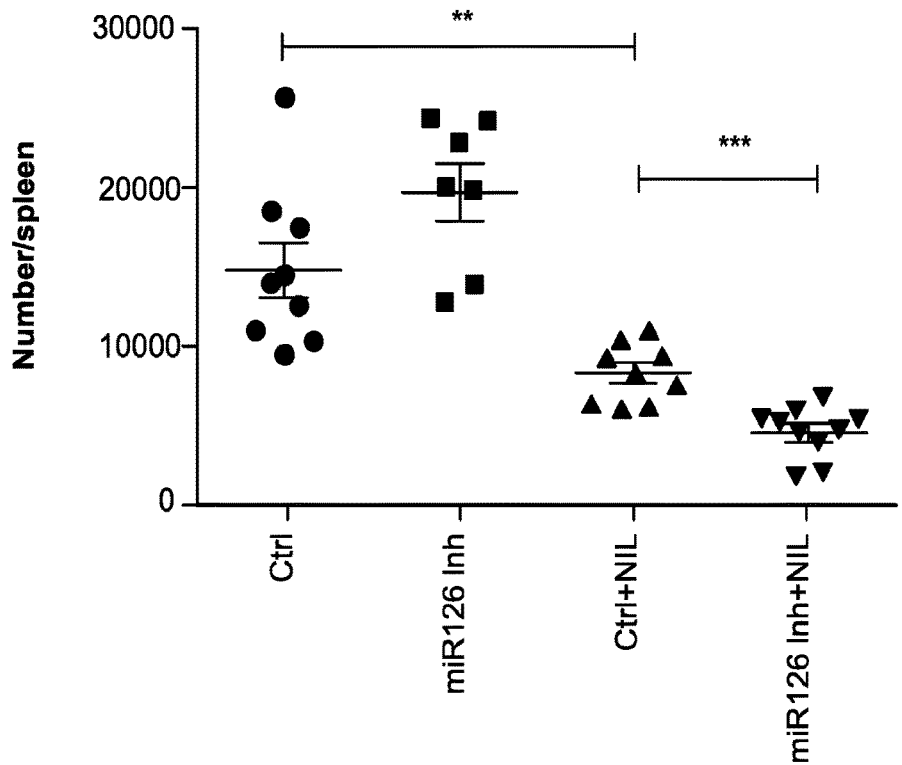
Figure 14C:
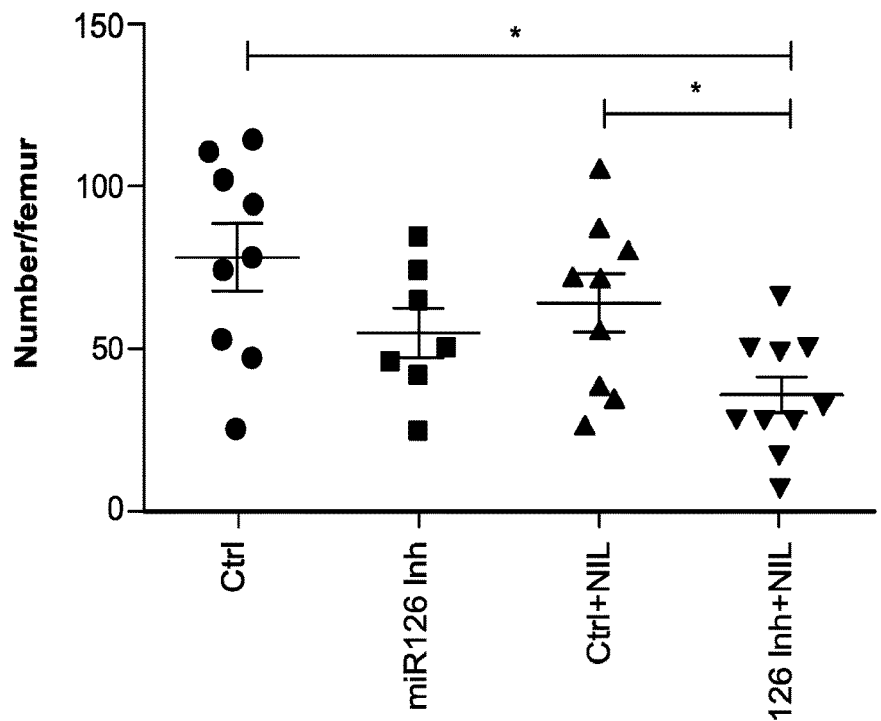
Figure 14D:
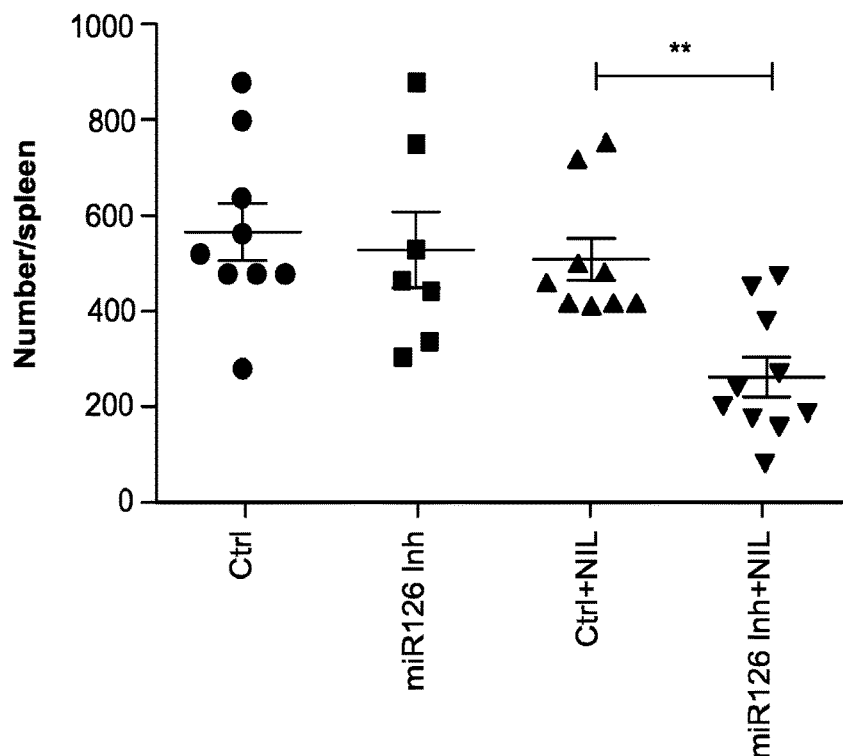
Figure 15:
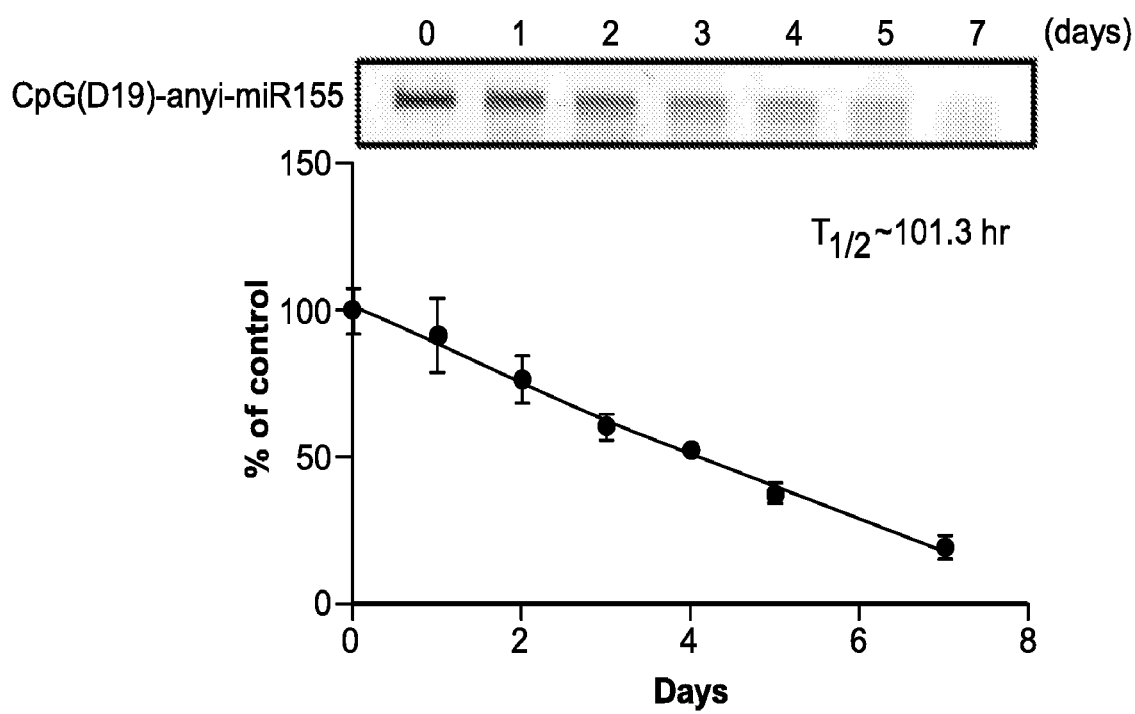
FIG. 15. Stability of CpG-anti-miRs. Half-life of chemically modified CpG-anti-miRs in 50% human serum. CpG-anti-miRs were incubated in human serum at the concentration of 50% at 37° C. for up to 7 days. The samples were then resolved on 7.5 M Urea/20% PAGE gel and stained using ethidium bromide. The representative gel for CpG-anti-miR155 is shown. Graph showing quantification of band intensities combined from 3 independent experiments. The estimated half-life is as indicated.
Figure 16A:
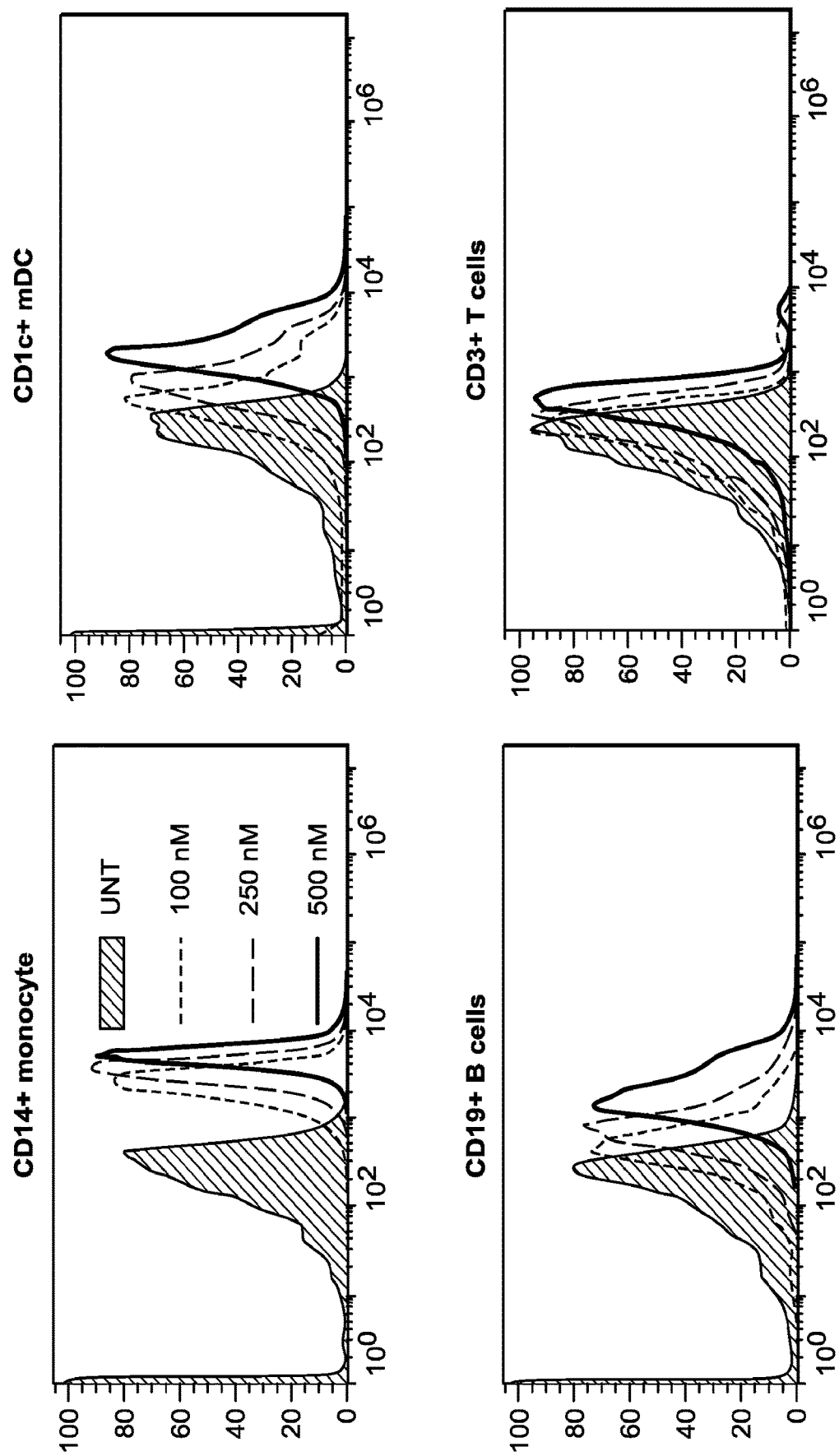
Figure 16B:
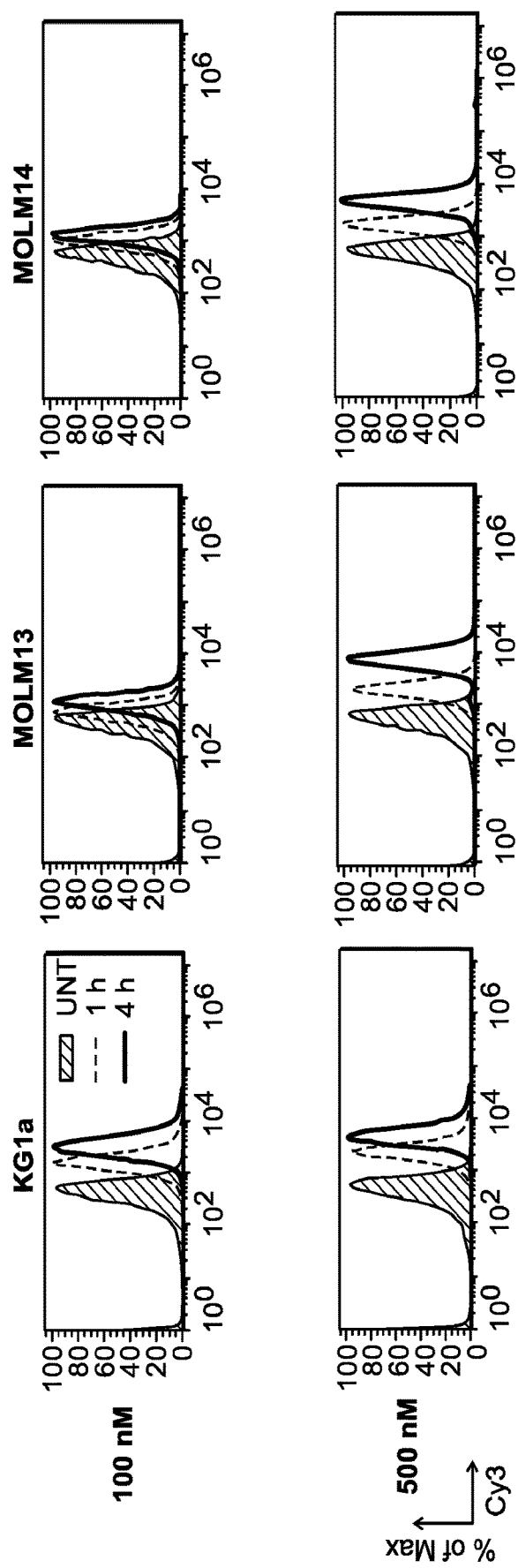
Figure 17A:
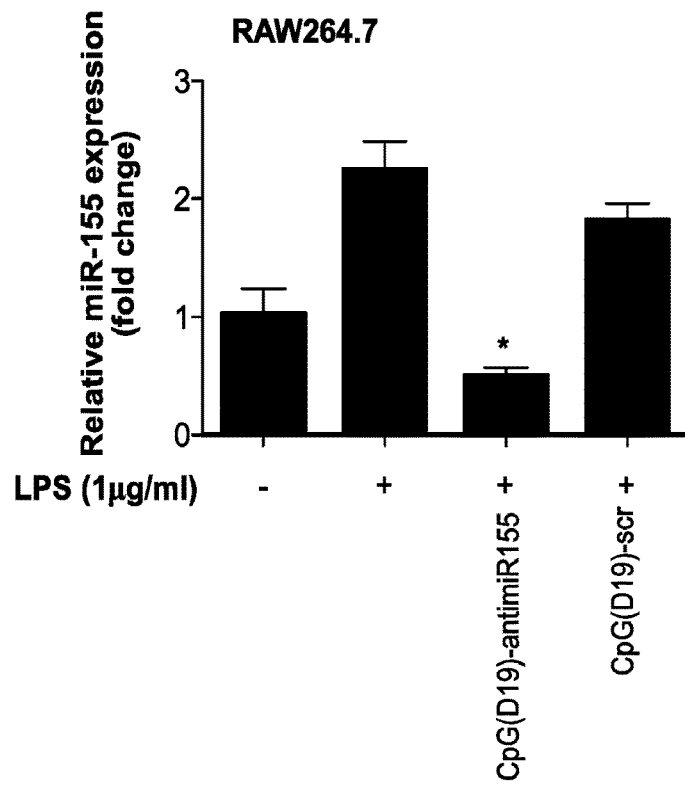
FIGS. 17A-17F. Inhibitory effects of CpG-anti-miR155.
Figure 17B:
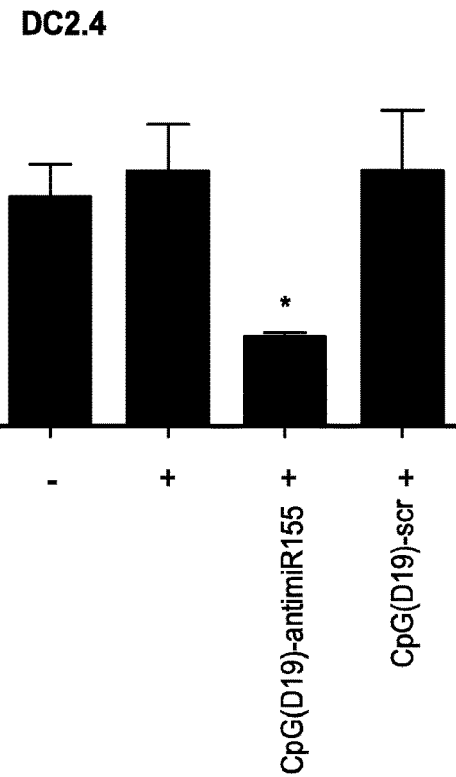
Figure 17C:
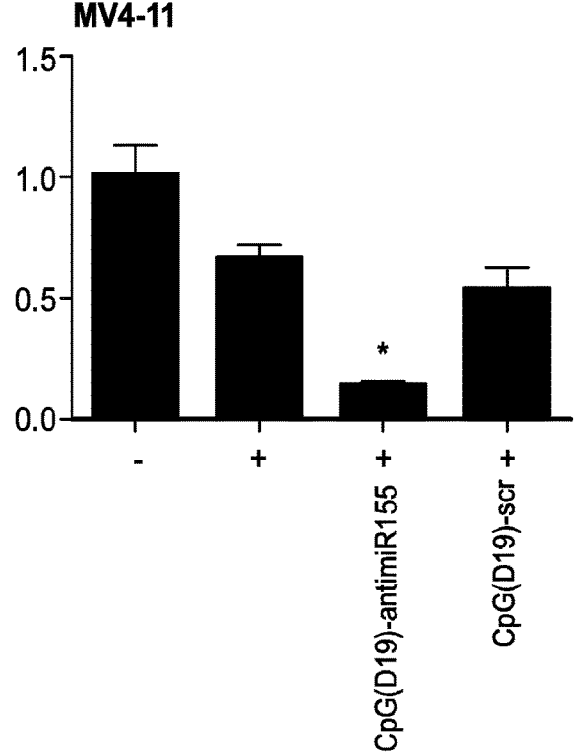
Figure 17D:
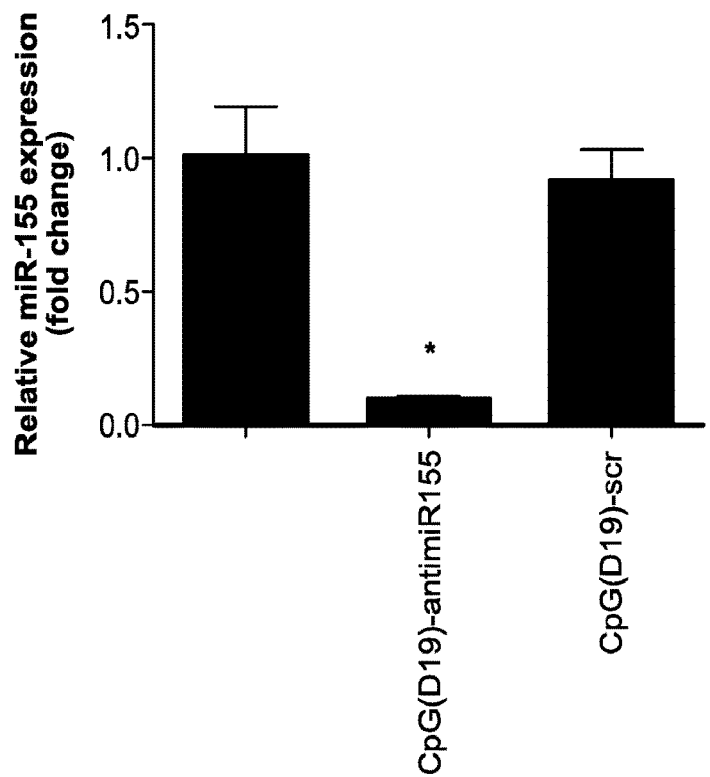
Figure 17E:
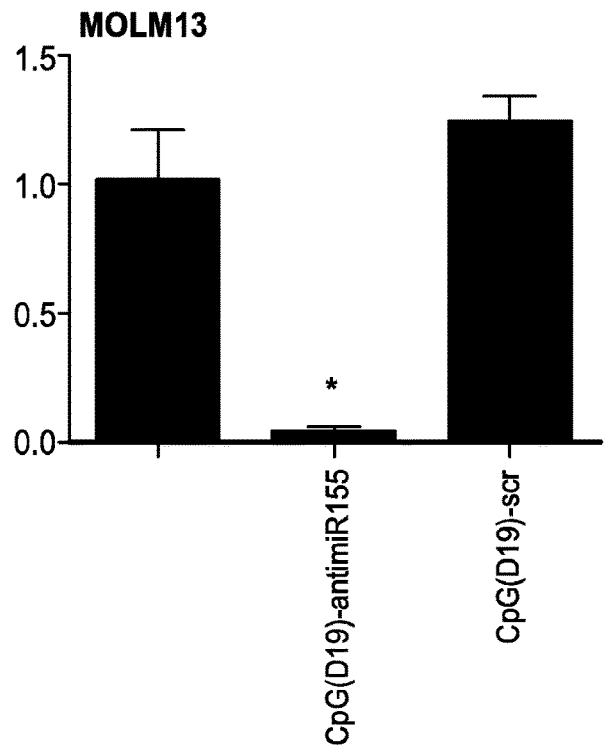
Figure 17F:
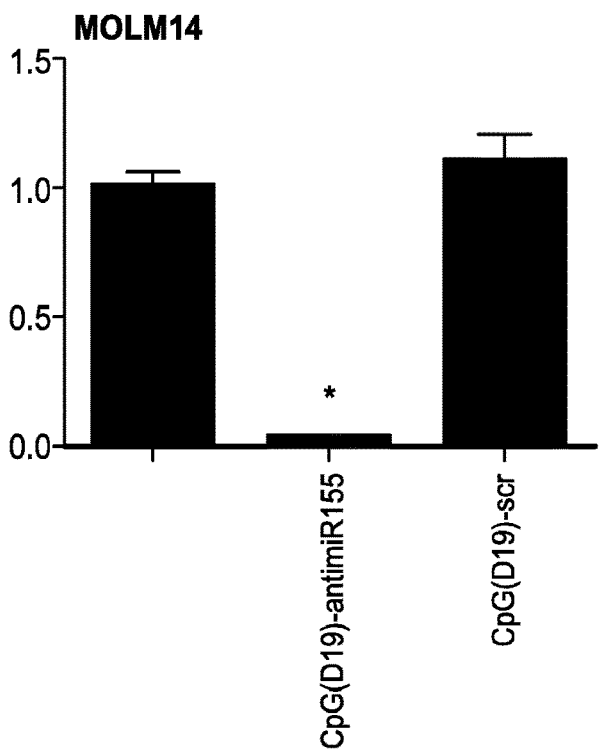
Figure 18A:
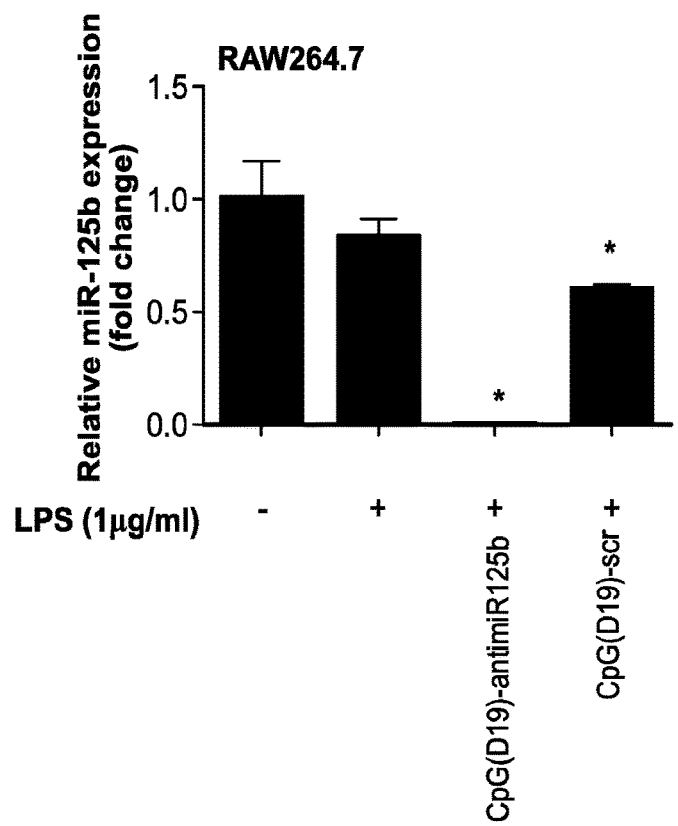
FIGS. 18A-18F. Inhibitory effects of CpG-anti-miR125b.
Figure 18B:
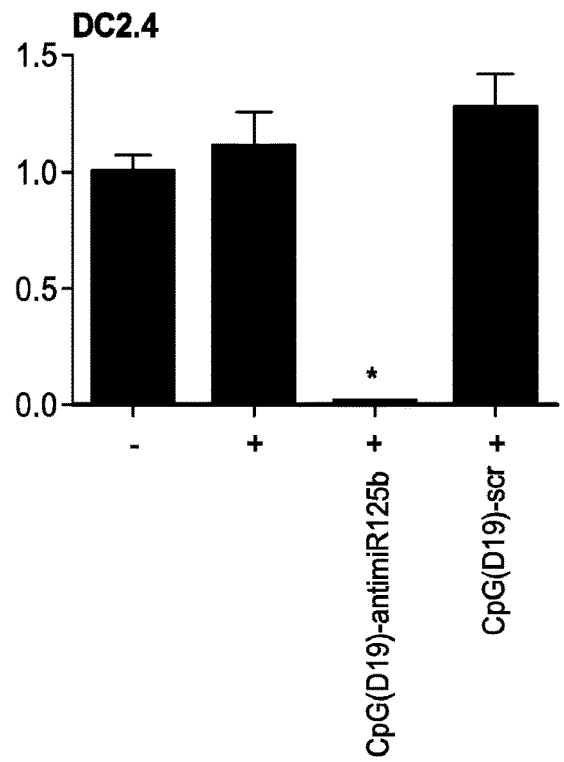
Figure 18C:
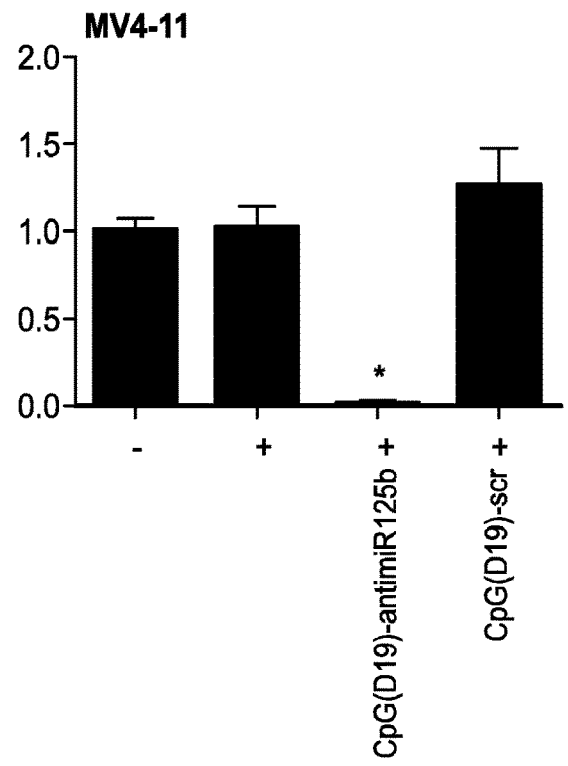
Figure 18D:
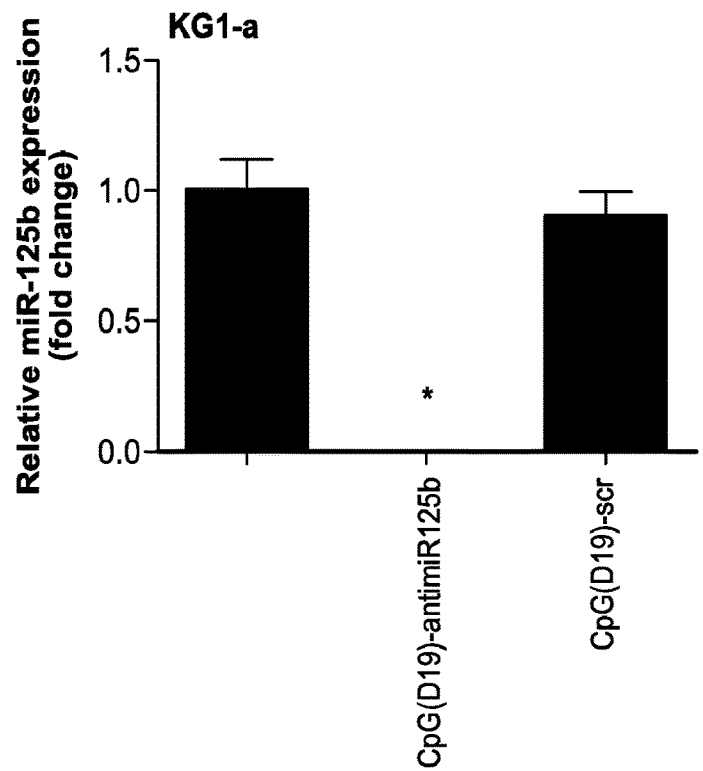
Figure 18E:
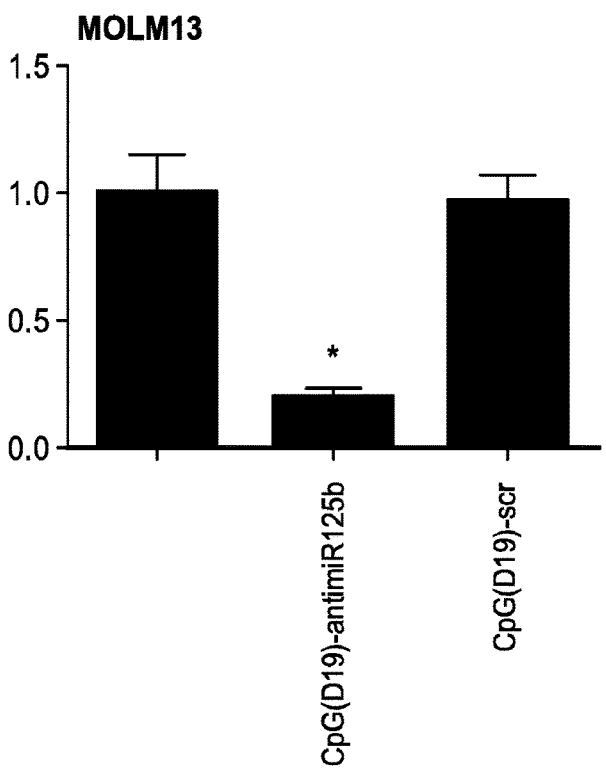
Figure 18F:
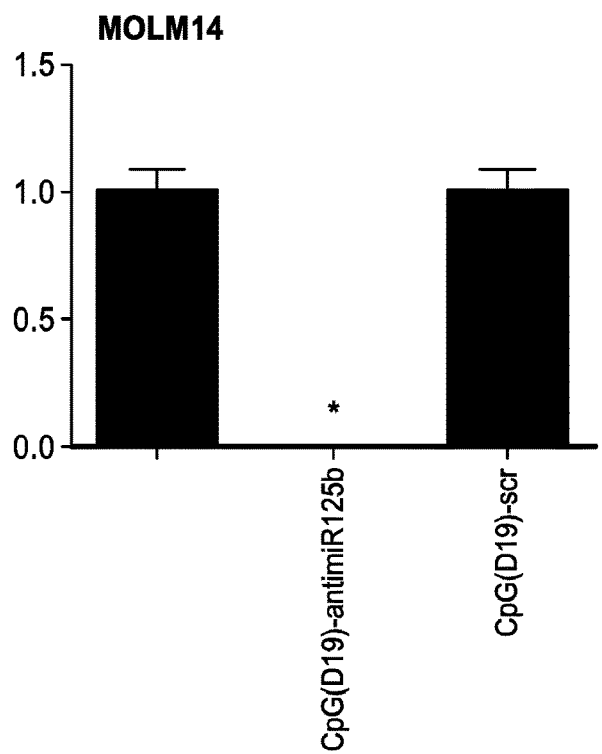
Figure 19A:
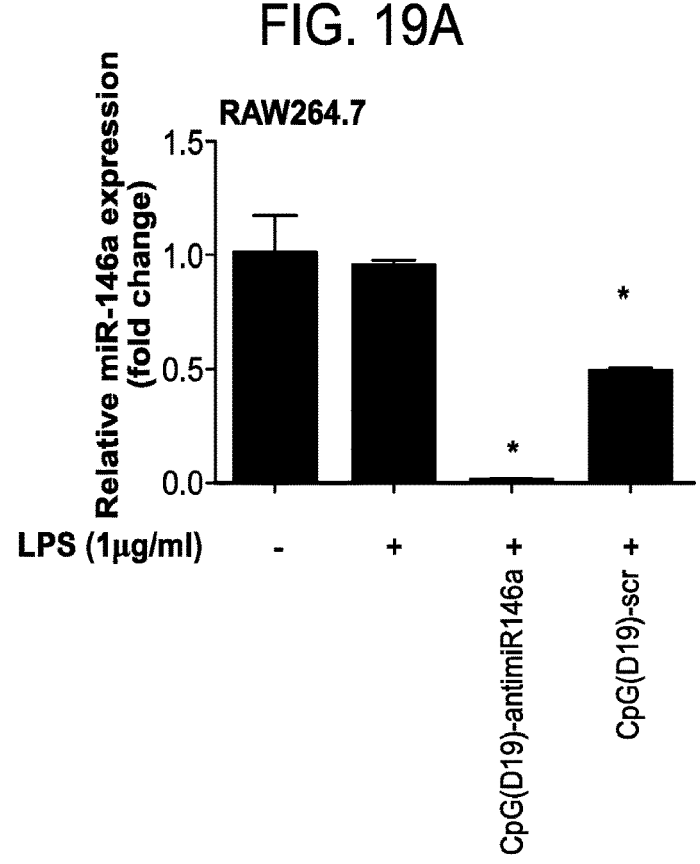
Figure 19B:
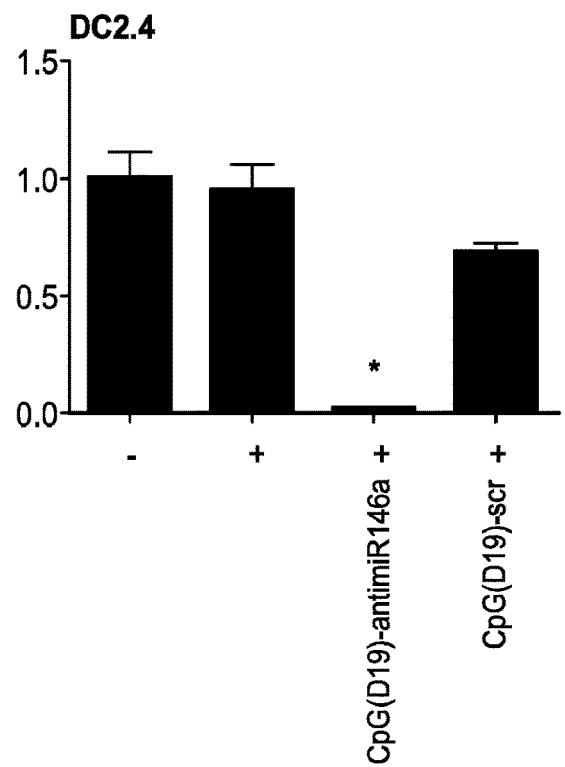
Figure 19C:
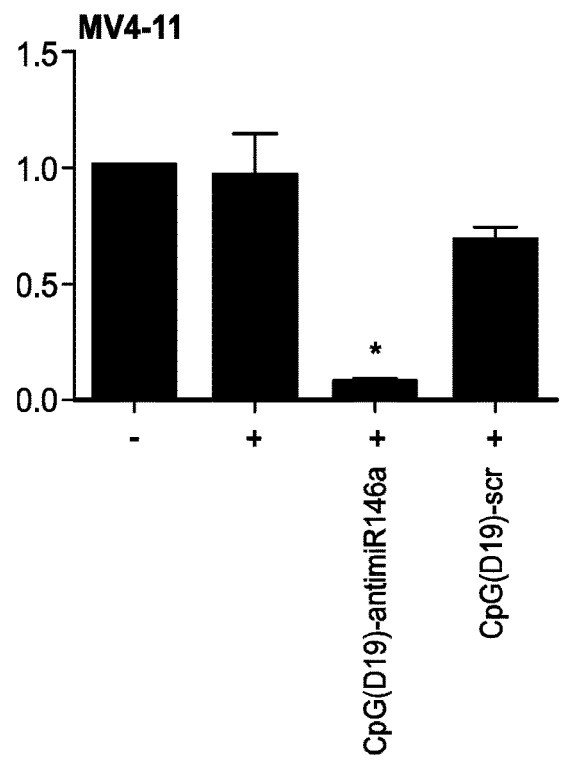
Figure 19D:
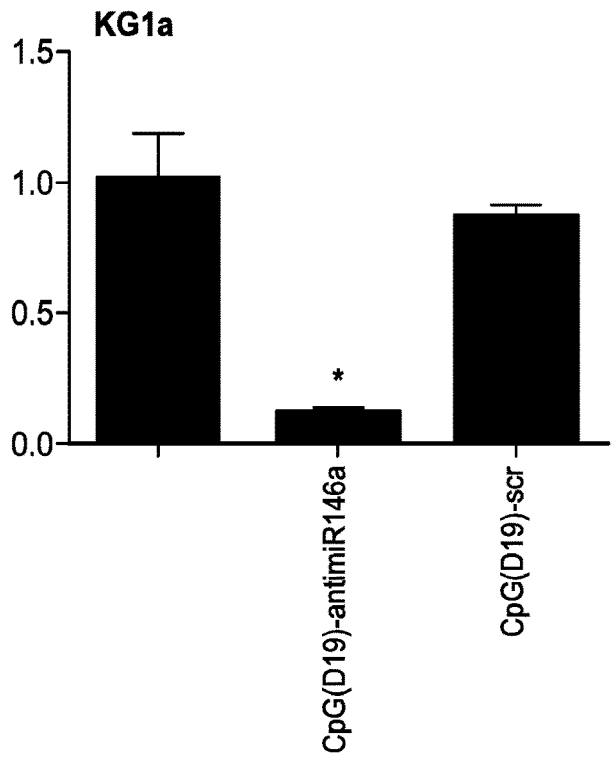
Figure 19E:
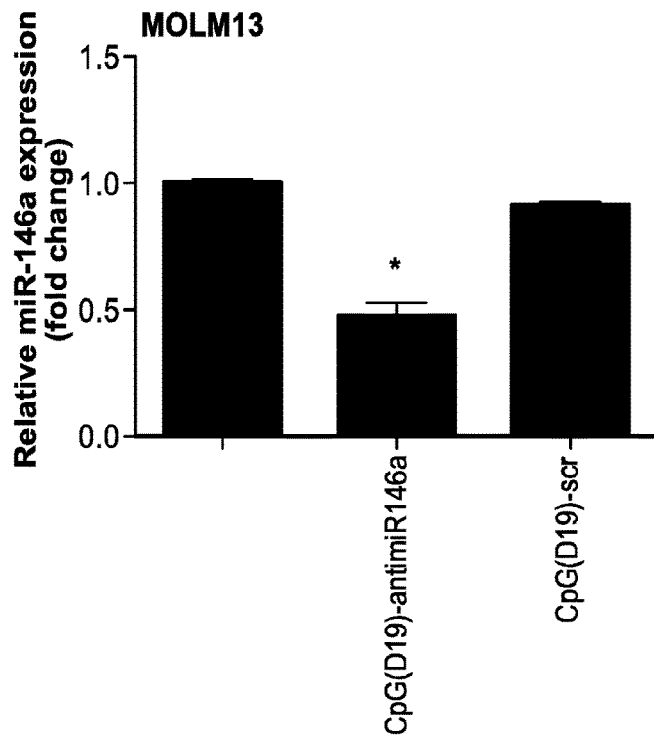
Figure 19F:
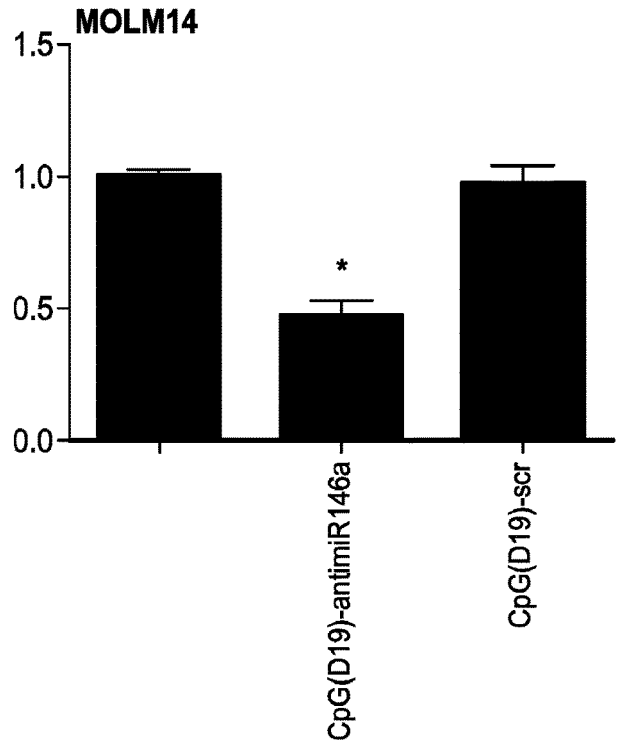
Figure 19G:
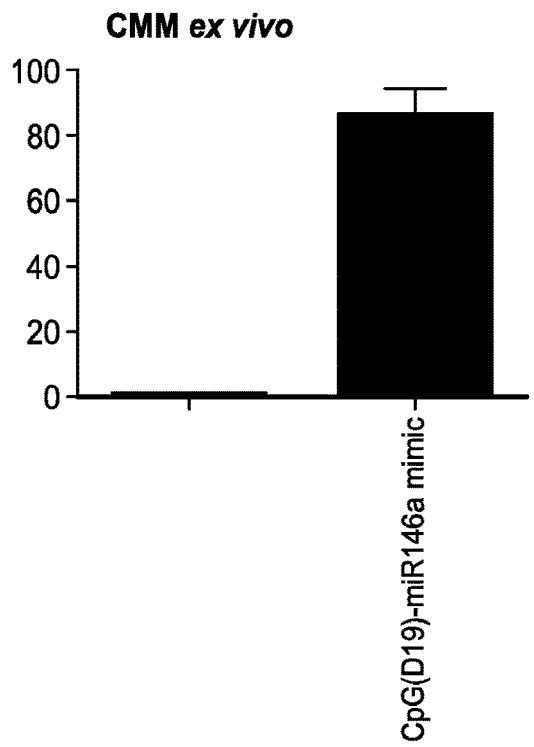
Figure 19H:
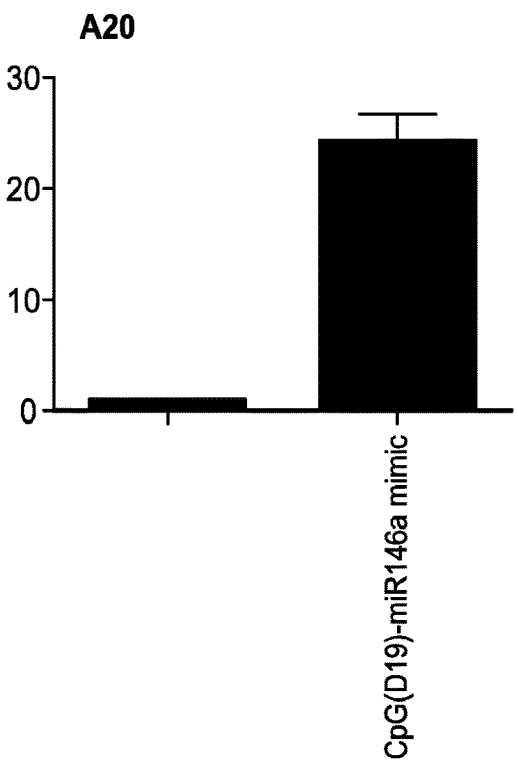

Example 7: In Vivo Effect of CpG-Anti-miR126 on Growth of Primary AML and CML LSC and Therapeutic Response SCLtTA/BCR-ABL mice were treated with CpG-miR-126 inhibitor (5 mg/kg, every other day, iv injection), SCR (5 mg/kg, every other day, iv injection), NIL (50 mg/kg, daily by garage)+SCR, NIL+miR-126 inhibitor for 3 weeks and then the remaining CML cells in the PB, BM and spleen were analyzed. Reduced CML white blood cells in the PB of the mice treated with the NIL+miR126 inhibitor were seen (FIG. 13A), compared with the mice treated with NIL+SCR. Reduced spleen weight of the mice treated with the NIL+miR126 inhibitor were seen (FIG. 13B), compared with the mice treated with NIL+SCR. Reduced CML cells, CML LSK and CML LTHSC were observed in the BM and spleen of the mice treated with NIL+miR126 inhibitor compared with the mice treated with NIL+SCR (FIGS. 13C-D, FIGS. 14A-D). The effect of CpG-anti-miR-126 on growth of primary AML LSC and therapeutic response in vivo is still ongoing. These observations indicate that blocking of miR-126 by a myeloid cell-specific CpG-anti-miR-126 ODN inhibitor, among other compounds of the present disclosure, is very effective, and therefore represents a novel therapeutic method targeting miRNA in leukemia and other types of cancer disclosed herein.

Example 8: Uptake and Inhibitory Effect of CpG-Anti-miRNAs

Sequences of exemplary compounds used in the studies are:

```
CpG-anti-miR155:
                                            (SEQ ID NO: 1)
5'G*G*T GCA TCG ATG CAGG*G*G* G*G xxxxx (SEQ ID NO: 28)
mA*mC*mC*mC*mC*mU*mA*mU*mC*mA*mC*mA*mA*mU*mU*mA* mG*mC*mA*mU*mU*mA*mA 3';

CpG-anti-miR125b:
                                            (SEQ ID NO: 1)
5' G*G*T GCA TCG ATG CAGG*G*G* G*G xxxxx (SEQ ID NO: 34)
mU*mC*mA*mC*mA*mA*mG*mU*mU*mA*mG*mG*mG*mU*mC*mU* mC*mA*mG*mG*mG*mA 3';
and

CpG-anti-miR146a:
                                            (SEQ ID NO: 1)
5' G*G*T GCA TCG ATG CAGG*G*G* G*G xxxxx (SEQ ID NO: 36)
mC*mC*mC*mA*mU*mG*mG*mA*mA*mU*mU*mC*mA*mG*mU*mU* mC*mU*mC*mA 3',
``` where * indicates a phosphorothioate linkage, mN indicates a 2'OMe modified nucleotide, and x indicates a linker described herein.

CpG-anti-miRNAs were Cy3-labeled to detect the intracellular uptake by target cells using flow cytometry. Human immune cells were incubated with indicated concentrations of CpG-anti-miR146a, CpG-anti-miR155 or CpG-anti-miR125b and uptake of these compounds was observed in the cells (FIGS. 16A-16B, 17A-17F, 18A-18F, 19A-19H). Treatment of these compounds reduces the corresponding miR expression in human and mouse myeloid cells (FIGS. 17A-17F, 18A-18F, 19A-19H).

Figure 26A:
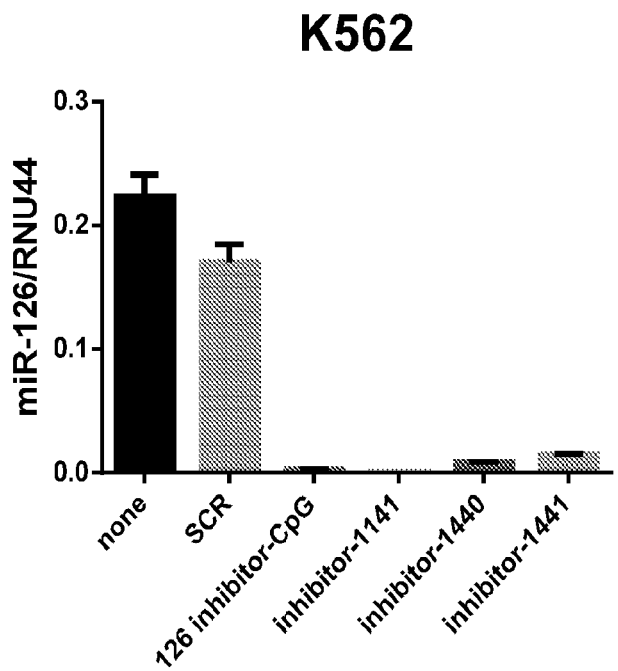
Figure 26B:
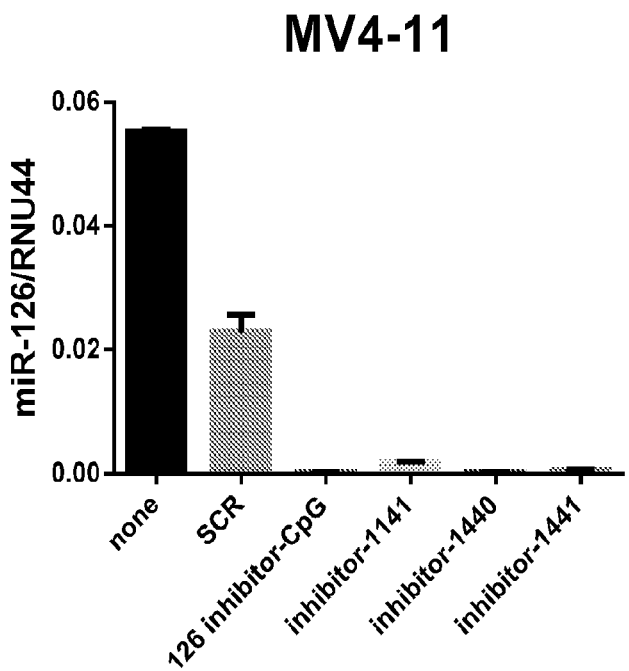
Figure 26C:
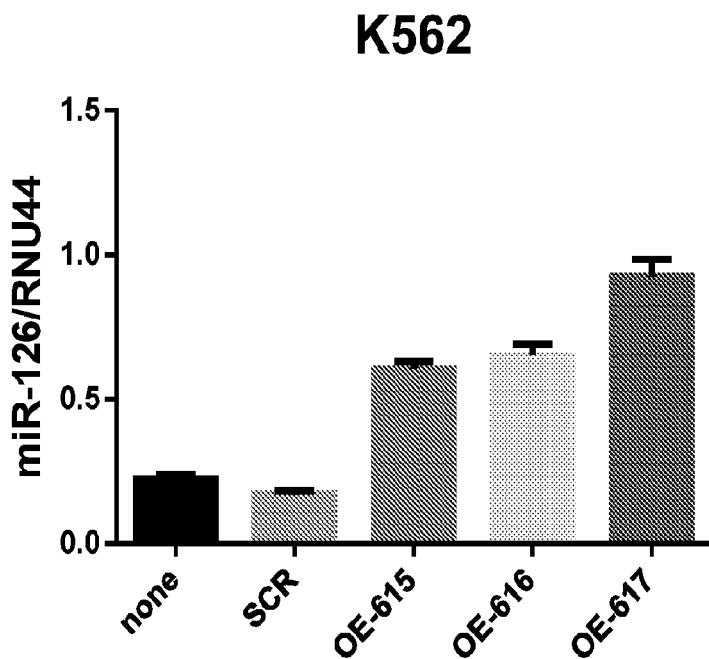
Figure 26D:
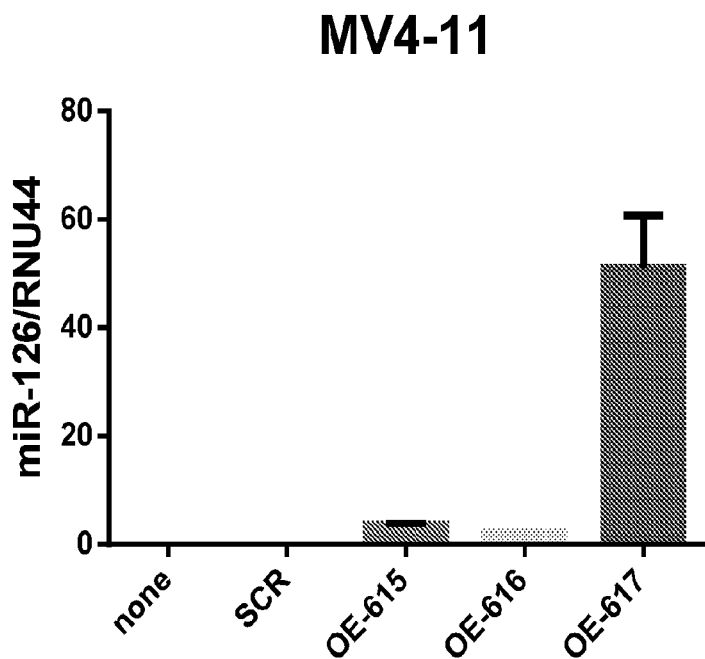

Effective knockdown of miR-126 with miR-126 inhibitors conjugated with CpG, GpC and PS, and effective over-expression with miR-126 mimics in K562 and MV4-11 cells. K562 and MV4-11 cells were treated with miR-126 inhibitors conjugated with CpG, GpC, PS (FIGS. 26A-26B) or miR-126 mimics (615, 616 and 617) (FIGS. 26C-26D) (500 nM) for 24 hours, and miR-126 expression was measured in these cells. We showed here that CpG motif can be omitted in the targeting ODN sequence. GpC and completely PS-modified oligo also succeeds in blocking miR126. Incubation with miR-126 mimics, especially GM617, significantly increased miR-126 expression in K562 and MV4-11 cells. Just like CpG-miR-126 inhibitor which is very effective in reducing miR-126 in cells, we also designed miR-126 mimics, which are very effective in increasing miR-126 levels in cells without using any transduction reagents.

Example 9: Effect of CpG-Anti-miRNAs on Downstream Targets

Figure 20A:
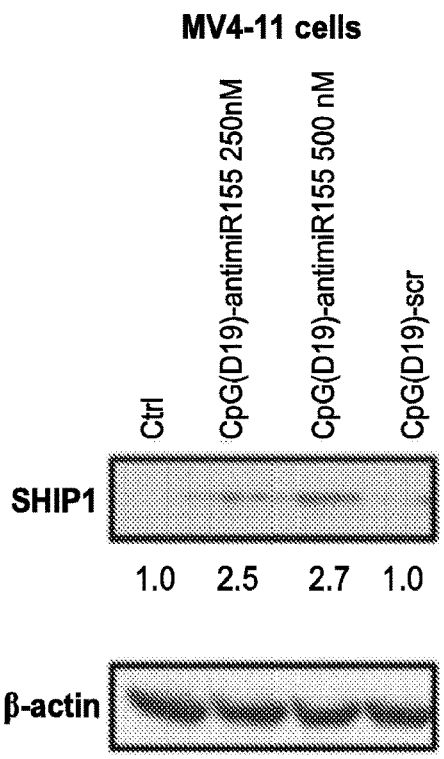
FIGS. 20A-20D. Effects of CpG-anti-miRNAs on downstream targets.
Figure 20B:
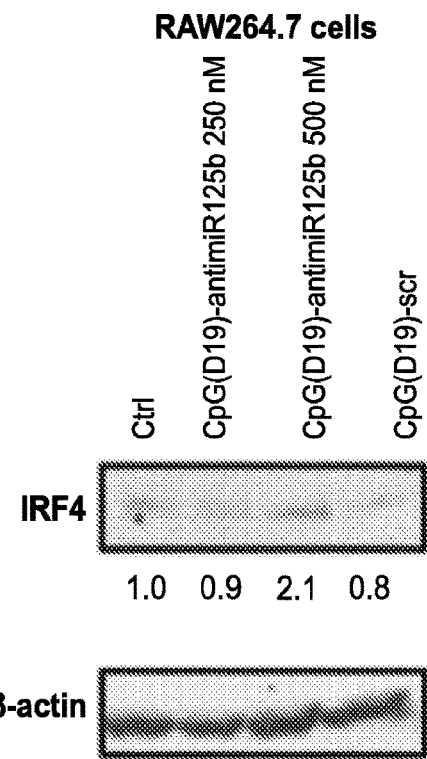
Figure 20C:
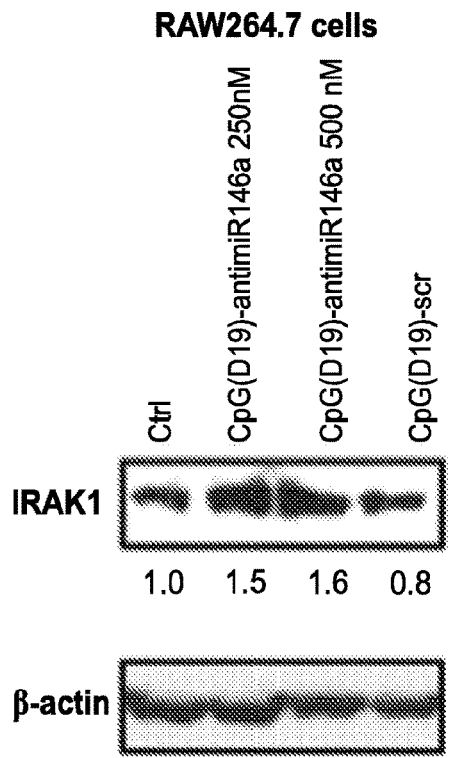
Figure 20D:
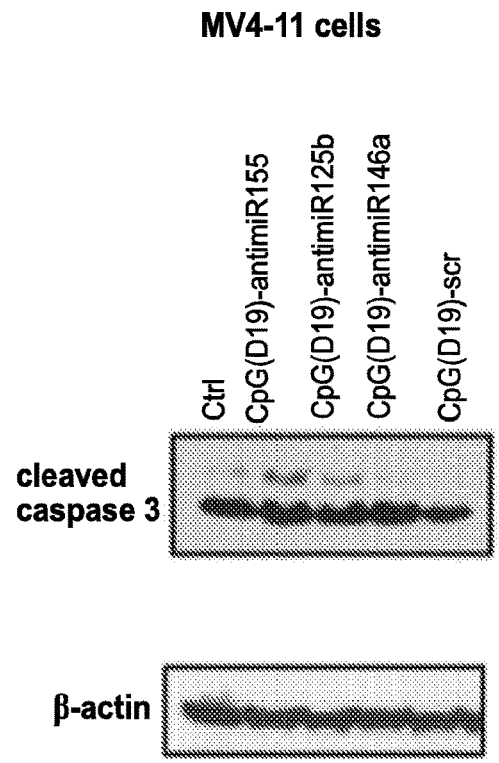

CpG-anti-miRs regulate downstream targets of miR155, miR125b, and miR146a (FIGS. 20A-C). Mouse RAW264.7 or human MV4-11 cells were incubated with 250 nM or 500 nM of CpGanti-miR155, CpG-anti-miR125b, or CpG-anti-miR146a, or 500 nM of CpG-scramble for 48 h, then the cell lysates were collected and electrophoresed and immunoblotted by antibodies against SHIP1 (miR155 target) (FIG. 20A), IRF4 (miR125b target) (FIG. 20B), or IRAK1 (miR146a target) (FIG. 20C). The band intensities were normalized against β-actin and quantified. Fold induction over the control protein levels are indicated below the blot. FIG. 20D) MV4-11 cells were incubated with 500 nM of CpG-anti-miR155, CpG-antimiR125b, CpG-anti-miR146a, or CpG-scramble for 24 h, then cell lysates were collected and electrophoresed and immunoblotted to detect activated caspase 3 indicating induction of apoptosis. SHIP1 and IRAK1 are both upregulated after the treatment of CpG-anti-miRs.

Example 10: Comparing the Inhibition Effects of CpG-Anti-miR and GpC-Anti-miR

Figure 21A:
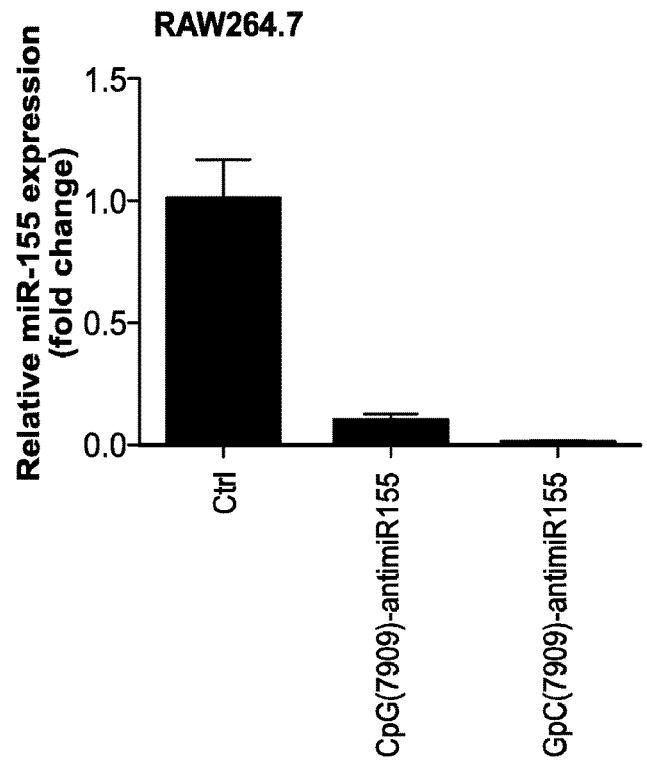
FIGS. 21A-21H. Comparing the inhibition effects of CpG-anti-miR and GpC-anti-miR.
Figure 21B:
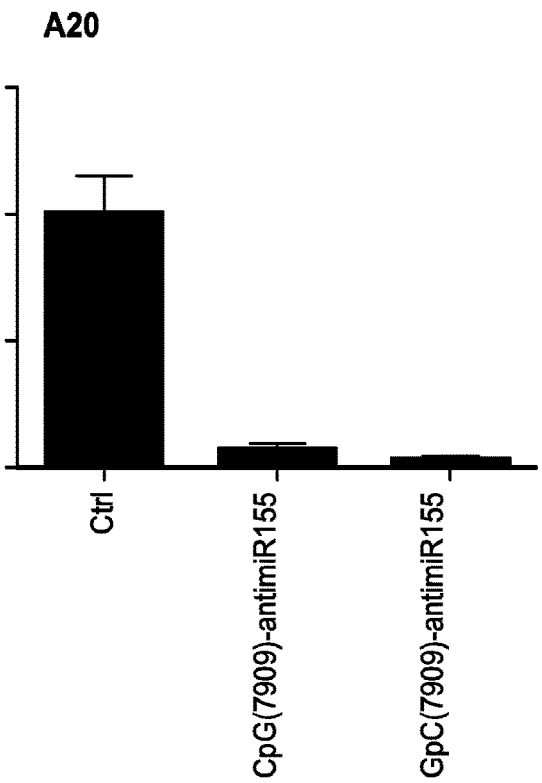
Figure 21C:
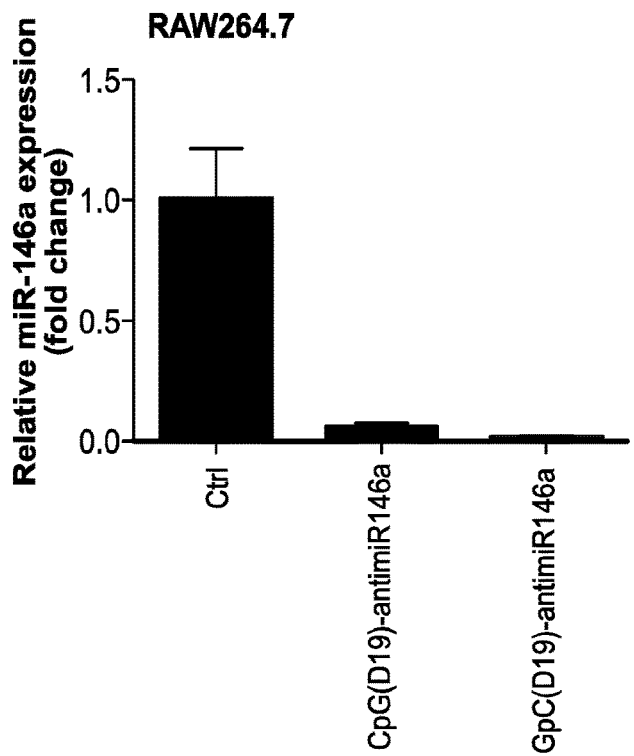
Figure 21D:
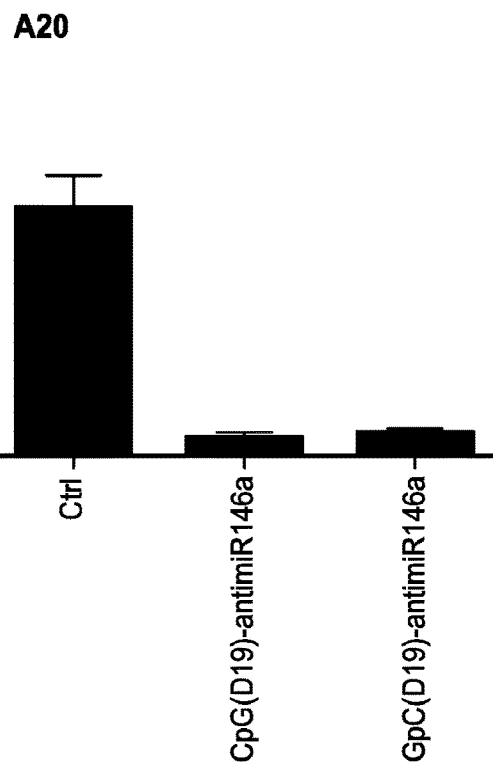
Figure 21E:
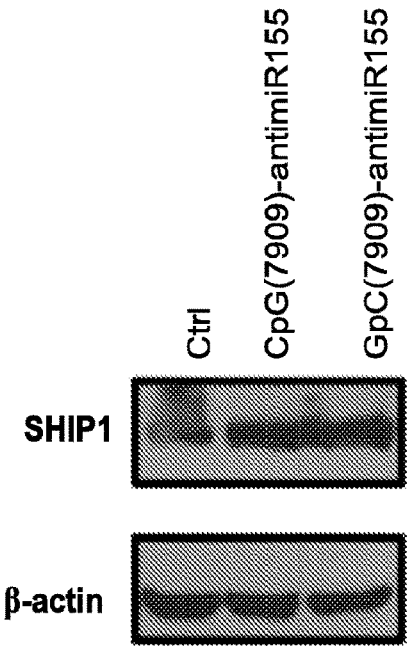
Figure 21F:
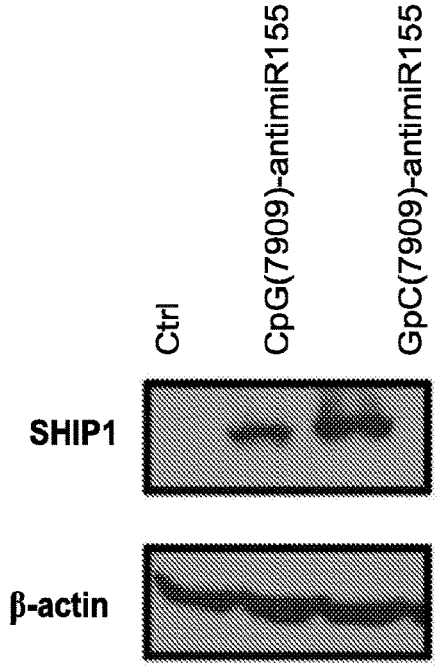
Figure 21G:
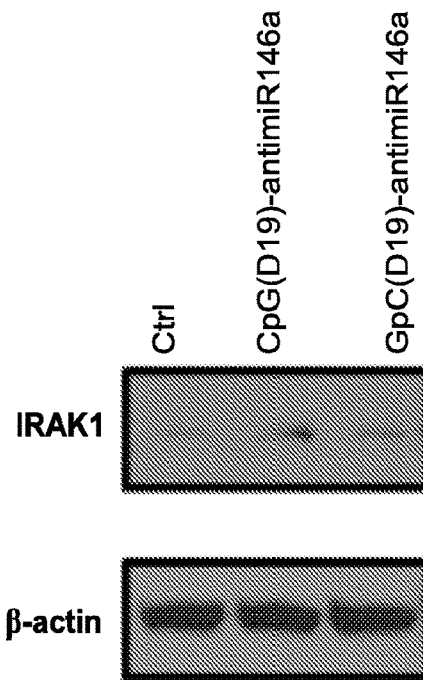
Figure 21H:
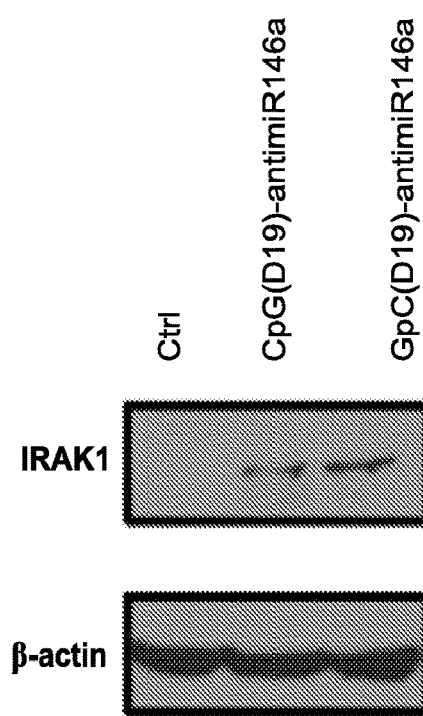

CpG-anti-miR155, GpC-anti-miR155, CpG-anti-miR146a, and GpC-anti-miR146a treatment reduces miR155 or miR-146a expression in RAW264.7 (FIGS. 21A, 21C) and A20 cells (FIGS. 21B,21D). The cells were incubated with 100 nM CpG-anti-miRs or GpC-anti-miRs for 18 hrs. FIGS. 21E-21H) CpG-anti-miRs and GpC-anti-miRs treatment regulates downstream targets of miR155 and miR146a. RAW264.7 (FIGS. 21E,21G) or A20 cells (FIGS. 21F,21H) were incubated with 500 nM of CpG-anti-miR155, GpC-anti-miR155, or CpG-anti-miR146a, GpC-anti-miR146a for 48 hrs, then the cell lysates were collected and immunoblotted using antibodies against SHIP1 (miR155 target) or IRAK1 (miR146a target). These results demonstrate that both CpG and GpC nucleic acid sequences are effective in the compounds described herein.

Example 11: CpG-miR146a Mimic Attenuates LPS Induced Inflammatory Signaling

Figure 22A:
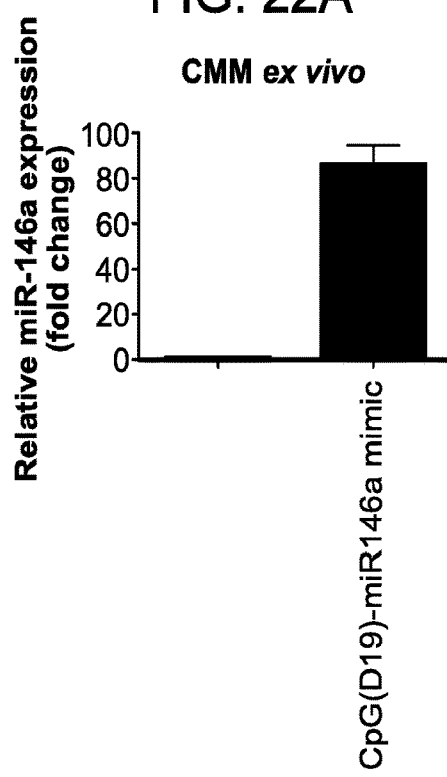
FIGS. 22A-22E. CpG-miR146a mimic attenuates LPS induced inflammatory signaling.
Figure 22B:
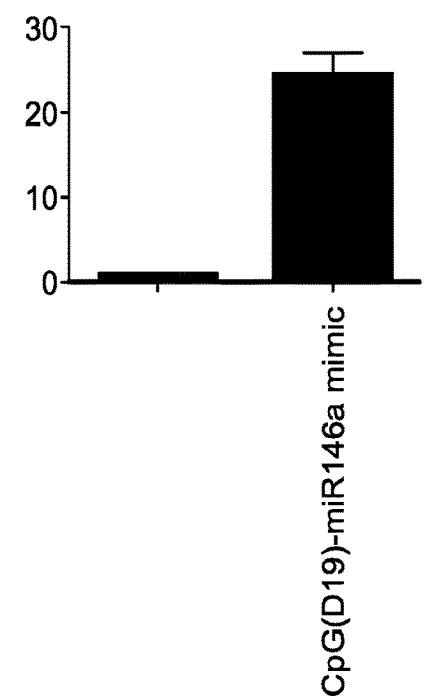
Figure 22C:
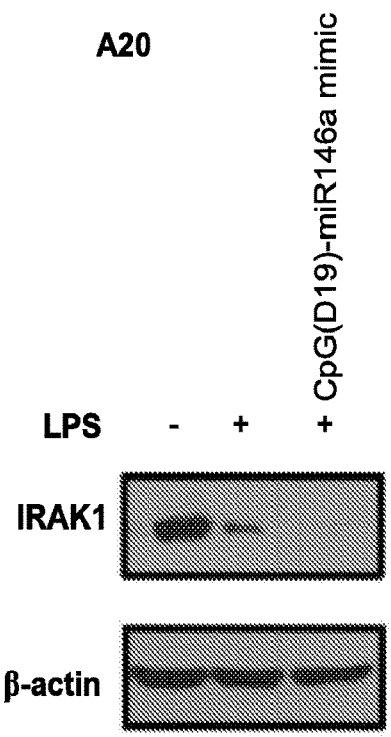
Figure 22D:
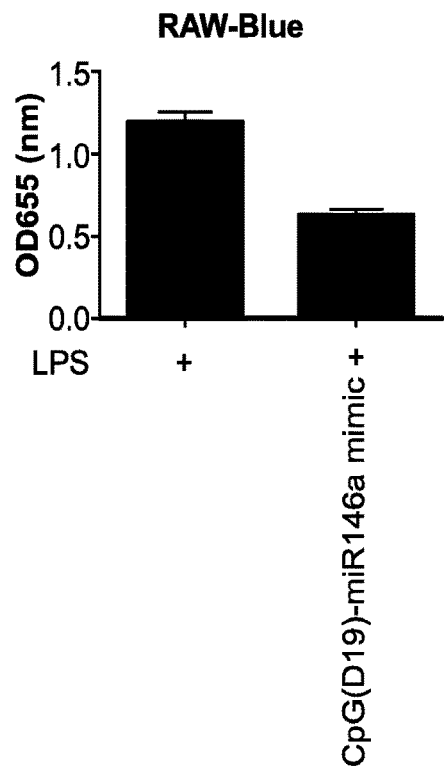
Figure 22E:
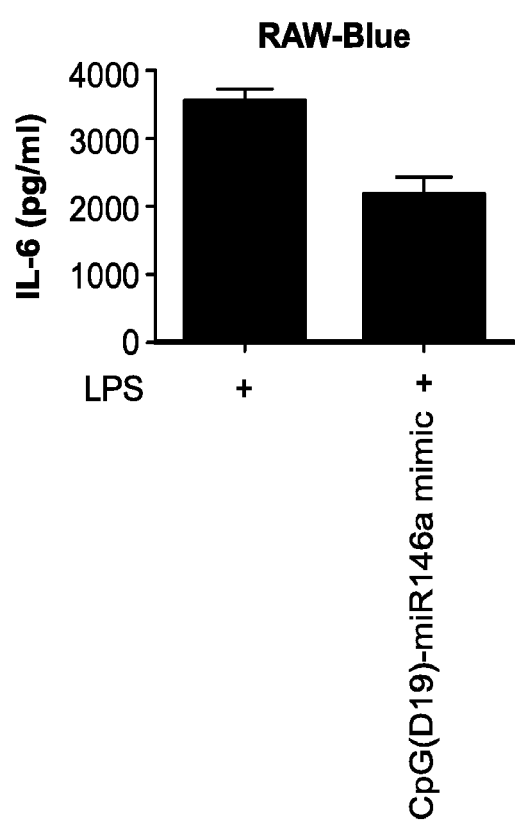

CpG-miR146a mimic increases miR-146a expression in cultured CMM leukemia (FIG. 22A) and A20 lymphoma cells (FIG. 22B). Cells were incubated with 100 nM CpG-miR146a mimic for 18 h. FIG. 22C) CpG-miR146a mimic inhibits IRAK1 expression, a downstream target of miR146a. A20 cells were incubated with 500 nM of CpG-miR146a mimic or LPS (used as a positive control) for 48 h, then the cell lysates were collected and immunoblotted using IRAK1-specific antibodies. FIGS. 22D-22E) RAW-Blue cells, expressing NF-KB-responsive reporter gene, were treated with 500 nM of CpG-miR146a mimic for 24 h and then with 1 pg/ml LPS for another 24 h. Culture medium was collected and analyzed for NF-KB activity using the Quanti-Blue assay kit (FIG. 22D) for IL-6 levels in media using ELISA (FIG. 22E).

Figure 23A:
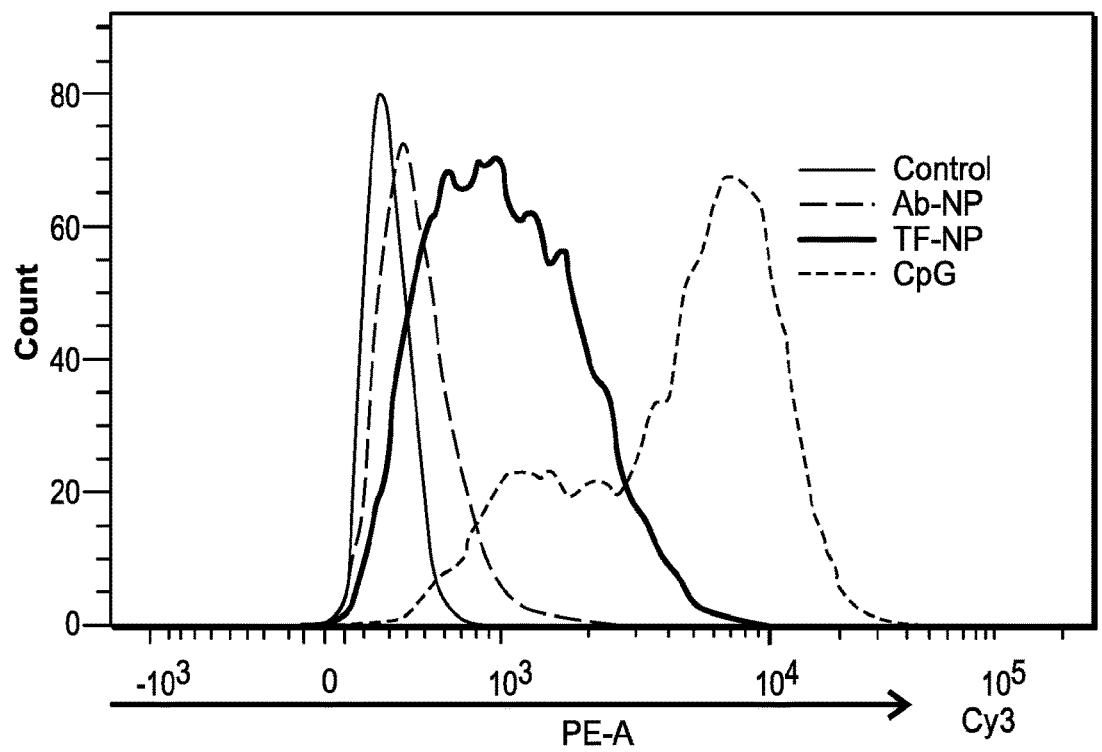
FIGS. 23A-23K. Effective in vitro and in vivo uptake and gene silencing effects of the CpG-miR-126 inhibitor. Uptake test measured by flow cytometric analysis at 4 hours (FIG. 23A) and 24 hours (FIG. 23B) after addition of CpG-miR-126 inhibitor-Cy3 (CpG), Ab-NPs (Ab-NP) or TF-NPs (TF-NP) containing miR-126 inhibitor-Cy3, or naked miR-126 inhibitor-Cy3 (labeled as Control in FIGS. 23A and B) in K562 cells. The experiment was replicated twice. miR-126 expression in K562 was measured by Q-RT-PCR at 24 hours (n=3) (FIG. 23C). Uptake in HUVEC (FIG. 23D), human normal (FIG. 23E) and CML (FIG. 23F) CD34$^+$CD38$^-$ cells at 4 hours after addition of CpG-miR-126 inhibitor-Cy3 (500 nM) was measured by flow cytometry. miR-126 expression in HUVEC (FIG. 23G), normal (FIG. 23H) and CML (FIG. 23I) CD34$^+$CD38$^-$ cells treated with CpG-miR-126 inhibitor (500 nM) for 24 hours is shown (n=4). One of the two cell cycling experiments in normal (FIG. 23J) and CML (FIG. 23K) CD34$^+$CD38$^-$ cells treated with CpG-miR-126 inhibitor (500 nM) by EDU staining is shown. Abbreviations: ab-NPs (CD45 antibody conjugated nanoparticles); TF-NPs (transferrin (TF)-conjugated nanoparticles).
Figure 23B:
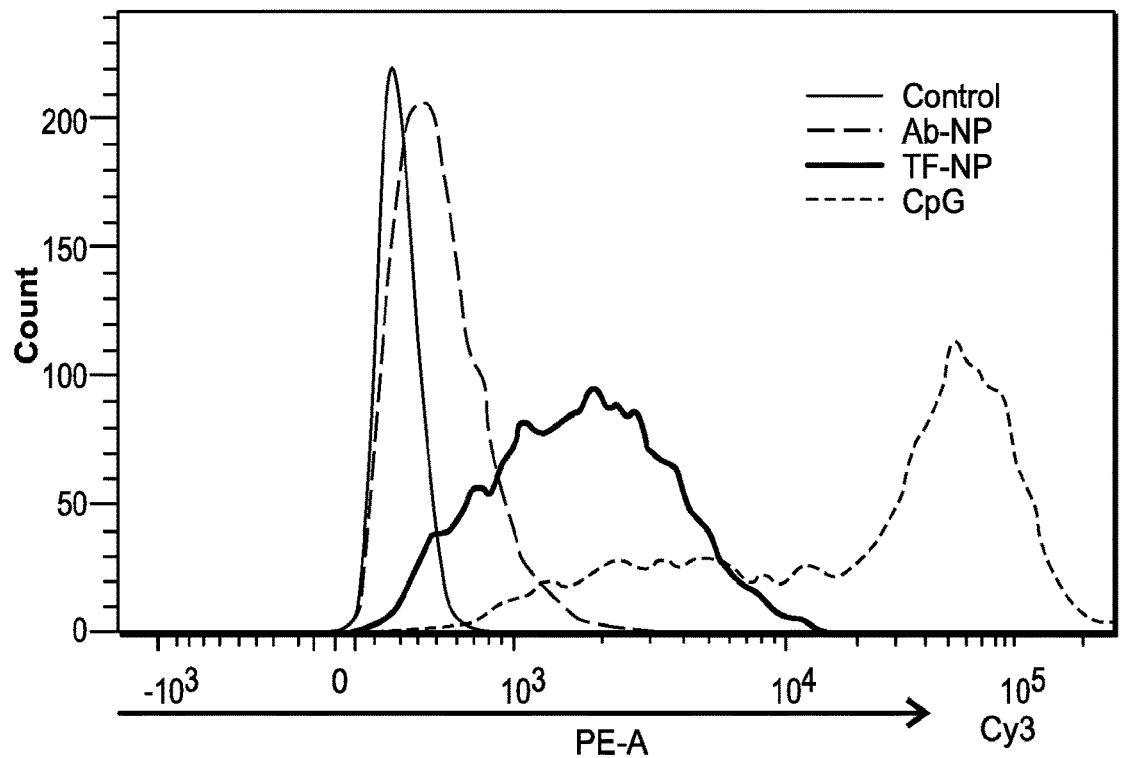
Figure 23C:
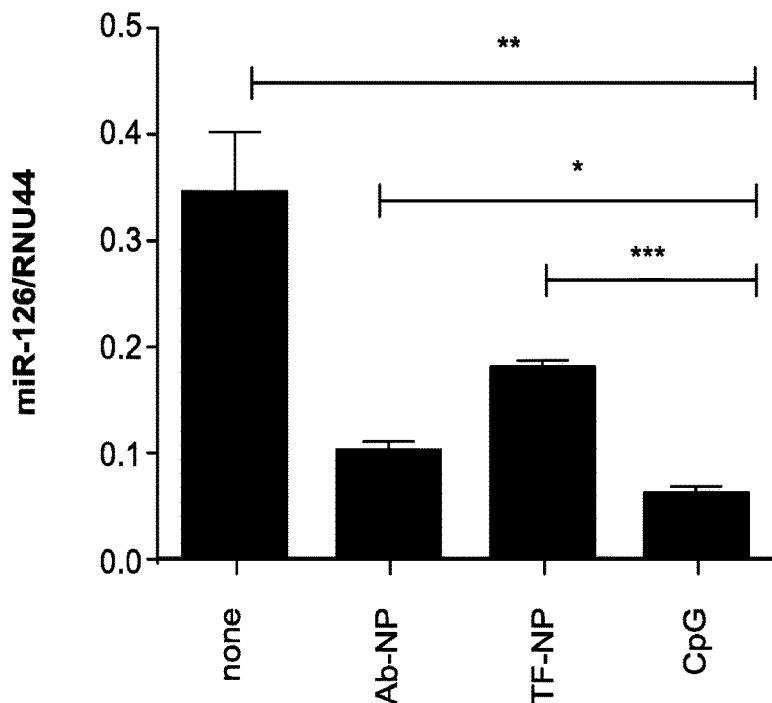
Figure 23D:
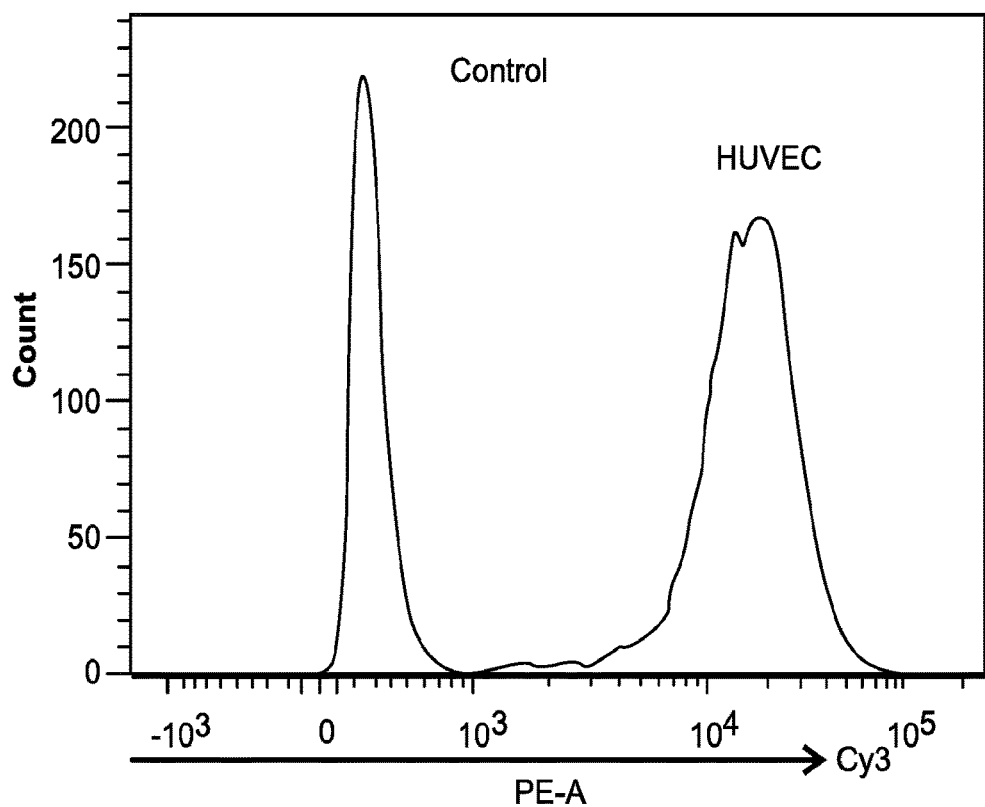
Figure 23E:
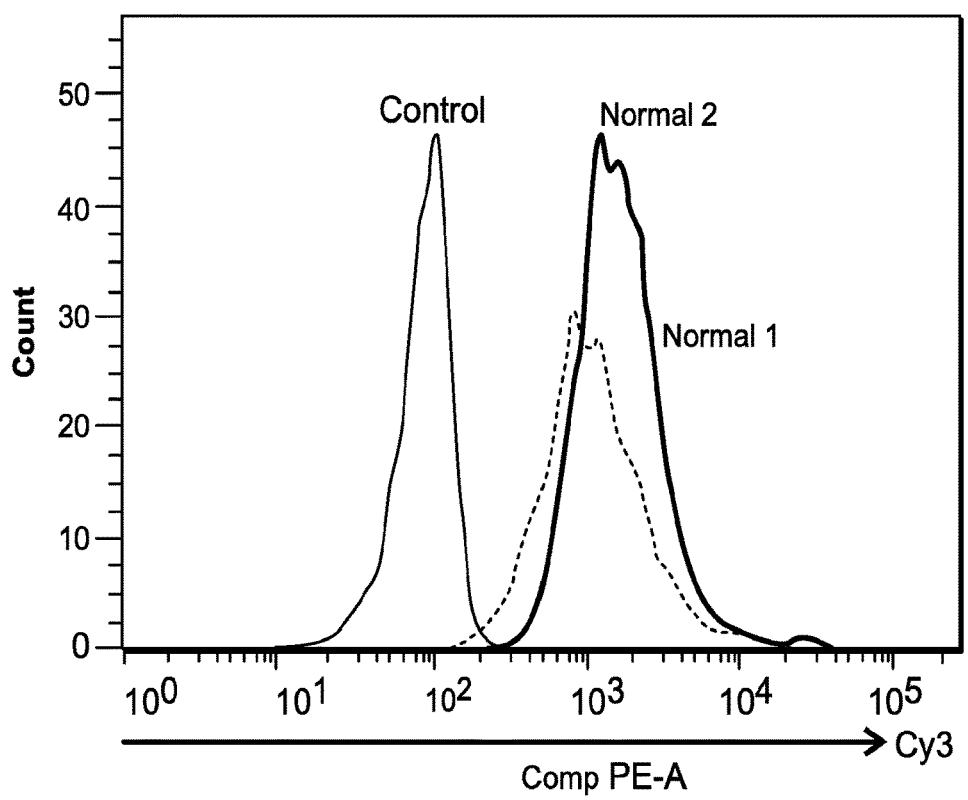
Figure 23F:
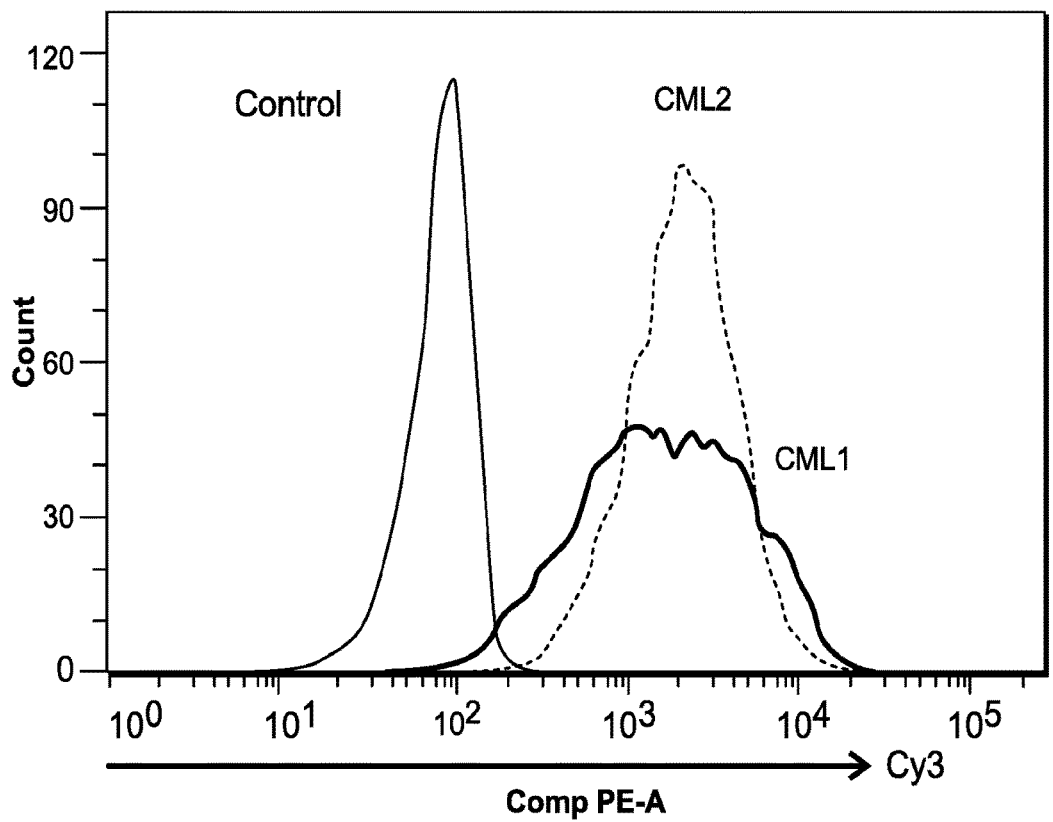
Figure 23G:
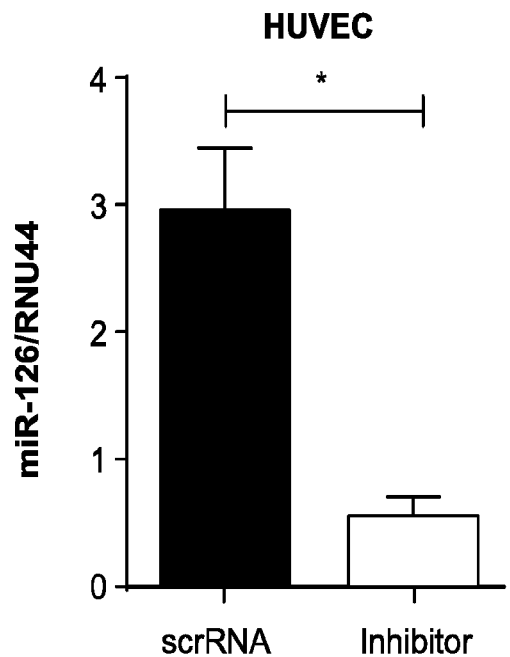
Figure 23H:
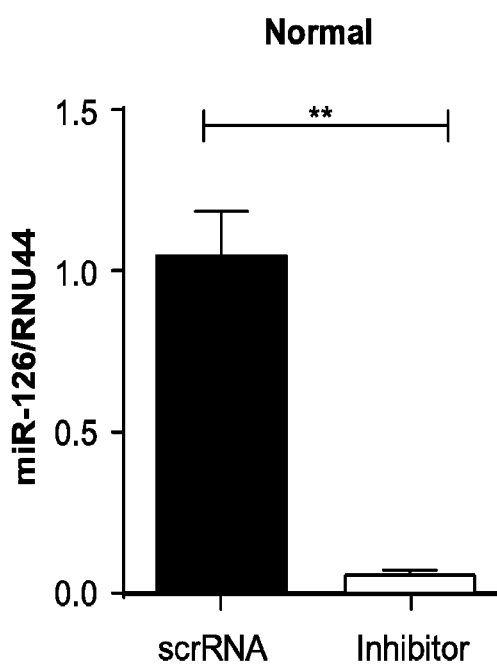
Figure 23I:
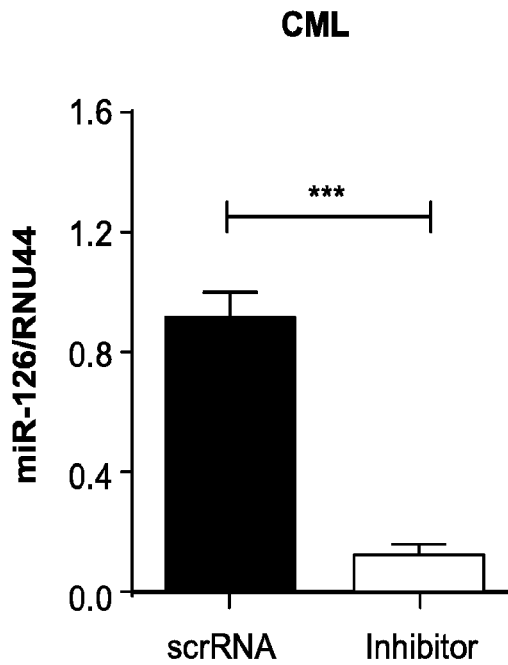
Figure 23J:
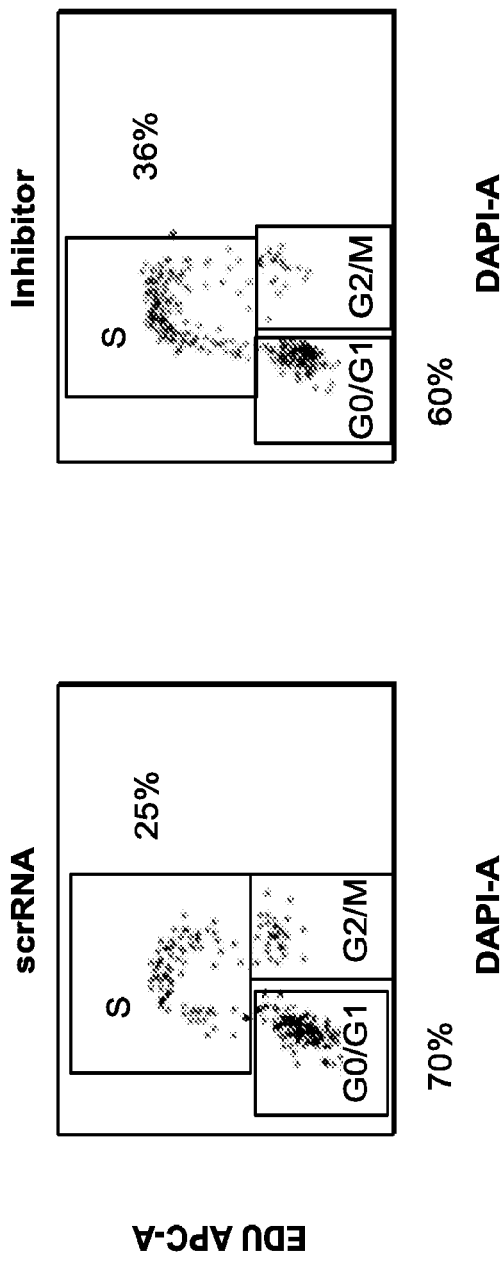
Figure 23K:
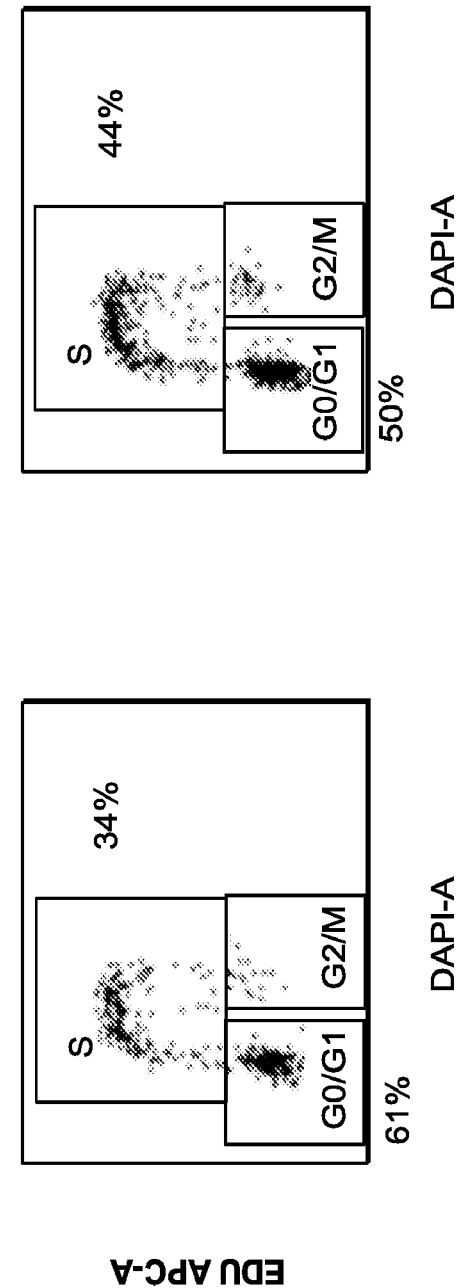

Example 12: Effective In Vitro and In Vivo Uptake and Gene Silencing Effects of the CpG-miR-126 Inhibitor Uptake test measured by flow cytometric analysis at 4 hours (FIG. 23A) and 24 hours (FIG. 23B) after addition of CpG-miR-126 inhibitor-Cy3, Ab-NPs or TF-NPs containing miR-126 inhibitor-Cy3, or naked miR-126 inhibitor-Cy3 in K562 cells. The experiment was replicated twice. miR-126 expression in K562 was measured by Q-RT-PCR at 24 hours (n=3) (FIG. 23D). Uptake in HUVEC (FIG. 23D), human normal (FIG. 23E) and CML (FIG. 23F) CD34+CD38− cells at 4 hours after addition of CpG-miR-126 inhibitor-Cy3 (500 nM) was measured by flow cytometry. miR-126 expression in HUVEC (FIG. 23G), normal (FIG. 23H) and CML (FIG. 23I) CD34+CD38− cells treated with CpG-miR-126 inhibitor (500 nM) for 24 hours is shown (n=4). One of the two cell cycling experiments in normal (FIG. 23J) and CML (FIG. 23K) CD34+CD38− cells treated with CpG-miR-126 inhibitor (500 nM) by EDU staining is shown.

Figure 25A:
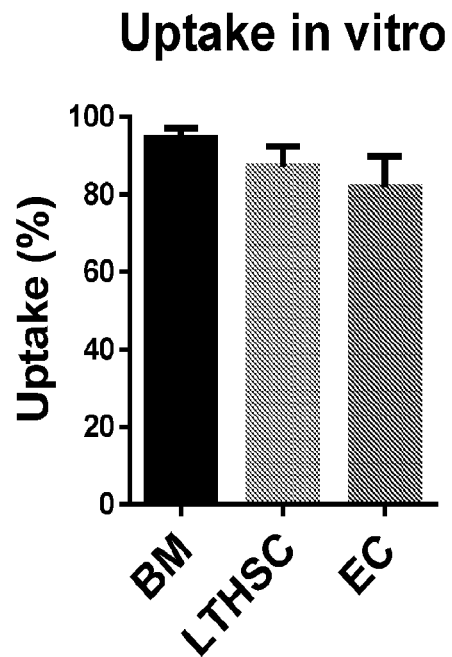
FIGS. 25A-25O. Effective in vitro and in vivo uptake and gene silencing effects of the CpG-miR-126 inhibitor. Murine CML BM, LTHSC and EC cells were treated with CpG-miR-126 inhibitor-Cy3 (500 nM) for 4 hours and then $Cy3^+$ cells were detected by flow cytometry (FIG. 25A). The cells were also collected at 24 hours and miR-126 expression was determined by Q-RT-PCR (FIG. 25B). Cell cycling was measured by EDU staining at 72 hours after addition of CpG-miR-126 inhibitor in CML BM LTHSC. One of the two representative plots is shown in (FIG. 25C). CML mice were treated with CpG-miR-126 inhibitor-Cy3 with one dose (5 mg/kg, iv injection) and Cy3 uptake in BM, LTHSC and EC was measured at 16 hours after treatment by flow cytometry (FIG. 25D). Normal and CML mice were also treated with CpG-miR-126 inhibitor (5 mg/kg/day, iv, daily) for 3 days and BM, LTHSC and EC from femurs were sorted and miR-126 expression was determined by Q-RT-PCR (FIGS. 25E-25F). Wild type B6 mice were treated with CpG-scrRNA (scrRNA) or CpG-miR-126 inhibitor (Inhibitor) (5 mg/kg/day, iv injection) for 3 weeks and BM cells were collected and analyzed. Red cell (RBC, FIG. 25G), WBC (FIG. 25H), PLT (FIG. 25I), BM mononuclear cell (FIG. 25J), LTHSC (FIG. 25K) and EC (FIG. 25L) numbers are shown. BM cells (CD45.2) from the treated normal mice were transplanted into CD45.1 congenic recipient mice and the donor cell engraftment in blood (FIG. 25M) and in BM and spleen at 16 weeks (FIG. 25N) and the donor LTHSC number in BM at 16 weeks (FIG. 25O) was monitored. Results shown represent mean±SEM. $*p<0.05$, $p<0.01$, $*p<0.001$. Abbreviations: EC (endothelial cells); PLT (platelet).
Figure 25B:
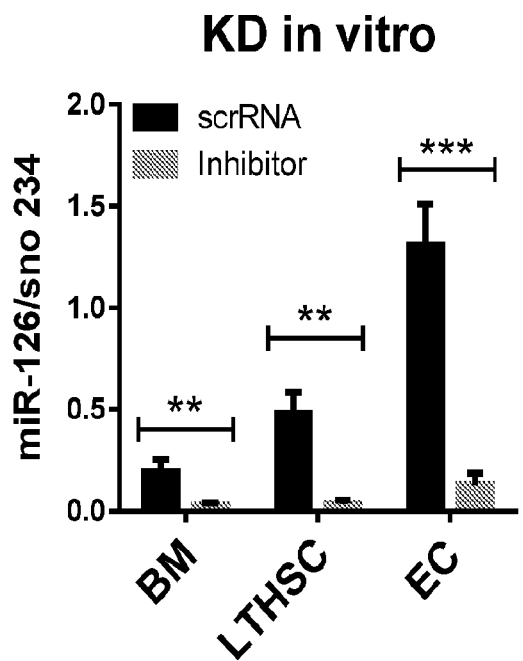
Figure 25C:
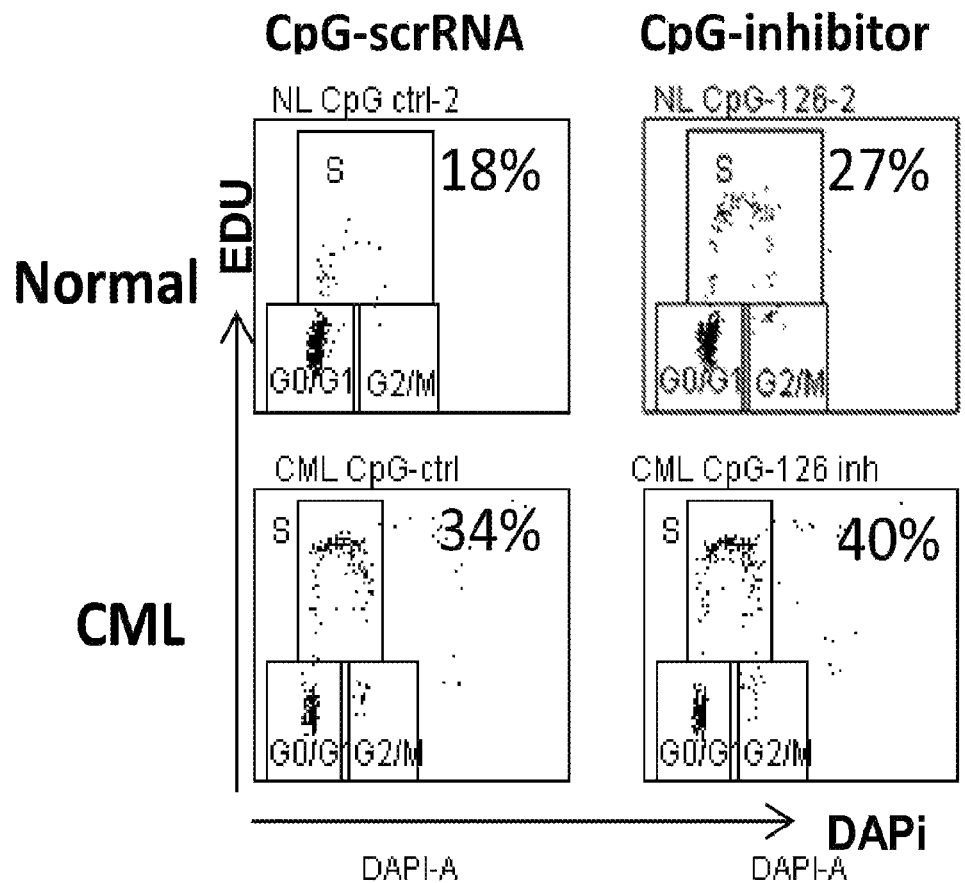
Figure 25D:
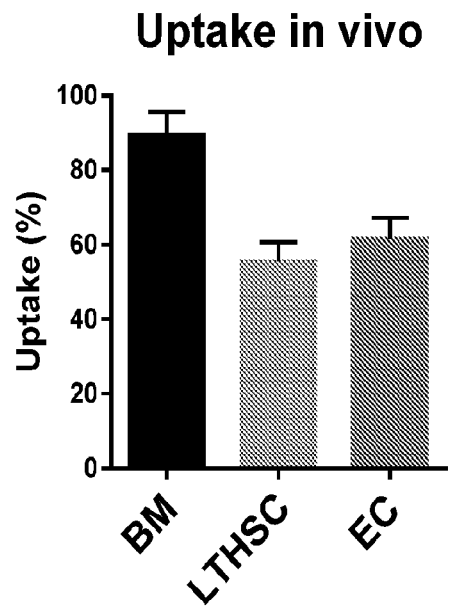
Figure 25E:
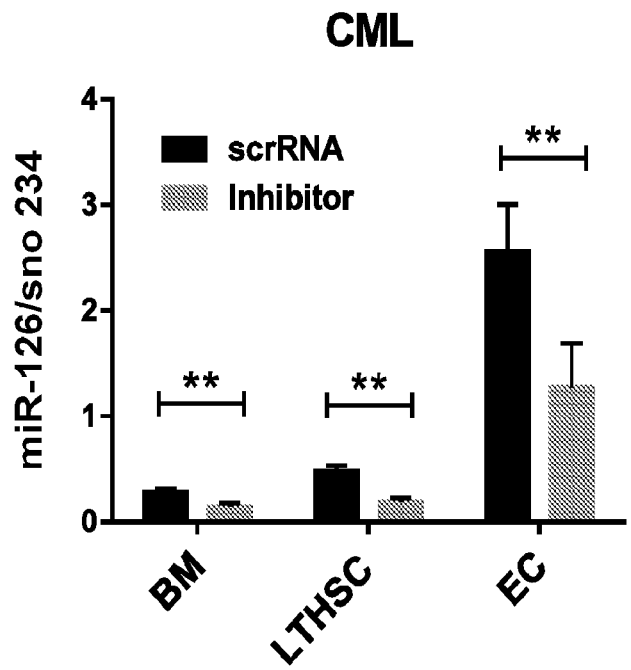
Figure 25F:
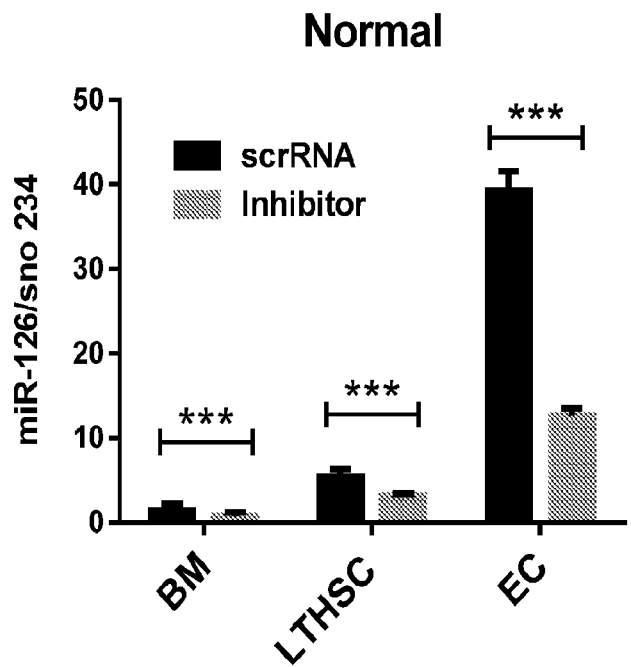
Figure 25G:
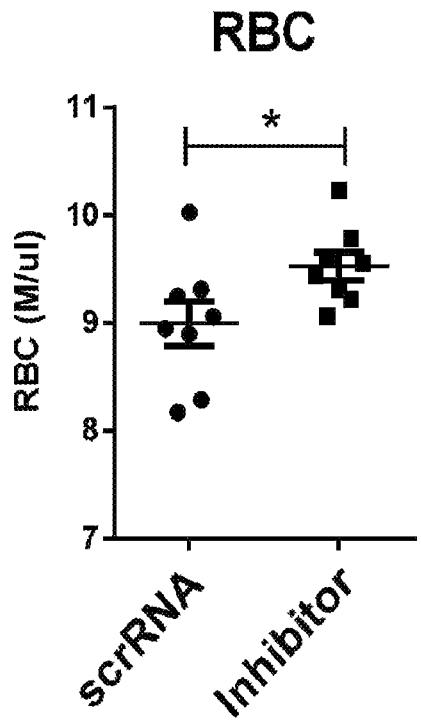
Figure 25H:
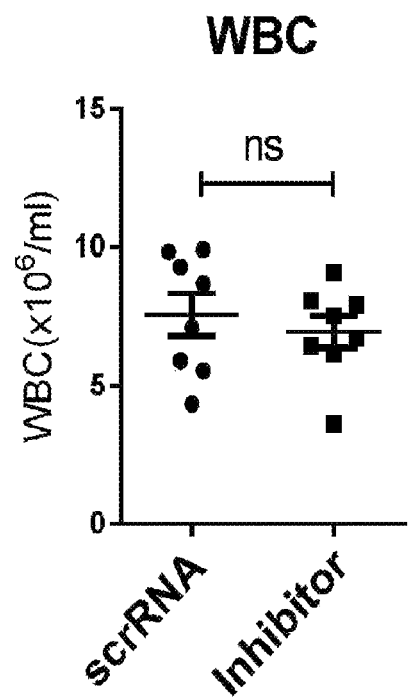
Figure 25I:
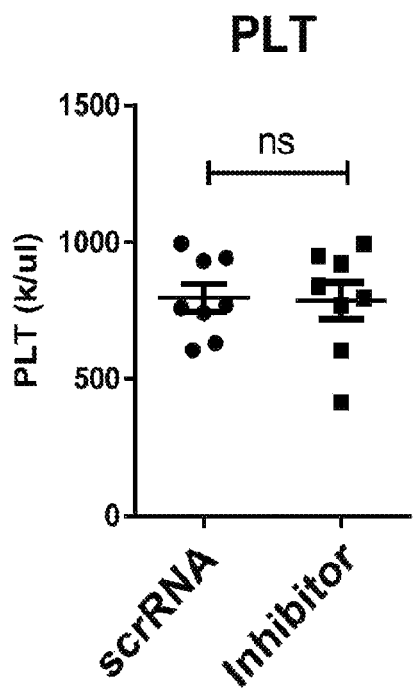
Figure 25J:
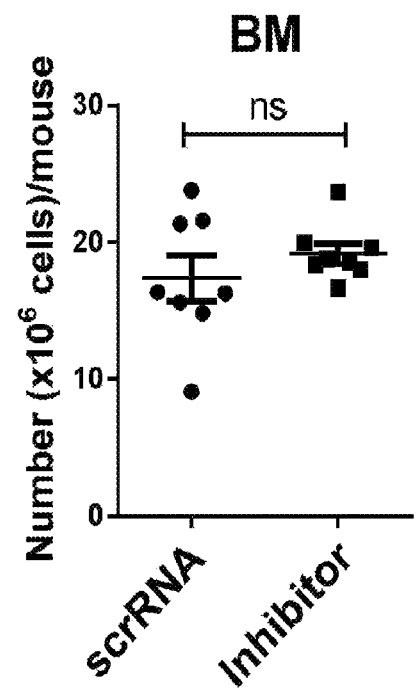
Figure 25K:
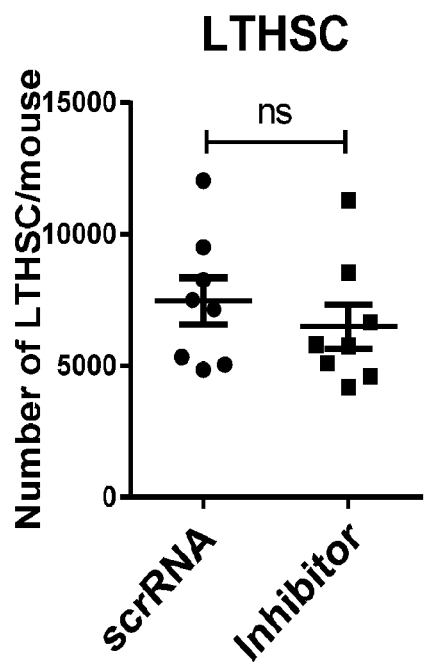
Figure 25L:
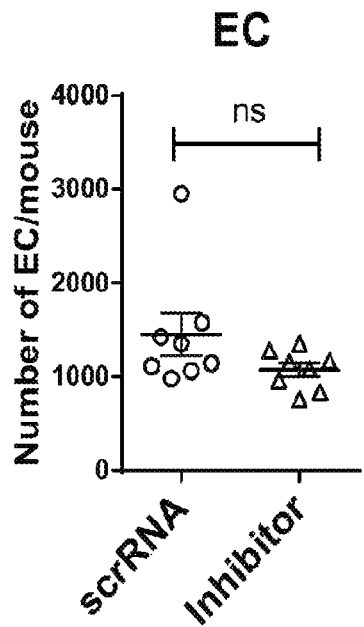
Figure 25M:
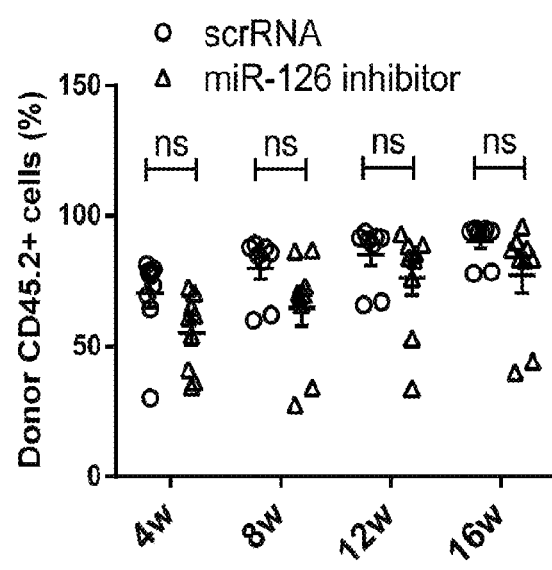
Figure 25N:
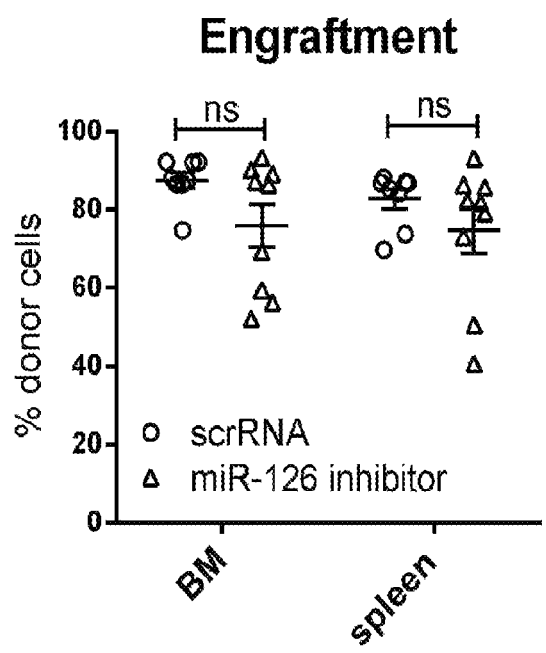
Figure 25O:
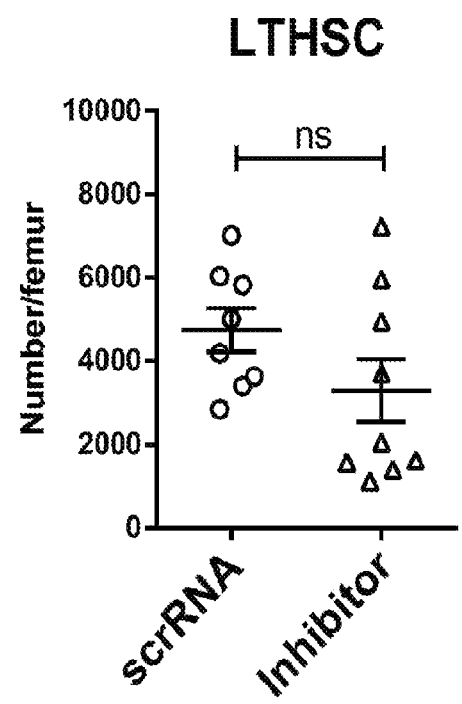

Murine CML BM, LTHSC and EC cells were treated with CpG-miR-126 inhibitor-Cy3 (500 nM) for 4 hours and then Cy3+ cells were detected by flow cytometry (FIG. 25A). The cells were also collected at 24 hours and miR-126 expression was determined by Q-RT-PCR (FIG. 25B). Cell cycling was measured by EDU staining at 72 hours after addition of CpG-miR-126 inhibitor in CML BM LTHSC. One of the two representative plots is shown in (FIG. 25C). CML mice were treated with CpG-miR-126 inhibitor-Cy3 with one dose (5 mg/kg, iv injection) and Cy3 uptake in BM, LTHSC and EC was measured at 16 hours after treatment by flow cytometry (FIG. 25D). Normal and CML mice were also treated with CpG-miR-126 inhibitor (5 mg/kg/day, iv, daily) for 3 days and BM, LTHSC and EC from femurs were sorted and miR-126 expression was determined by Q-RT-PCR (FIGS. 25E-25F). Wild type B6 mice were treated with CpG-scrRNA (scrRNA) or CpG-miR-126 inhibitor (Inhibitor) (5 mg/kg/day, iv injection) for 3 weeks and BM cells were collected and analyzed. Red cell (RBC, FIG. 25G), WBC (FIG. 25H), PLT (FIG. 25I), BM mononuclear cell (FIG. 25J), LTHSC (FIG. 25K) and EC (FIG. 25L) numbers are shown. BM cells (CD45.2) from the treated normal mice were transplanted into CD45.1 congenic recipient mice and the donor cell engraftment in blood (FIG. 25M) and in BM and spleen at 16 weeks (FIG. 25N) and the donor LTHSC number in BM at 16 weeks (FIG. 25O) was monitored. Results shown represent mean±SEM. *p<0.05, p<0.01, *p<0.001. Abbreviations: EC (endothelial cells); PLT (platelet).

Figure 24A:
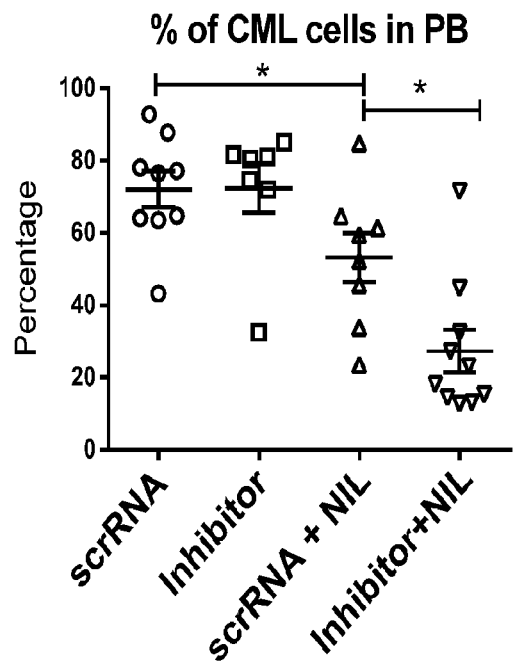
Figure 24B:
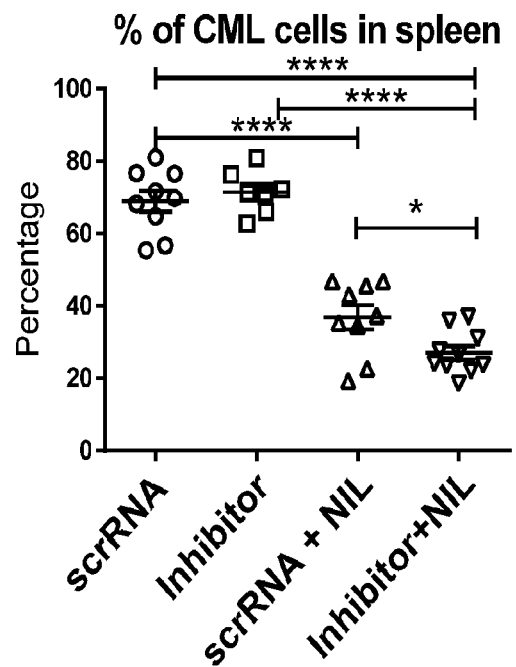
Figure 24C:
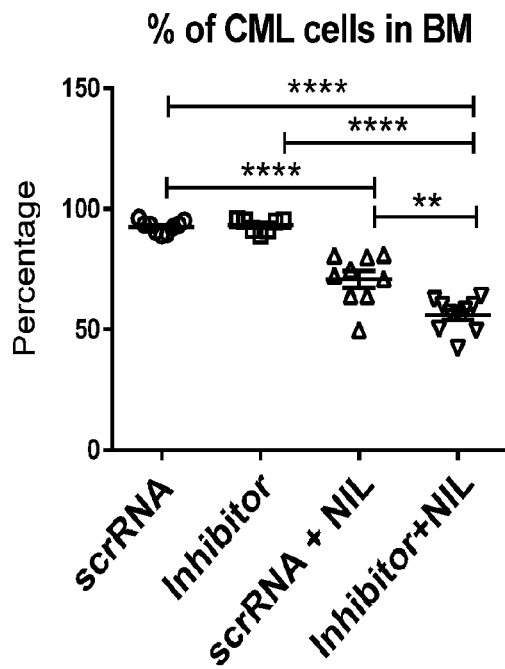
Figure 24D:
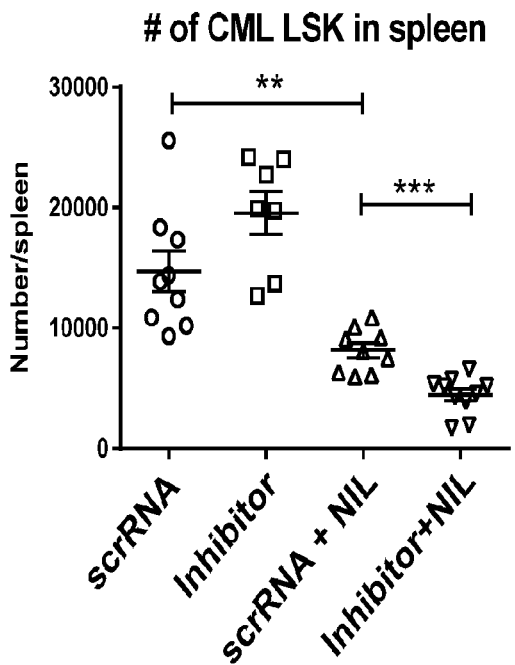
Figure 24E:
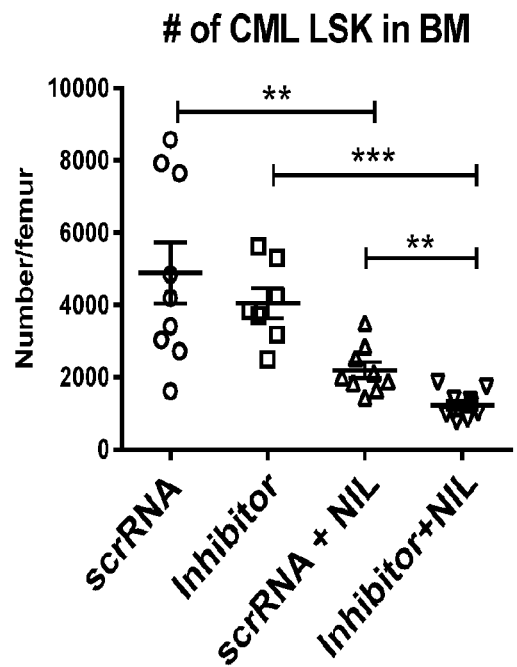
Figure 24F:
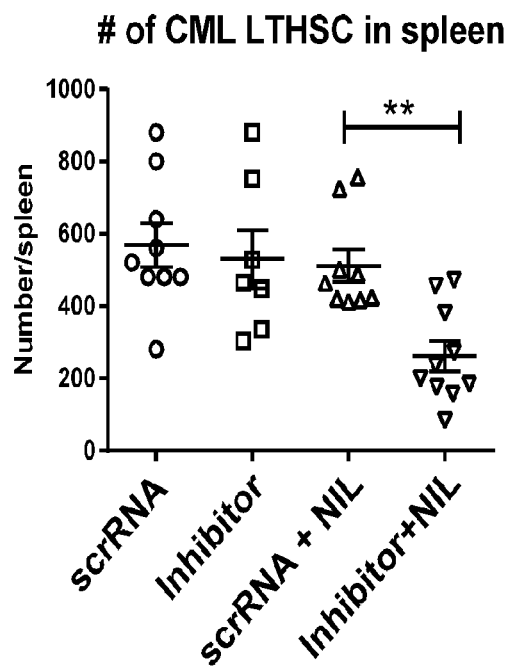
Figure 24G:
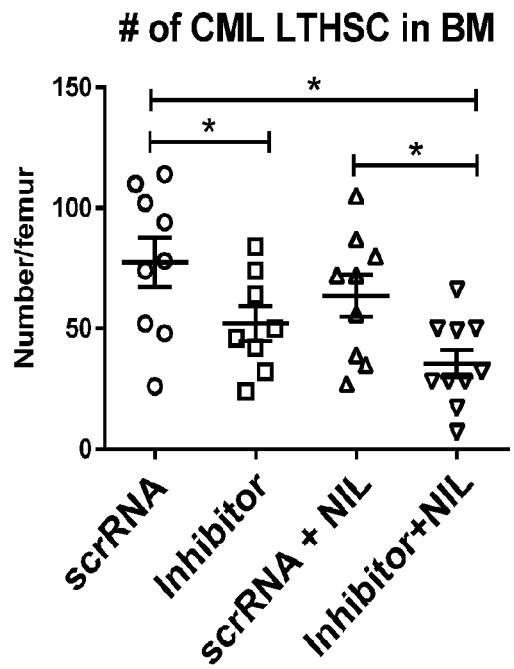
Figure 24H:
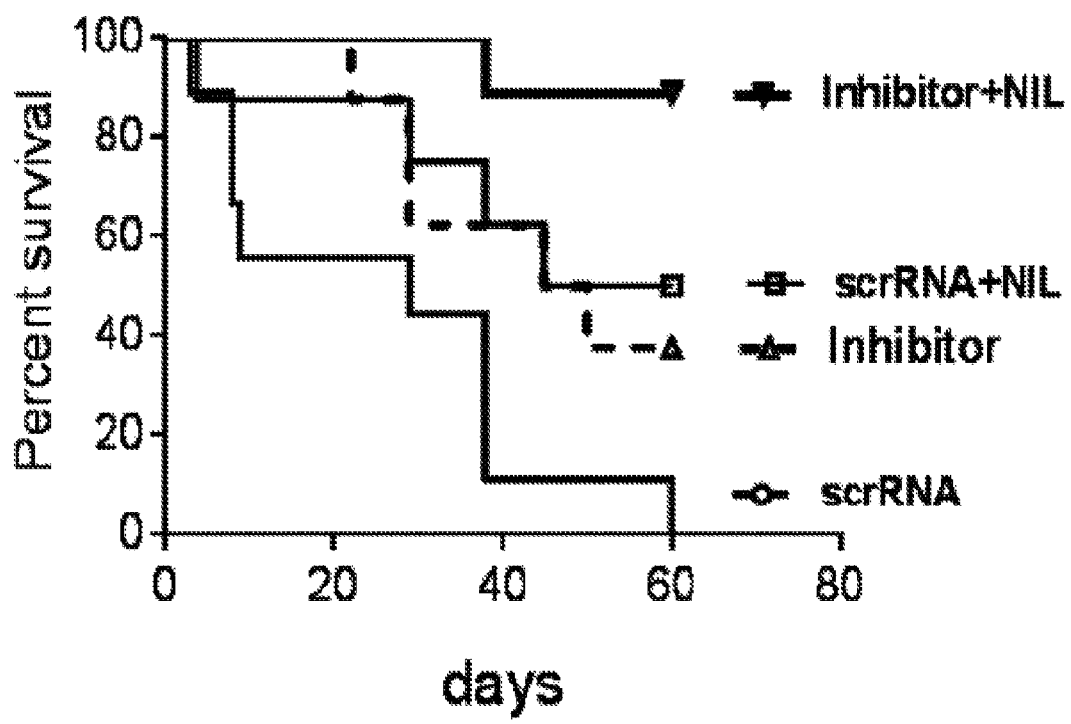

Example 13: Combination of a Compound Described Herein and Another Therapeutic Agent Knockdown of miR-126 by CpG-miR-126 inhibitor enhances elimination of mouse CML LSC in combination with NIL in vivo. BM cells from SCL-tTA/BCR-ABL mice (CD45.2) were transplanted into congenic B6 mice (CD45.1, n=40) to generate a cohort of mice with CML-like disease. Following confirmation of CML development at 4 weeks after transplantation, mice were randomly divided into 4 groups (n=10 each) and treated with CpG-miR-126 inhibitor (5 mg/kg i.v.4 times a week), CpG-scrRNA (5 mg/kg, i.v. 4 times a week), CpG-miR-126 inhibitor plus NIL (50 mg/kg, daily by gavage), and CpG-scrRNA plus NIL for 3 weeks. Percentage of donor CML cells in peripheral blood (PB) (FIG. 24A), spleen (FIG. 24B) and bone marrow (BM) (FIG. 24C), numbers of donor CML LSK in spleen (FIG. 24D) and BM (FIG. 24E), and numbers of donor CML long term hematopoietic stem cells (LTHSC) in spleen (FIG. 24F) and BM (FIG. 24G) after 3 weeks' treatment were measured. Another cohort of mice was treated for 3 weeks and then followed for survival studies after 3 weeks of treatment (n=10 in each group) (FIG. 24H). BM cells (CD45.2) from treated leukemic mice (3 weeks) were pooled, and 4×10$^6$, 2×10$^6$, 1×10$^6$, and 5×10$^5$ cells/mouse were transplanted into secondary congenic CD45.1 recipient mice irradiated at 900cGy (n=6 mice/dose/condition×4 doses×4 conditions=96 mice). The recipient mice were monitored for 16 weeks for CML cell engraftment in blood and leukemia development by WBC count. Frequency of LIC was quantified using L-Calc software (FIG. 24I). Abbreviations: NIL (Nilotinib); PB (peripheral blood); BM (bone marrow); LTHSC (long term hematopoietic stem cells); LIC (leukemia-initiating cells); LSK (lineage: Sca-1+c-kit+ cells).

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

Embodiments disclosed herein include embodiments P1 to P51 following.

Embodiment P1

An isolated compound comprising a phosphorothioated oligodeoxynucleotide (ODN) conjugated to an anti-microRNA (anti-miR) sequence.

Embodiment P2

The compound of embodiment P1, wherein said anti-miR sequence is an anti-miR126, anti-miR142, anti-miR155, anti-miR9, anti-miR10b, anti-miR21, anti-miR17, or anti-miR92 nucleic acid sequence.

Embodiment P3

An isolated compound comprising a phosphorothioated oligodeoxynucleotide (ODN) conjugated to a microRNA (miRNA) mimic nucleic acid sequence (miRNA-mimic).

Embodiment P4

The compound of embodiment P3, wherein said mimic is a miR126-mimic, miR142-mimic, miR155-mimic, miR9-mimic, miR10b-mimic, miR21-mimic, miR17-mimic, or miR92-mimic nucleic acid sequence Embodiment P5

The compound of either of embodiment P1 or embodiment P3, further comprising one or more linkers between the ODN and anti-miR or miRNA-mimic sequence, respectively.

Embodiment P6

The compound of embodiment P5, wherein the linker comprises a substituted or unsubstituted alkylene or heteroalkylene linker.

Embodiment P 7

The compound of embodiment P6, wherein the substituted alkylene or heteroalkylene linker comprises a moiety selected from the group consisting of: an azide group, a protected amino group, N-hydroxysuccinimide (NHS) group, and a protected sulfhydryl group.

Embodiment P8

The compound of embodiment P7, wherein the substituted alkylene or heteroalkylene linker comprising a protected sulfhydryl group is conjugated to a moiety selected from the group consisting of: divinyl sulfone derivative, acryloyl derivative, and maleimido derivative.

Embodiment P9

The compound of embodiment P8, wherein the acryloyl derivative is acryloyl chloride.

Embodiment P10

The compound of embodiment P6, wherein the substituted alkylene or heteroalkylene linker is conjugated to polyethylene glycol (PEG) or bisphosphonate moiety.

Embodiment P11

The compound of embodiment P6, wherein the alkylene or heteroalkylene linker comprises an unsubstituted C3 heteroalkylene.

Embodiment P12

The compound of embodiment P6, wherein the alkylene or heteroalkylene linker comprises an unsubstituted C6 to C12 heteroalkylene.

Embodiment P13

The compound of embodiment P5, wherein the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P14

The compound of embodiment P5, wherein the linker is a substituted or unsubstituted C1-C40 alkylene, substituted or unsubstituted 2 to 40 membered heteroalkylene, substituted or unsubstituted C3-C8 cycloalkylene, substituted or unsubstituted 3 to 8 membered heterocycloalkylene, substituted or unsubstituted C6-C10 arylene, or substituted or unsubstituted 5 to 10 membered heteroarylene.

Embodiment P15

The compound of embodiment P5, wherein the linker is an unsubstituted C1-C40 alkylene, unsubstituted 2 to 40 membered heteroalkylene, unsubstituted C3-C8 cycloalkylene, unsubstituted 3 to 8 membered heterocycloalkylene, unsubstituted C6-C10 arylene, or unsubstituted 5 to 10 membered heteroarylene.

Embodiment P16

The compound of embodiment P5, wherein the linker is a substituted 2 to 40 membered heteroalkylene.

Embodiment P17

The compound of either of embodiment P1 or embodiment P3, wherein said anti-miR or miRNA-mimic sequence, respectively, is chemically modified.

Embodiment P18

The compound of embodiment P17, wherein said anti-miR or miRNA mimic sequence, respectively, comprises a chemical modification selected from the group consisting of a 2' 0-Methyl, 2'-deoxy-2'fluoro, 2'-deoxy, a universal base, 5-C-methyl, an inverted deoxy abasic residue incorporation, and a locked nucleic acid.

Embodiment P19

The compound of embodiment P18, wherein said modification is positioned at the terminal nucleobase of said anti-miR or miRNA-mimic sequence, respectively.

Embodiment P20

The compound of embodiment P18, wherein the modification is not positioned at the terminal nucleobase of said anti-miR or miRNA-mimic sequence, respectively.

Embodiment P21

The compound of embodiment P18, wherein said modification protects against serum-derived nucleases.

Embodiment P22

The compound of either of embodiment P1 or embodiment P3, wherein said ODN sequence comprises a CpG-ODN nucleic acid sequence selected from the group consisting of: a Class A CpG-ODN nucleic acid sequence, a Class B CpG-ODN nucleic acid sequence, and a Class C CpG-ODN nucleic acid sequence.

Embodiment P23

The compound of embodiment P1 or P3, wherein said ODN comprises phosphodiester derivative linkage.

Embodiment P24

The compound of embodiment P23, wherein said phosphodiester derivative linkage in said CpG nucleic acid sequence is selected from the group consisting of: a phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, and O-methylphosphoroamidite linkage.

Embodiment P25

A pharmaceutical composition comprising a pharmaceutically acceptable excipient and the compound of either of embodiment P1 or embodiment P3.

Embodiment P26

The pharmaceutical composition of embodiment P25, further comprising a second therapeutic agent.

Embodiment P27

The pharmaceutical composition of embodiment P26, wherein the second therapeutic agent is selected from the group consisting of: anti-tumor or anti-cancer agent, cytotoxic agent, cytostatic agent, anti-inflammatory agent, analgesic, anti-infective agent, growth inhibitory agent, immunogenic agent, immunomodulatory agent, and chemokine.

Embodiment P28

The pharmaceutical composition of embodiment P27, wherein said anti-cancer agent is a cell death promoting agent.

Embodiment P29

The pharmaceutical composition of embodiment P27, wherein said second therapeutic agent is selected from the group consisting of: Actinomycin D/Dactinomycin, Bleomycin, Daunorubicin, Doxorubicin, Doxorubicin (pegylated liposomal), Epirubicin, Idarubicin, Mitomycin, Mitoxantrone, Etoposide, Docetaxel, Irinotecan, Paclitaxel, Topotecan, Vinblastine, Vincristine, Vinorelbine, Carboplatin, Cisplantin, Oxaliplatin, Alemtuzamab, BCG, Bevacizumab, Cetuximab, Denosumab, Erlotinib, Gefitinib, Imatinib, Interferon, Ipilimumab, Lapatinib, Monomethyl auristatin E (MMEA), Mertansine (DM1), Rituximab, Sunitinib, Sorafenib, Temsirolimus, and Trastuzumab, or any combination(s) thereof.

Embodiment P30

A method of treating cancer in a subject in need thereof, the method comprising administering to said subject an effective amount of the compound of either of embodiment P1 or embodiment P3 or the pharmaceutical composition of embodiment P25.

Embodiment P31

The method of embodiment P30, wherein the compound of either of embodiment P1 or embodiment P3, or the pharmaceutical composition of embodiment P25, comprises anti-miR126 sequence or miR142-mimic, respectively.

Embodiment P32

The method of embodiment P30, wherein the cancer is a hematopoietic cell cancer.

Embodiment P33

The method of embodiment P30, wherein the cancer in not a hematopoietic cell cancer.

Embodiment P34

The method of embodiment P30, wherein the cancer is myeloma or acute myeloid leukemia.

Embodiment P35

The method of embodiment P30, wherein the cancer is prostate cancer, breast cancer, glioblastoma, ovarian cancer, lung cancer, head and neck cancer, esophageal cancer, skin cancer, melanoma, brain cancer, colorectal cancer, lymphoma, or myeloma, pancreatic cancer, chronic myeloid leukemia (CML), or myelodysplastic syndromes (MDS).

Embodiment P36

The method of any one of embodiments P30-P35, wherein the compound or the composition is administered to the subject by intravenous, parenteral, subcutaneous, intramuscular, transdermal, intraperitoneal, intranasal, aerosol, oral, or topical administration.

Embodiment P37

The method of any one of embodiments P30-P36, wherein said treatment is dose-dependent of said compound or composition.

Embodiment P38

The method of any one of embodiments P30-P36, wherein about 0.001 mg/kg to about 100 mg/kg of said compound is administered to said subject.

Embodiment P39

The method of any one of embodiments P30-P35, wherein said cancer is a relapsed cancer after chemotherapy.

Embodiment P40

The method of embodiment P39, wherein the relapsed cancer is chemotherapy resistant.

Embodiment P41

The method of any one of embodiments P30-P40, wherein said compound or said composition promotes cell-cycle entry of cancer stem cells, thereby treating said cancer.

Embodiment P42

The method of embodiment P41, wherein said cancer stem cells are leukemic stem cells (LSCs).

Embodiment P43

The method of embodiment P42, wherein said LSCs are CD34+CD38+ committed progenitor cells or primitive CD34+CD38− progenitor cells.

Embodiment P44

A method of reducing the activity of microRNA in a cell comprising contacting the cell with an effective amount of the compound of embodiment P1.

Embodiment P45

The method of one of embodiment P44, wherein said cell is a cancer cell.

Embodiment P46

The method of embodiment P45, wherein said cell is an acute myeloid lymphoid (AML) cell, prostate cancer cell, breast cancer cell, glioblastoma cell, ovarian cancer cell, lung cancer cell, head and neck cancer cell, esophageal cancer cell, skin cancer cell, melanoma cell, brain cancer cell, colorectal cancer cell, lymphoma cell, myeloma cell, pancreatic cancer cell, chronic myeloid leukemia (CML cell, or myelodysplastic syndromes (MDS) cell.

Embodiment P47

The method of embodiment P46, wherein said AML cell is from the bone marrow.

Embodiment P48

The method of any one of embodiments P44-P47, wherein said cell is a cultured cell in vitro.

Embodiment P49

The method of any one of embodiments P44-P47, wherein said cell is in situ in a host.

Embodiment P50

The method of any one of embodiments P44-P47, wherein said cell is in a cultured tissue ex vivo.

Embodiment P51

The method of any one of embodiments P44-P47, wherein said contacting step is free of viral transduction.

Embodiment P52

The method of any one of embodiments P44-P47, wherein said contacting step is free of viral transduction and said cell is contacted with the compound of embodiment P1.

Embodiment P53

The method of any one of embodiments P44-P52, wherein said cell is contacted with about 1-100 nanomolar concentration of said compound.

---

What is claimed is:

1. A pharmaceutical composition comprising a pharmaceutically acceptable excipient, a compound comprising a phosphorothioated CpG oligodeoxynucleotide (CpG-ODN) conjugated to an anti-miR126 nucleic acid, and an anti-tumor or anti-cancer agent.

2. The pharmaceutical composition compound of claim 1, further comprising a covalent linker between the CpG-ODN and anti-miR126 nucleic acid.

3. The pharmaceutical composition of claim 2, wherein the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

4. The pharmaceutical composition of claim 2, wherein the linker is a substituted or unsubstituted $C_1$-$C_{40}$ alkylene, substituted or unsubstituted 2 to 40 membered heteroalkylene, substituted or unsubstituted C$_3$-C$_8$ cycloalkylene, substituted or unsubstituted 3 to 8 membered heterocycloalkylene, substituted or unsubstituted C$_6$-C$_{10}$ arylene, or substituted or unsubstituted 5 to 10 membered heteroarylene.

5. The pharmaceutical composition of claim 2, wherein the linker is an unsubstituted C$_1$-C$_{40}$ alkylene, unsubstituted 2 to 40 membered heteroalkylene, unsubstituted C$_3$-C$_8$ cycloalkylene, unsubstituted 3 to 8 membered heterocycloalkylene, unsubstituted C$_6$-C$_{10}$ arylene, or unsubstituted 5 to 10 membered heteroarylene.

6. The pharmaceutical composition of claim 2, wherein the linker is a substituted 2 to 40 membered heteroalkylene.

7. The pharmaceutical composition of claim 1, wherein said anti-miR126 nucleic acid is chemically modified.

8. The pharmaceutical composition of claim 7, wherein said anti-miR126 nucleic acid comprises a chemical modification selected for the group consisting of a 2' O-Methyl, 2'-deoxy-2'fluoro, 2'-deoxy, a universal base, 5-C-methyl, an inverted deoxy abasic residue incorporation, and a locked nucleic acid.

9. The pharmaceutical composition of claim 8, wherein said modification is positioned at the terminal nucleobase of said anti-miR126 nucleic acid.

10. The pharmaceutical composition of claim 8, wherein the modification is not positioned at the terminal nucleobase of said anti-miR126 nucleic acid.

11. The pharmaceutical composition of claim 8, wherein said modification protects against serum-derived nucleases.

12. The pharmaceutical composition of claim 1, wherein said CpG-ODN nucleic acid sequence is selected from the group consisting of a Class A CpG-ODN nucleic acid sequence, a Class B CpG-ODN nucleic acid sequence, and a Class C CpG-ODN nucleic acid sequence.

13. The pharmaceutical composition of claim 1, wherein said CpG-ODN comprises phosphodiester derivative linkage selected from the group consisting of a phosphoramidate linkage, phosphorodiamidate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, and O-methylphosphoroamidite linkage.

14. The pharmaceutical composition of claim 1, wherein said anti-cancer agent is a cell death promoting agent.

15. The pharmaceutical composition of claim 1, wherein said anti-cancer agent is selected from the group consisting of: Nilotinib, Actinomycin D / Dactinomycin, Bleomycin, Daunorubicin, Doxorubicin, Doxorubicin (pegylated liposomal), Epirubicin, Idarubicin, Mitomycin, Mitoxantrone, Etoposide, Docetaxel, Irinotecan, Paclitaxel, Topotecan, Vinblastine, Vincristine, Vinorelbine, Carboplatin, Cisplantin, Oxaliplatin, Alemtuzamab, BCG, Bevacizumab, Cetuximab, Denosumab, Erlotinib, Gefitinib, Imatinib, Interferon, Ipilimumab, Lapatinib, Monomethyl auristatin E (MMEA), Mertansine (DM1), Rituximab, Sunitinib, Sorafenib, Temsirolimus, and Trastuzumab, or any combination(s) thereof.

* * * * *